(12) United States Patent
Richter et al.

(10) Patent No.: US 11,851,489 B2
(45) Date of Patent: Dec. 26, 2023

(54) HETERODIMERIZING IG DOMAINS

(71) Applicant: UNIVERSITÄT STUTTGART, Stuttgart (DE)

(72) Inventors: Fabian Richter, Kirchheim Unter Teck (DE); Oliver Seifert, Stuttgart (DE); Roland Kontermann, Nürtingen (DE)

(73) Assignee: UNIVERSITÄT STUTTGART, Stuttgart (DE)

( * ) Notice: Subject to any disclaimer, the term of this patent is extended or adjusted under 35 U.S.C. 154(b) by 272 days.

(21) Appl. No.: 16/615,536

(22) PCT Filed: Jun. 1, 2018

(86) PCT No.: PCT/EP2018/064538
§ 371 (c)(1),
(2) Date: Nov. 21, 2019

(87) PCT Pub. No.: WO2018/220216
PCT Pub. Date: Dec. 6, 2018

(65) Prior Publication Data
US 2020/0172619 A1    Jun. 4, 2020

(30) Foreign Application Priority Data
Jun. 1, 2017 (EP) .................................... 17174087

(51) Int. Cl.
| | | |
|---|---|---|
| *C07K 16/28* | (2006.01) | |
| *C07K 16/30* | (2006.01) | |
| *C07K 16/32* | (2006.01) | |
| *C07K 16/40* | (2006.01) | |
| *A61K 38/00* | (2006.01) | |

(52) U.S. Cl.
CPC ...... *C07K 16/2809* (2013.01); *C07K 16/2878* (2013.01); *C07K 16/30* (2013.01); *C07K 16/32* (2013.01); *C07K 16/40* (2013.01); *A61K 38/00* (2013.01); *C07K 2317/31* (2013.01); *C07K 2317/522* (2013.01); *C07K 2317/524* (2013.01); *C07K 2317/526* (2013.01); *C07K 2317/528* (2013.01); *C07K 2317/53* (2013.01); *C07K 2317/622* (2013.01); *C07K 2317/76* (2013.01); *C07K 2317/94* (2013.01)

(58) Field of Classification Search
None
See application file for complete search history.

(56) References Cited

U.S. PATENT DOCUMENTS

2014/0341906 A1* 11/2014 Taylor .................... C07K 16/18
435/69.6

FOREIGN PATENT DOCUMENTS

| WO | 2011/143545 | 11/2011 |
| WO | 2013/012733 | 1/2013 |

OTHER PUBLICATIONS

Rudikoff et al., PNAS 79: 1979-1983 (Year: 1982).*
Chen et al., EMBO J., 14: 2784-2794 (Year: 1995).*
Wu et al., J Mol Biol 294: 151-162 (Year: 1999).*
Piche-Nicholas et a., MABS 10(1): 81-94 (Year: 2018).*
Salfeld et al., Nature Biotech. 25(12): 1369-1372 (Year: 2007).*
Dall'Acqua., J. Immunol. 177:1129-1138 (Year: 2006).*
Burgess, et al., Journal of Cell Biology, vol. 111, pp. 2129-2138 (Year: 1990).*
Lazar et al., Molecular and Cellular Biology, vol. 8, pp. 1247-1252 (Year: 1988).*
The International Search Report (ISR) with Written Opinion for PCT/EP2018/064538 dated Jul. 16, 2018, pp. 1-14.

* cited by examiner

*Primary Examiner* — Phuong Huynh
(74) *Attorney, Agent, or Firm* — McDonnell Boehnen Hulbert & Berghoff LLP

(57) ABSTRACT

The present invention provides a protein complex comprising heterodimerizing regions HRI and HRII, each comprised of antiparallel β-strands and intervening regions wherein HRI and HRII are each interspersed fusion proteins of two human constant regions of an immunoglobulin or immunoglobulin-like proteins. The present invention also provides nucleic acid molecules comprising a sequence encoding said protein complexes and vectors comprising the nucleic acid. The present invention also provides the protein complex, the nucleic acid and the vector for use as a medicament. The present invention further provides a method of determining the amino acid sequence of HRI and/or of the amino acid sequence of HRII. The present invention also provides a method of producing amino acid chains of HRI and/or amino acid chains of HRII. The present invention further provides the protein complex for use in the N prophylaxis, treatment or diagnosis of a disorder or a disease.

Figure 1:
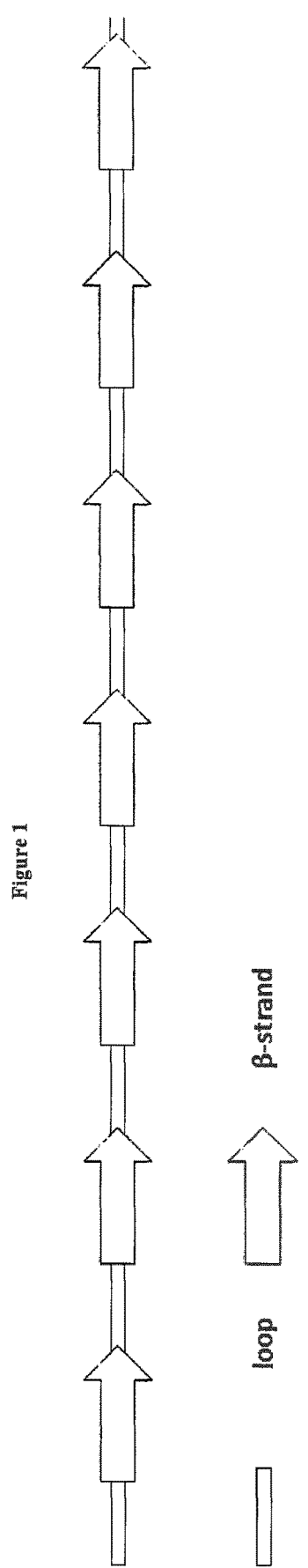
Figure 2:
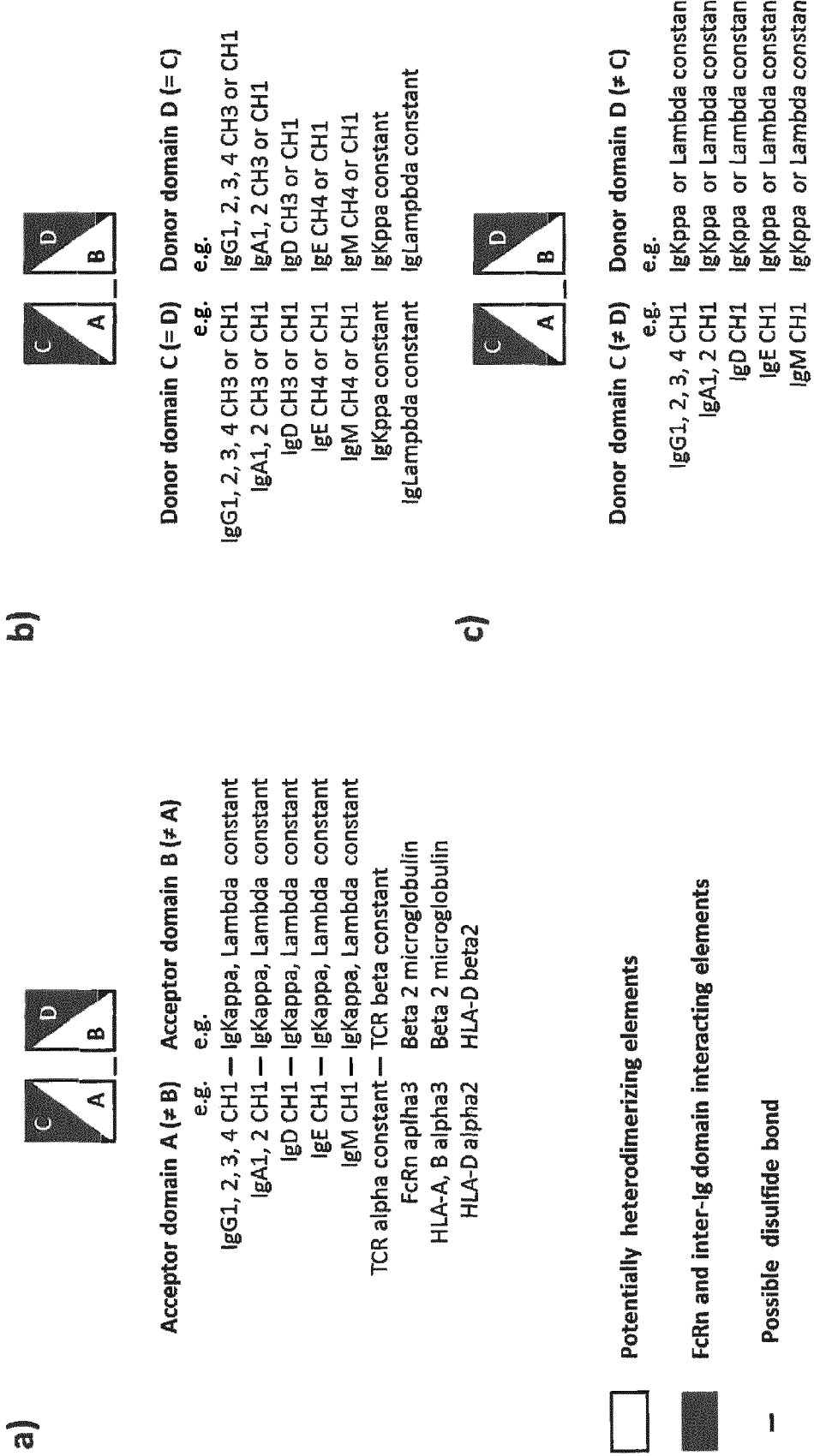

6 Claims, 39 Drawing Sheets
Specification includes a Sequence Listing.

Figure 4

Possibilities for $E_{1-n}$ to $H_{1-n}$

Various Ig Domains
Cytokines
TNFSF ligands
Toxins
·
·
·

Figure 8

```
Beta sheet:                     A                    B                  C                    D                     E                   F                  G
IgLCRC                                                                                                                                                              SEQ ID NO
Pos.            0         1         2         3         4         5         6         7         8         9        10        11        12        13        14
            1234567890123456789012345678901234567890123456789012345678901234567890123456789012345678901234567890123456789012345678901234
(1st CRI) g1_CH1 ----ASTKGP SVFPLAP SSKSTS--GGTAALGCLVKDYFP-EPV TVSWNSGALT--S--GVHTFPAV LQ-----SSSLGTQ----TYICNVNH KP-----SNTKVDK KVEPKSC----     1
(2nd CRI) g1_CH3 ------GQPREP QVYTLP PSRDELT-K-NQVSLTCLVKGFYP-SD---IAVEWES NGQPEN--N-YKTTPP VLD-----SDGS FFLYSKLT VDKSRWQQG--NV FSCSVM HEAL-----------      45
(HRI) CH31       ------GQPREPSVFPLAP SSKSTS--GGTAALGCLVKDYFP-SDIAVEWESGALT--S-GVHTFPAVLQ-----SSGLYSLSSVVTVPSSSLGTQ----TYSCSVMHEAL-----HNHYTQKSVERKSC-----      20

Beta sheet:                     A                    B                  C                    D                     E                   F                  G
IgLCRC                                                                                                                                                              SEQ ID NO
Pos.            0         1         2         3         4         5         6         7         8         9        10        11        12        13        14
            1234567890123456789012345678901234567890123456789012345678901234567890123456789012345678901234567890123456789012345678901234
(3rd CRI) k_CL   ----TVAAP SVFIFP PSDEQLK-S-GTASVVCLLNNFYP-REA KVQWKVDNALQSG--N SQESVTEQDS---KDSTYSLSST ILSKADYEKH--KV YACEVT QG-----LSSPVTKS FNRGEC----      18
(4th CRI) g1_CH3 ------GQPREPQVYTLP PSRDELT-K-NQVSLTCLVKGFYP-SD---IAVEWES NGQPEN--N-YKTTPPVLD-----SDGS FFLYSKLT VDKSRWQQG--NV FSCSVM HEAL-----------     45
(HRI) CH3k       ------GQPREPSVFIFPPSDEQLK-S-GTASVVCLVNNFYP-RDIAVEWEVDNALQSG--NSQESVTEQDS----KDSTYSLSST ILSKADYEKH--KVYSCSVMHEAL-----HNHYTQKSFNRGEC-----      21
```

Beta strands pre-delineated by PDB/IPSM.
Residues excluded manually from beta strands A-G according to structural alignment.
Residues added to beta strands A-G according to sequence and structural alignment.

Figure 17

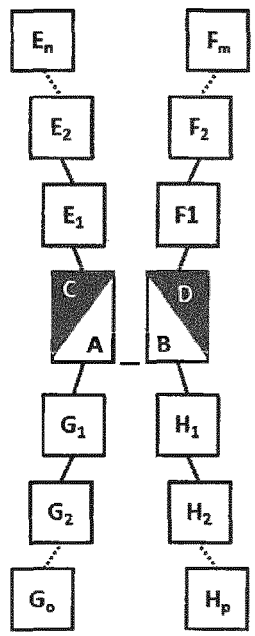

Example 3a
FAP$_N$CD3$_N$-hFc1k
A IgG1 CH1
B IgKappa constant
C/D IgG1 CH3
E$_1$/F$_1$ IgG1 CH2
E$_2$/F$_2$ Hinge
E$_3$ scFvhu36
F$_3$ scFvhuU3

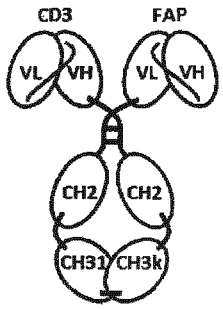

Example 3b
FAP$_N$CD3$_N$-Fc1k
A IgG1 CH1
B IgKappa constant
C/D IgG1 CH3
E$_1$/F$_1$ IgG1 CH2
E$_2$/F$_2$ Hinge w/o cysteines
E$_3$ scFvhu36
F$_3$ scFvhuU3

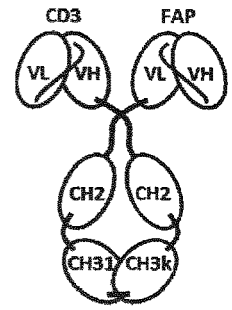

Figure 18

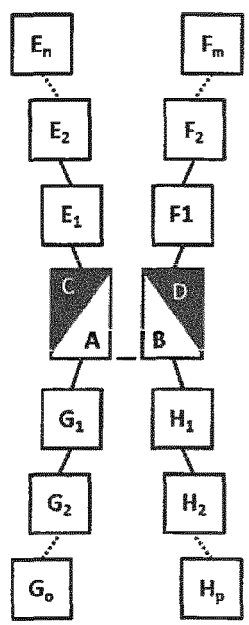

Example 4a
FAP$_N$CD3$_C$-hFc1k
A IgG1 CH1
B IgKappa constant
C/D IgG1 CH3
E$_1$/F$_1$ IgG1 CH2
E$_2$/F$_2$ Hinge
E$_3$ scFvhu36
H$_1$ Linker
H$_2$ scFvhuU3

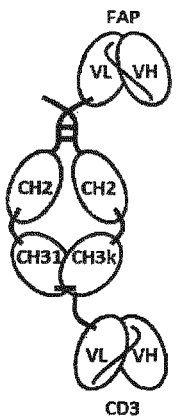

Example 4b
FAP$_N$CD3$_C$-Fc1k
A IgG1 CH1
B IgKappa constant
C/D IgG1 CH3
E$_1$/F$_1$ IgG1 CH2
E$_2$/F$_2$ Hinge w/o cysteines
H$_1$ Linker
E$_3$ scFvhu36
H$_2$ scFvhuU3

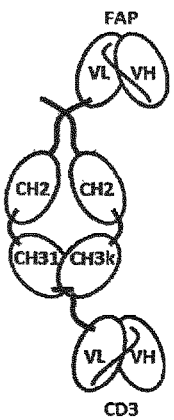

Figure 19

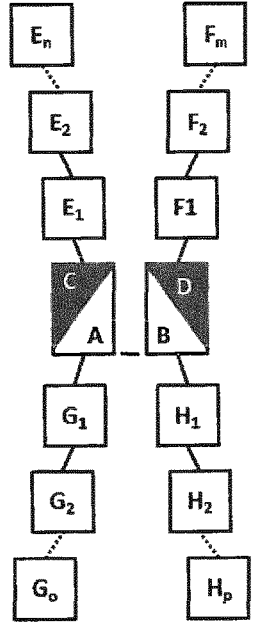

Example 5a
FAP$_{NN}$CD3$_C$-hFc1k
| | |
|---|---|
| A | IgG1 CH1 |
| B | IgKappa constant |
| C/D | IgG1 CH3 |
| E$_1$/F$_1$ | IgG1 CH2 |
| E$_2$/F$_2$ | Hinge |
| H$_1$ | Linker |
| E$_3$/F$_3$ | scFvhu36 |
| H$_2$ | scFvhuU3 |

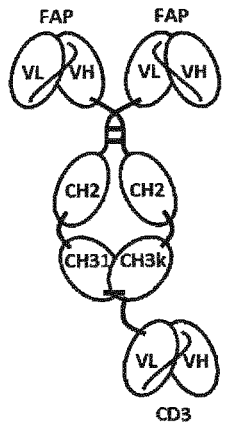

Example 5b
FAP$_{NN}$CD3$_C$-Fc1k
| | |
|---|---|
| A | IgG1 CH1 |
| B | IgKappa constant |
| C/D | IgG1 CH3 |
| E$_1$/F$_1$ | IgG1 CH2 |
| E$_2$/F$_2$ | Hinge w/o cysteines |
| H$_1$ | Linker |
| E$_3$/F$_3$ | scFvhu36 |
| H$_2$ | scFvhuU3 |

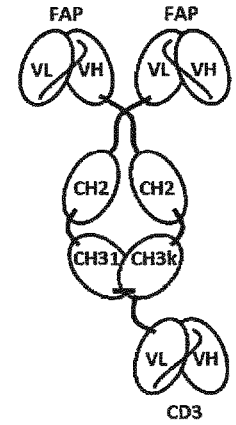

Figure 20

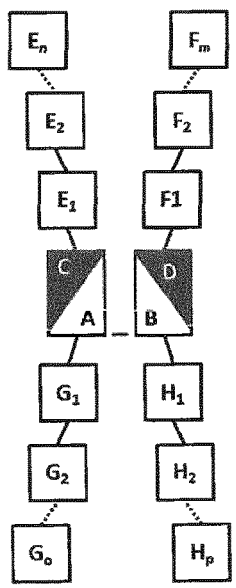

Example 6a
FAP$_{NC}$CD3$_C$-hFc1k
| | |
|---|---|
| A | IgG1 CH1 |
| B | IgKappa constant |
| C/D | IgG1 CH3 |
| E$_1$/F$_1$ | IgG1 CH2 |
| E$_2$/F$_2$ | Hinge |
| G$_1$/H$_1$ | Linker |
| E$_3$/G$_2$ | scFvhu36 |
| H$_2$ | scFvhuU3 |

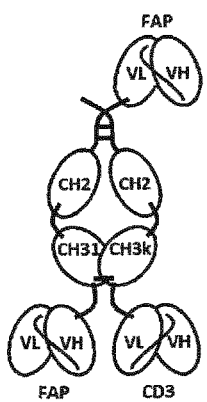

Example 6b
FAP$_{NC}$CD3$_C$-Fc1k
| | |
|---|---|
| A | IgG1 CH1 |
| B | IgKappa constant |
| C/D | IgG1 CH3 |
| E$_1$/F$_1$ | IgG1 CH2 |
| E$_2$/F$_2$ | Hinge w/o cysteines |
| G$_1$/H$_1$ | Linker |
| E$_3$/G$_2$ | scFvhu36 |
| H$_2$ | scFvhuU3 |

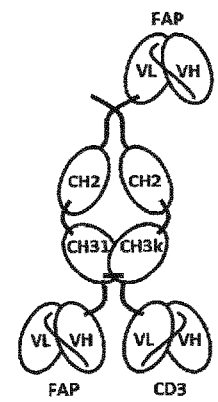

Figure 22
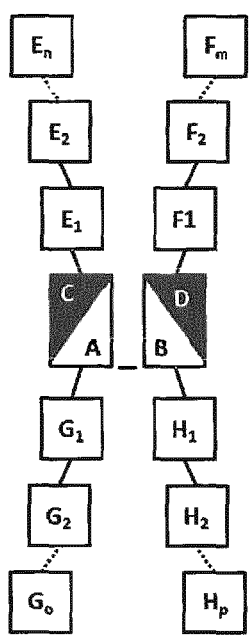
Example 7a
Bispecific-IgG
A        FcRn alpha 3
B        beta2 microglobulin
C/D      IgG1 CH3
$E_1/F_1$  IgG1 CH2
$E_2/F_2$  Hinge
$G_1$    Fab fragment (Antigen X)
$H_1$    Fab as described in Expl. 7b
Example 7b
Alternatively dimerized Fab
A        TCR alpha constant
B        TCR beta constant
C        IgG1 CH1
D        Igkappa CL
$E_1$    VH (anti Y)
$F_1$    VL (anti Y)
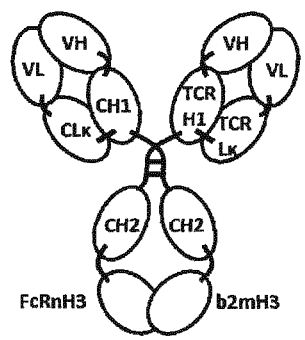

Figure 23
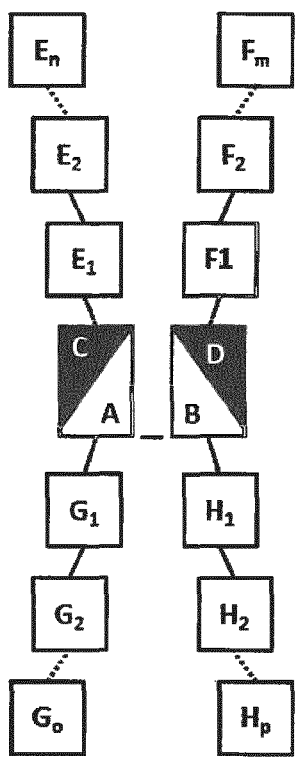
Example 8
Fv13.7$_X$-Fc1k
A    IgG1 CH1
B    IgKappa constant
C/D  IgG1 CH3
E$_1$/F$_1$ IgG1 CH2
E$_2$/F$_2$ Linker sequence
E$_3$   VL13.7
F$_3$   VH13.7
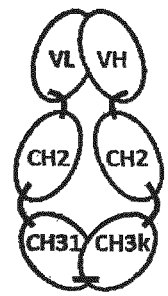
Light chain:
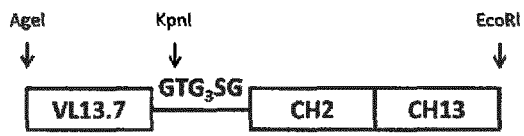
Heavy chain:
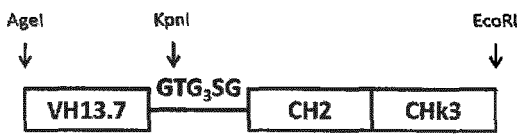

Figure 25
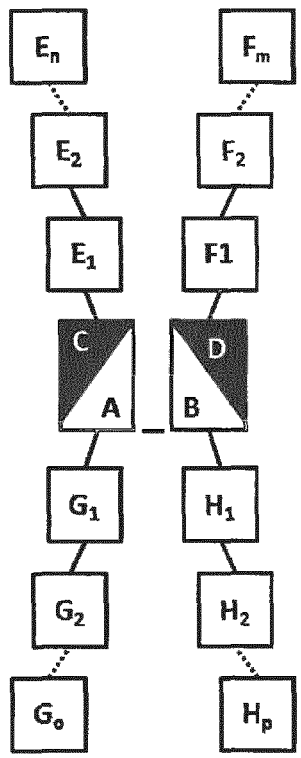
Example 9
FvCD3-Fc1k-scFvHer3$_2$
| | |
|---|---|
| A | IgG1 CH1 |
| B | IgKappa constant |
| C/D | IgG1 CH3 |
| $E_1/F_1$ | IgG1 CH2 |
| $E_2/F_2$ | Linker sequence |
| $E_3$ | VLCD3 |
| $F_3$ | VHCD3 |
| $G_1/H_1$ | Linker |
| $G_2/H_2$ | scFvHer3 |
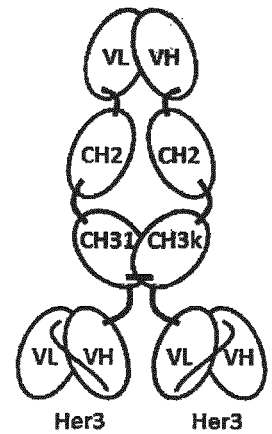
Genotypic Arrangement
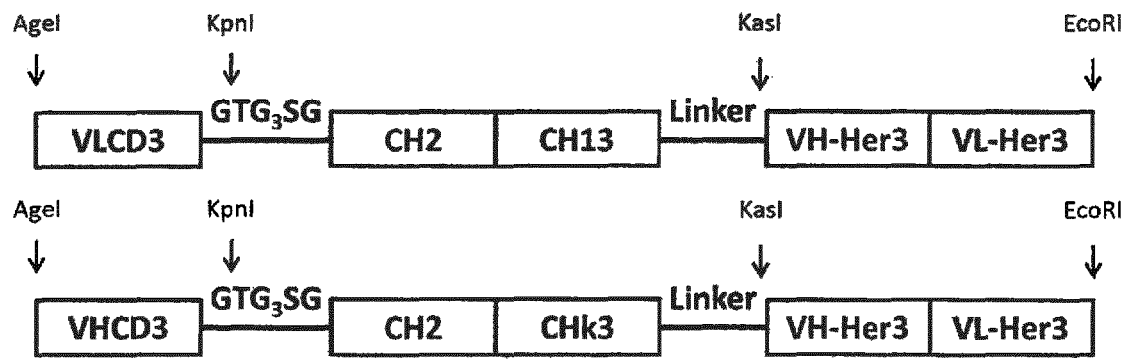

Figure 30
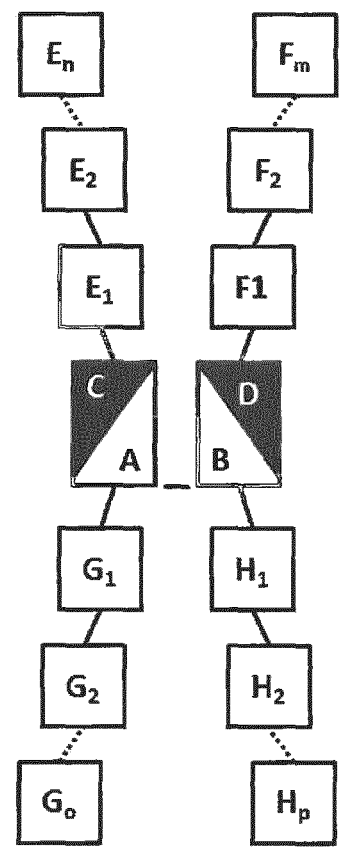
Example 12
$MCSP_N CD3_N$-hFc1k
| | |
|---|---|
| A | IgG1 CH1 |
| B | IgKappa constant |
| C/D | IgG1 CH3 |
| $E_1/F_1$ | IgG1 CH2 |
| $E_2/F_2$ | Hinge |
| $E_3$ | scFvMCSP |
| $F_3$ | scFvhuU3 |
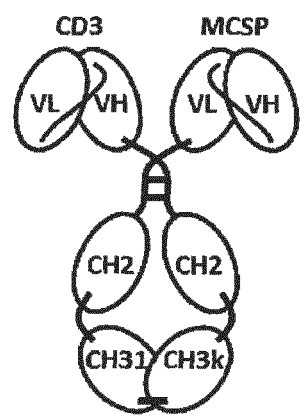

Figure 34

```
SEQ ID NO: 1, CH1 of IgG1
ASTKGPSVFPLAPSSKSTSGGTAALGCLVKDYFPEPVTVSWNSGALTSGVHTFPAVLQSSGLYSLSSVVTVPSSSLGTQTYICNVN
HKPSNTKVDKKVEPKSC

SEQ ID NO: 2, CH1 of IgG2
ASTKGPSVFPLAPCSRSTSESTAALGCLVKDYFPEPVTVSWNSGALTSGVHTFPAVLQSSGLYSLSSVVTVPSSNFGTQTYTCNVD
HKPSNTKVDKTVERK

SEQ ID NO: 3, CH1 of IgG3
ASTKGPSVFPLAPCSRSTSGGTAALGCLVKDYFPEPVTVSWNSGALTSGVHTFPAVLQSSGLYSLSSVVTVPSSSLGTQTYTCNVN
HKPSNTKVDKRVELKTP

SEQ ID NO: 4, CH1 of IgG4
ASTKGPSVFPLAPCSRSTSESTAALGCLVKDYFPEPVTVSWNSGALTSGVHTFPAVLQSSGLYSLSSVVTVPSSSLGTKTYTCNVD
HKPSNTKVDKRVESKYG

SEQ ID NO: 5, CH1 of IgA1
ASPTSPKVFPLSLCSTQPDGNVVIACLVQGFFPQEPLSVTWSESGQGVTARNFPPSQDASGDLYTTSSQLTLPATQCLAGKSVTCH
VKHYTNPSQDVTVPC

SEQ ID NO: 6, CH1 of IgA2
ASPTSPKVFPLSLDSTPQDGNVVVACLVQGFFPQEPLSVTWSESGQNVTARNFPPSQDASGDLYTTSSQLTLPATQCPDGKSVTCH
VKHYTNPSQDVTVPC

SEQ ID NO: 7, CH1 of IgD
APTKAPDVFPIISGCRHPKDNSPVVLACLITGYHPTSVTVTWYMGTQSQPQRTFPEIQRRDSYYMTSSQLSTPLQQWRQGEYKCVV
QHTASKSKKEIFRWPESP

SEQ ID NO: 8, CH1 of IgE
ASTQSPSVFPLTRCCKNIPSNATSVTLGCLATGYFPEPVMVTWDTGSLNGTTMTLPATTLTLSGHYATISLLTVSGAWAKQMFTCR
VAHTPSSTDWVDNKTFSVC

SEQ ID NO: 9, CH1 of IgM
GSASAPTLFPLVSCENSSPSSTVAVGCLAQDFLPDSITFSWKYKNNSDISSTRGFPSVLRGGKYAATSQVLLPSKDVMQGTDEHVV
CKVQHPNGNKEKDVPLPVVI

SEQ ID NO: 10, TCR α
PNIQNPDPAVYQLRDSKSSDKSVCLFTDFDSQTNVSQSKDSDVYITDKTVLDMRSMDFKSNSAVAWSNKSDFACANAFNNSIIPED
TFFPSPESSCD

SEQ ID NO: 11, TCR β2
DLKNVFPPEVAVFEPSEAEISHTQKATLVCLATGFYPDHVELSWWVNGKEVHSGVSTDPQPLKEQPALNDSRYCLSSRLRVSATFW
QNPRNHFRCQVQFYGLSENDEWTQDRAKPVTQIVSAEAWGRADC
```

Figure 34 (continued)

SEQ ID NO: 12, FcRn alpha 3
GKGNLEWKEPPSMRLKARPSSPGFSVLTCSAFSFYPPELQLRFLRNGLAAGTGQGDFGPNSDGSFHASSSLTVKSGDEHHYCCIVQ
HAGLAQPLRVEL SEQ ID NO: 13, β 2 micro globulin
IQRTPKIQVYSRHPAENGKSNFLNCYVSGFHPSDIEVDLLKNGERIEKVEHSDLSFSKDWSFYLLYYTEFTPTEKDEYACRVNHVT
LSQPKIVKWDRDM SEQ ID NO: 14, HLA-A
GKETLQRTDAPKTHMTHHAVSDHEATLRCWALSFYPAEITLTWQRDGEDQTQDTELVETRPAGDGTFQKWAAVVVPSGQEQRYTCH
VQHEGLPKPLTLRWE SEQ ID NO: 15, HLA-B α3
DIETLQRADPPKTHVTHHPISDHEATLRCWALGFYPAEITLTWQRDGEDQTQDTELVETRPAGDRTFQKWAAVVVPSGEEQRYTCH
VQHEGLPKPLTLRWEP SEQ ID NO: 16, HLA-D α2
GRIPVSRGFPIAEVFTLKPLEFGKPNTLVCFVSNLFPPMLTVNWHDHSVPVEGFGPTFVSAVDGLSFQAFSYLNFTPEPSDIFSCI
VTHEPDRYTAIAYWVPRNAL SEQ ID NO: 17, HLA-D β2
WGSLTNRTRPPSVQVAKTTPFNTREPVMLACYVWGFYPAEVTITWRKNGKLVMHSSAHKTAQPNGDWTYQTLSHLALTPSYGDTYT
CVVEHIGAPEPILRDWTPGLSP SEQ ID NO: 18, Igκ constant region
TVAAPSVFIFPPSDEQLKSGTASVVCLLNNFYPREAKVQWKVDNALQSGNSQESVTEQDSKDSTYSLSSTLTLSKADYEKHKVYAC
EVTHQGLSSPVTKSFNRGEC SEQ ID NO: 19, Igλ constant region
GQPKANPTVTLFPPSSEELQANKATLVCLISDFYPGAVTVAWKADGSPVKAGVETTKPSKQSNNKYAASSYLSLTPEQWKSHRSYS
CQVTHEGSTVEKTVAPTECS SEQ ID NO: 20: CH31, 1st CRI: CH1(IgG1), 2nd CRI: CH3(IgG1)
GQPREPSVFPLAPSSKSTSGGTAALGCLVKDYFPSDIAVEWESGALTSGVHTFPAVLQSSGLYSLSSVVTVPSSSLGTQTYSCSVM
HEALHNHYTQKSVEPKSC SEQ ID NO: 21: CH3κ, 3rd CRI: CLκ, 2nd CRI: CH3(IgG1)
GQPREPSVFIFPPSDEQLKSGTASVVCLVNNFYPRDIAVEWEVDNALQSGNSQESVTEQDSKDSTYSLSSTLTLSKADYEKHKVYS
CSVMHEALHNHYTQKSFNRGEC SEQ ID NO: 22: CH1H3, 1st CRI: CH1 (IgG1), 2nd CRI: CH3 (IgG1)
GQPREPSVFPLAPSSKSTSGGTAALGCLVKDYYPSDVAVEWNSGALTSGVHTFPAVLQSSGLYSLSSVVTVPSSSLGTQTYICNVM
HEALHNHKVDKKVEPKSC

Figure 34 (continued)

```
SEQ ID NO: 23: CLkH3, 3rd CRI: CLκ, 4th CRI: CH3 (IgG1)
GQPREPSVFIFPPSDEQLKSGTASVVCLLNNFYPSDAAVEWKVDNALQSGNSQESVTEQDSKDSTYSLSSTLTLSKADYEKHKVYA
CEVMHEALHNHPVTKSFNRGEC

SEQ ID NO: 24: b2mH3, 1st CRI: beta 2 microglobulin, 2nd CRI: CH3 (IgG1)
GQPREPKIQVYSRHPAENGKSNFLNCYVSGFYPSDIAVELLKNGERIEKVEHSDLSFSKDWSFYLLYYTEFTPTEKDEYACRVMHE
ALHNHPKIVKWDRDM SEQ ID NO: 25: FcRnH3, 3rd CRI: FcRn alpha 3 domain, 4th CRI: CH3 (IgG1)
GQPREPSMRLKARPSSPGFSVLTCSAFSFYPSDLALEFLRNGLAAGTGQGDFGPNSDGSFHASSSLTVKSGDEHHYCCIVMHEALH
NHPLRVEL SEQ ID NO: 26: TCRaH3, 1st CRI: TCR alpha chain constant domain, 2nd CRI: CH3 (IgG1)
GQPREPDPAVYQLRDSKSSDKSVCLFTDFYPSDVAQEKDSDVYITDKTVLDMRSMDFKSNSAVAWSNKSDFACANMFEALHNHIPE
DTFFPSPESSC SEQ ID NO: 27: TCRbH3, 3rd CRI: TCR beta chain constant domain, 4th CRI: CH3 (IgG1)
GQPREPEVAVFEPSEAEISHTQKATLVCLATGFYPSDVALEWWVNGKEVHSGVSTDPQPLKEQPALNDSRYCLSSRLRVSATFWQN
PRNHFRCQVMFEALHNHIVSAEAWGRADC SEQ ID NO: 28: TCRaH1, 1st CRI: TCR alpha chain constant domain, 2nd CRI: CH1 (IgG1)
ASTKGPDPAVYQLRDSKSSDKSVCLFTDFFPEPVSQSKDSDVYITDKTVLDMRSMDYKSNSAVAWSNKSDFACANAFKPSNTIPED
TFFPSPESSCD SEQ ID NO: 29: TCRaLk, 3rd CRI: TCR alpha chain constant domain, 4th CRI: CLκ
TVAAPDPAVYQLRDSKSSDKSVCLFTDFYPREVSQSKDSDVYITDKTVLDMRSMDYKSNSAVAWSNKSDFACANAFQGLSSIPEDT
FFPSPESSCD SEQ ID NO: 30: TCRaLL, 3rd CRI: TCR alpha chain constant domain, 4th CRI: CLλ
GQPKANPDPAVYQLRDSKSSDKSVCLFTDFYPGAVSQSKDSDVYITDKTVLDMRSMDYKSNSAVAWSNKSDFACANAFEGSIPEDT
FFPSPESSCD SEQ ID NO: 31: TCRbH1, 1st CRI: TCR beta chain constant domain, 2nd CRI: CH1 (IgG1)
ASTKGPEVAVFEPSEAEISHTQKATLVCLATGFFPEPVELSWWVNGKEVHSGVSTDPQPLKEQPALNDSRYCLSSRLRVSATFWQN
PRNHFRCQVQFKPSNTIVSAEAWGRADC SEQ ID NO: 32: TCRb1Lk, 3rd CRI: TCR beta chain constant domain, 4th CRI: CLk
TVAAPEVAVFEPSEAEISHTQKATLVCLATGFYPREVELSWWVNGKEVHSGVSTDPQPLKEQPALNDSRYCLSSRLRVSATFWQNP
RNHFRCQVQFQGLSSIVSAEAWGRADC SEQ ID NO: 33: TCRbLL, 3rd CRI: TCR beta chain constant domain, 4th CRI: CLλ
GQPKANPEVAVFEPSEAEISHTQKATLVCLATGFYPGAVELSWWVNGKEVHSGVSTDPQPLKEQPALNDSRYCLSSRLRVSATFWQ
NPRNHFRCQVQFEGSIVSAEAWGRADC
```

Figure 34 (continued)

```
SEQ ID NO: 34: VH13.7-CH2-CH3π
HVQLVQSGAEVKKPGSSVKVSCKASGYTFTDFYINWVRQAPGQGLEWIGEIVPSQGEAKYNDKFKARVTITADKSTSTAYMELSSL
RSEDTAVYYCARWDFLDYWGQGTTVTVSSGTGGGSGPSVFLFPPKPKDTLMISRTPEVTCVVVDVSHEDPEVKFNWYVDGVEVHNA
KTKPREEQYNSTYRVVSVLTVLHQDWLNGKEYKCKVSNKGLPSSIEKTISKAKGQPREPSVFPLAPSSKSTSGGTAALGCLVKDYF
PSDIAVEWESGALTSGVHTFPAVLQSSGLYSLSSVVTVPSSSLGTQTYSCSVMHEALHNHYTQKSVEPKSC

SEQ ID NO: 35: VL13.7-CH2-CH3κ
DVQMTQSPSSLSASVGDRVTITCRSSQSLLHSNGNTYLHWYQQKPGKAPKLLIYTVSNRFSGVPSRFSGSGSGTDFTLTISSLQPE
DFATYYCSQSTHVPYTFGGGTKVEIKGTGGGSGPSVFLFPPKPKDTLMISRTPEVTCVVVDVSHEDPEVKFNWYVDGVEVHNAKTK
PREEQYNSTYRVVSVLTVLHQDWLNGKEYKCKVSNKGLPSSIEKTISKAKGQPREPSVFIFPPSDEQLKSGTASVVCLVNNFYPRD
IAVEWEVDNALQSGNSQESVTEQDSKDSTYSLSSTLTLSKADYEKHKVYSCSVMHEALHNHYTQKSFNRGEC

SEQ ID NO: 36: scFv13.7-Hinge-CH2-CH3π
HVQLVQSGAEVKKPGSSVKVSCKASGYTFTDFYINWVRQAPGQGLEWIGEIVPSQGEAKYNDKFKARVTITADKSTSTAYMELSSL
RSEDTAVYYCARWDFLDYWGQGTTVTVSSGGGGSGGGGSGGGGSDVQMTQSPSSLSASVGDRVTITCRSSQSLLHSNGNTYLHWYQ
QKPGKAPKLLIYTVSNRFSGVPSRFSGSGSGTDFTLTISSLQPEDFATYYCSQSTHVPYTFGGGTKVEIKAAADKTHTCPPCPAPP
VAGPSVFLFPPKPKDTLMISRTPEVTCVVVDVSHEDPEVKFNWYVDGVEVHNAKTKPREEQYNSTYRVVSVLTVLHQDWLNGKEYK
CKVSNKGLPSSIEKTISKAKGQPREPSVFPLAPSSKSTSGGTAALGCLVKDYFPSDIAVEWESGALTSGVHTFPAVLQSSGLYSLS
SVVTVPSSSLGTQTYSCSVMHEALHNHYTQKSVEPKSC SEQ ID NO: 37: Hinge-CH2-CH3κ
DKTHTCPPCPAPPVAGPSVFLFPPKPKDTLMISRTPEVTCVVVDVSHEDPEVKFNWYVDGVEVHNAKTKPREEQYNSTYRVVSVLT
VLHQDWLNGKEYKCKVSNKGLPSSIEKTISKAKGQPREPSVFIFPPSDEQLKSGTASVVCLVNNFYPRDIAVEWEVDNALQSGNSQ
ESVTEQDSKDSTYSLSSTLTLSKADYEKHKVYSCSVMHEALHNHYTQKSFNRGEC SEQ ID NO: 38: scFvhuU3-Hinge-CH2-CH3κ
DIQMTQSPSSLSASVGDRVTITCRASQDIRNYLNWYQQKPGKAPKLLIYYTSRLHSGVPSRFSGSGSGTDFTFTISSLQPEDIATY
YCQQGNTLPWTFGQGTKLEIKRGGGGSGGGGSGGGGSQVQLVQSGAEVKKPGSSVKVSCKASGGTFSGYTMNWVRQAPGQGLEWMG
LINPYKGVSTYNGKFKDRVTITADKSTSTAYMELSSLRSEDTAVYYCARSGYYGDSDWYFDVWGQGTLVTVSSSGGGSGGGGSDKT
HTCPPCPAPPVAGPSVFLFPPKPKDTLMISRTPEVTCVVVDVSHEDPEVKFNWYVDGVEVHNAKTKPREEQYNSTYRVVSVLTVLH
QDWLNGKEYKCKVSNKGLPSSIEKTISKAKGQPREPSVFIFPPSDEQLKSGTASVVCLVNNFYPRDIAVEWEVDNALQSGNSQESV
TEQDSKDSTYSLSSTLTLSKADYEKHKVYSCSVMHEALHNHYTQKSFNRGECGGGGSGGGGSGGGGSGTGGSGG SEQ ID NO: 39: scFv3-43-Hinge-CH2-CH3π
QVQLQQSGPGLVKPSQTLSLTCAISGDSVSSNRAAWNWIRQSPSRGLEWLGRTYYRSKWYNDYAQSLKSRITINPDTPKNQFSLQL
NSVTPEDTAVYYCARDGQLGLDALDIWGQGTMVTVSSGGGGSGGGGSGGGGSQAGLTQPPAVSVAPGQTASITCGRDNIGSRSVHW
YQQKPGQAPVLVVYDDSDRPAGIPERFSGSNYENTATLTISRVEAGDEADYYCQVWGITSDHVVFGGGTKLTVLAAADKTHTCPPC
PAPPVAGPSVFLFPPKPKDTLMISRTPEVTCVVVDVSHEDPEVKFNWYVDGVEVHNAKTKPREEQYNSTYRVVSVLTVLHQDWLNG
KEYKCKVSNKGLPSSIEKTISKAKGQPREPSVFPLAPSSKSTSGGTAALGCLVKDYFPSDIAVEWESGALTSGVHTFPAVLQSSGL
YSLSSVVTVPSSSLGTQTYSCSVMHEALHNHYTQKSVEPKSC
```

Figure 34 (continued)

SEQ ID NO: 40: scFhuMCSP-Hinge-CH2-CH31
QVQLVQSGAEVKKPGASVKVSCKASGYTFTRSWMNWVRQAPGQGLEWMGRIYPGDGDTNYNGKFKGRVTMTRDTSTSTVYMELSSL
RSEDTAVYYCARGNTVVVPYTMDYWGQGTTVTVSSGGGGSGGGGSGGGGSDIQMTQSPSSLSASVGDRVTITCRASESVDSYGNSF
MHWYQQKPGKAPKLLIYLASNLESGVPSRFSGSGSGTDFTLTISSLQPEDFATYYCQQNNEDPLTFGGGTKVEIKRAAADKTHTCP
PCPAPPVAGPSVFLFPPKPKDTLMISRTPEVTCVVVDVSHEDPEVKFNWYVDGVEVHNAKTKPREEQYNSTYRVVSVLTVLHQDWL
NGKEYKCKVSNKGLPSSIEKTISKAKGQPREPSVFPLAPSSKSTSGGTAALGCLVKDYFPSDIAVEWESGALTSGVHTFPAVLQSS
GLYSLSSVVTVPSSSLGTQTYSCSVMHEALHNHYTQKSVEPKSC SEQ ID NO: 41: Amino acid sequence of VH13.7-CH2-CH3k
HVQLVQSGAEVKKPGSSVKVSCKASGYTFTDFYINWVRQAPGQGLEWIGEIVPSQGEAKYNDKFKARVTITADKSTSTAYMELSSL
RSEDTAVYYCARWDFLDYWGQGTTVTVSSGTGGGSGPSVFLFPPKPKDTLMISRTPEVTCVVVDVSHEDPEVKFNWYVDGVEVHNA
KTKPREEQYNSTYRVVSVLTVLHQDWLNGKEYKCKVSNKGLPSSIEKTISKAKGQPREPSVFIFPPSDEQLKSGTASVVCLVNNFY
PRDIAVEWEVDNALQSGNSQESVTEQDSKDSTYSLSSTLTLSKADYEKHKVYSCSVMHEALHNHYTQKSFNRGEC SEQ ID NO: 42: Amino acid sequence of VL13.7-CH2-CH31
DVQMTQSPSSLSASVGDRVTITCRSSQSLLHSNGNTYLHWYQQKPGKAPKLLIYTVSNRFSGVPSRFSGSGSGTDFTLTISSLQPE
DFATYYCSQSTHVPYTFGGGTKVEIKGTGGGSGPSVFLFPPKPKDTLMISRTPEVTCVVVDVSHEDPEVKFNWYVDGVEVHNAKTK
PREEQYNSTYRVVSVLTVLHQDWLNGKEYKCKVSNKGLPSSIEKTISKAKGQPREPSVFPLAPSSKSTSGGTAALGCLVKDYFPSD
IAVEWESGALTSGVHTFPAVLQSSGLYSLSSVVTVPSSSLGTQTYSCSVMHEALHNHYTQKSVEPKSC SEQ ID NO: 43: Amino acid sequence of VHCD3-CH2-CH3k-scFvHer3
QVQLVQSGAEVKKPGSSVKVSCKASGGTFSGYTMNWVRQAPGQGLEWMGLINPYKGVSTYNGKFKDRVTITADKSTSTAYMELSSL
RSEDTAVYYCARSGYYGDSDWYFDVWGQGTLVTVSSGTGGGSGPSVFLFPPKPKDTLMISRTPEVTCVVVDVSHEDPEVKFNWYVD
GVEVHNAKTKPREEQYNSTYRVVSVLTVLHQDWLNGKEYKCKVSNKGLPSSIEKTISKAKGQPREPSVFIFPPSDEQLKSGTASVV
CLVNNFYPRDIAVEWEVDNALQSGNSQESVTEQDSKDSTYSLSSTLTLSKADYEKHKVYSCSVMHEALHNHYTQKSFNRGECDKTH
TAPAPPVAGQVQLQQSGPGLVKPSQTLSLTCAISGDSVSSNRAAWNWIRQSPSRGLEWLGRTYYRSKWYNDYAQSLKSRITINPDT
PKNQFSLQLNSVTPEDTAVYYCARDGQLGLDALDIWGQGTMVTVSSGGGGSGGGGSGGGGSQAGLTQPPAVSVAPGQTASITCGRD
NIGSRSVHWYQQKPGQAPVLVVYDDSDRPAGIPERFSGSNYENTATLTISRVEAGDEADYYCQVWGITSDHVVFGGGTKLTVL SEQ ID NO: 44:Amino acid sequence of VLCD3-CH2-CH31-scFvHer3
DIQMTQSPSSLSASVGDRVTITCRASQDIRNYLNWYQQKPGKAPKLLIYYTSRLHSGVPSRFSGSGSGTDFTFTISSLQPEDIATY
YCQQGNTLPWTFGQGTKLEIKGTGGGSGPSVFLFPPKPKDTLMISRTPEVTCVVVDVSHEDPEVKFNWYVDGVEVHNAKTKPREEQ
YNSTYRVVSVLTVLHQDWLNGKEYKCKVSNKGLPSSIEKTISKAKGQPREPSVFPLAPSSKSTSGGTAALGCLVKDYFPSDIAVEW
ESGALTSGVHTFPAVLQSSGLYSLSSVVTVPSSSLGTQTYSCSVMHEALHNHYTQKSVEPKSCDKTHTAPAPPVAGQVQLQQSGPG
LVKPSQTLSLTCAISGDSVSSNRAAWNWIRQSPSRGLEWLGRTYYRSKWYNDYAQSLKSRITINPDTPKNQFSLQLNSVTPEDTAV
YYCARDGQLGLDALDIWGQGTMVTVSSGGGGSGGGGSGGGGSQAGLTQPPAVSVAPGQTASITCGRDNIGSRSVHWYQQKPGQAPV
LVVYDDSDRPAGIPERFSGSNYENTATLTISRVEAGDEADYYCQVWGITSDHVVFGGGTKLTVL SEQ ID NO: 45; Amino acid sequence of IgG1 CH3
GQPREPQVYTLPPSRDELTKNQVSLTCLVKGFYPSDIAVEWESNGQPENNYKTTPPVLDSDGSFFLYSKLTVDKSRWQQGNVFSCS
VMHEALHNHYTQKSLSLSPGK SEQ ID NO: 46; Amino acid sequence of IgG2 CH3
GQPREPQVYTLPPSREEMTKNQVSLTCLVKGFYPSDIAVEWESNGQPENNYKTTPPMLDSDGSFFLYSKLTVDKSRWQQGNVFSCS
VMHEALHNHYTQKSLSLSPGK

Figure 34 (continued)

```
SEQ ID NO: 47; Amino acid sequence of IgG3 CH3
GQPREPQVYTLPPSREEMTKNQVSLTCLVKGFYPSDIAVEWESSGQPENNYNTTPPMLDSDGSFFLYSKLTVDKSRWQQGNIFSCS
VMHEALHNRFTQKSLSLSPGK SEQ ID NO: 48; Amino acid sequence of IgG4 CH3
GQPREPQVYTLPPSQEEMTKNQVSLTCLVKGFYPSDIAVEWESNGQPENNYKTTPPVLDSDGSFFLYSRLTVDKSRWQEGNVFSCS
VMHEALHNHYTQKSLSLSLGK SEQ ID NO: 49; Amino acid sequence of IgM CH4
VALHRPDVYLLPPAREQLNLRESATITCLVTGFSPADVFVQWMQRGQPLSPEKYVTSAPMPEPQAPGRYFAHSILTVSEEEWNTGE
TYTCVVAHEALPNRVTERTVDKSTGK SEQ ID NO: 50; Amino acid sequence of IgA1 CH3
GNTFRPEVHLLPPPSEELALNELVTLTCLARGFSPKDVLVRWLQGSQELPREKYLTWASRQEPSQGTTTFAVTSILRVAAEDWKKG
DTFSCMVGHEALPLAFTQKTIDRLAGK SEQ ID NO: 51; Amino acid sequence of IgA2 CH3
GNTFRPEVHLLPPPSEELALNELVTLTCLARGFSPKDVLVRWLQGSQELPREKYLTWASRQEPSQGTTTFAVTSILRVAAEDWKKG
DTFSCMVGHEALPLAFTQKTIDRLAGK SEQ ID NO: 52; Amino acid sequence of IgD CH3
VPAQAPVKLSLNLLASSDPPEAASWLLCEVSGFSPPNILLMWLEDQREVNTSGFAPARPPPQPGSTTFWAWSVLRVPAPPSPQPAT
YTCVVSHEDSRTLLNASRSLEVSYVT SEQ ID NO: 53; Amino acid sequence of IgE CH4
GPRAAPEVYAFATPEWPGSRDKRTLACLIQNFMPEDISVQWLHNEVQLPDARHSTTQPRKTKGSGFFVFSRLEVTRAEWEQKDEFI
CRAVHEAASPSQTVQRAVSVNPGK SEQ ID NO: 54, Igλ constant region
GQPKAAPSVTLFPPSSEELQANKATLVCLISDFYPGAVTVAWKADSSPVKAGVETTTPSKQSNNKYAASSYLSLTPEQWKSHRSYS
CQVTHEGSTVEKTVAPTECS SEQ ID NO: 55, Igλ constant region
GQPKAAPSVTLFPPSSEELQANKATLVCLISDFYPGAVTVAWKADSSPAKAGVETTTPSKQSNNKYAASSYLSLTPEQWKSHKSYS
CQVTHEGSTVEKTVAPTECS SEQ ID NO: 56, Igλ constant region
GQPKAAPSVTLFPPSSEELQANKATLVCLISDFYPGAVKVAWKADGSPVNTGVETTTPSKQSNNKYAASSYLSLTPEQWKSHRSYS
CQVTHEGSTVEKTVAPAECS SEQ ID NO: 57, Igλ constant region
GQPKAAPSVTLFPPSSEELQANKATLVCLVSDFYPGAVTVAWKADGSPVKVGVETTKPSKQSNNKYAASSYLSLTPEQWKSHRSYS
CRVTHEGSTVEKTVAPAECS
```

Figure 34 (continued)

```
SEQ ID NO: 58, TCR β1
EDLNKVFPPEVAVFEPSEAEISHTQKATLVCLATGFFPDHVELSWWVNGKEVHSGVSTDPQPLKEQPALNDSRYCLSSRLRVSATF
WQNPRNHFRCQVQFYGLSENDEWTQDRAKPVTQIVSAEAWGRADC

SEQ ID NO: 59, HLA-D β2
WGSLTNRTRPPSVQVAKTTPFNTREPVMLACYVWGFYPAEVTITWRKNGKLVMHSSAHKTAQPNGDWTYQTLSHLALTPSYGDTYT
CVVEHIGAPEPILRDWTPGLSPMQTLK
```

Figure 38
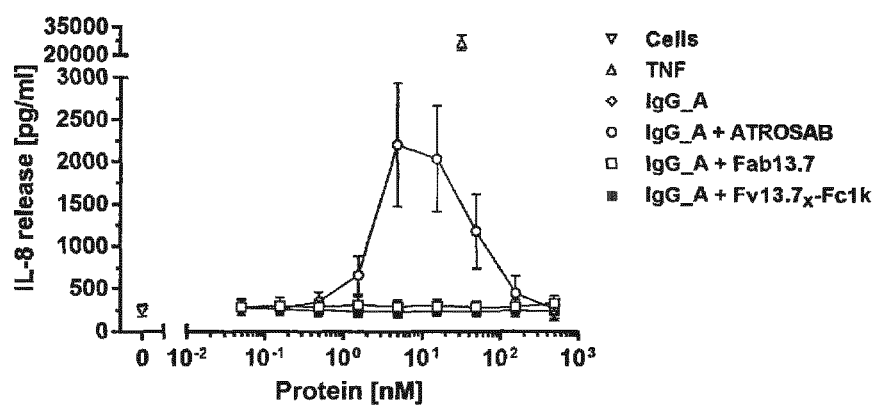
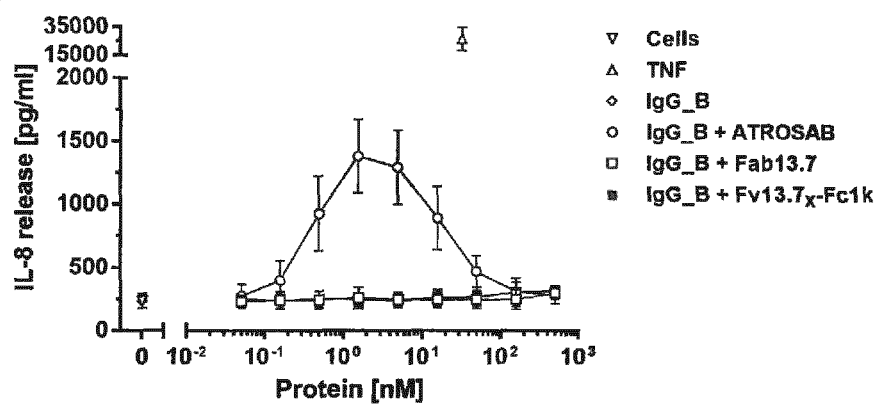
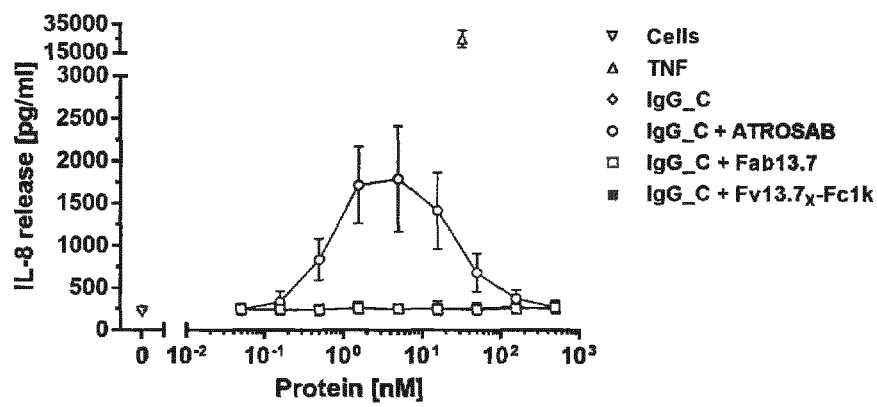

HETERODIMERIZING IG DOMAINS

CROSS-REFERENCE TO RELATED APPLICATION

This application is a U.S. national phase of International Application No. PCT/EP2018/064538, filed on Jun. 1, 2018, which claims priority to European Patent Application No. 17174087.1, filed Jun. 1, 2017, both of which are incorporated by reference herein in their entirety.

The present invention provides a protein complex comprising heterodimerizing regions HRI and HRII, each comprised of antiparallel 3-strands and intervening regions wherein HRI and HRII are each interspersed fusion proteins of two human constant regions of an immunoglobulin or immunoglobulin-like proteins. The present invention also provides nucleic acid molecules comprising a sequence encoding said protein complexes and vectors comprising the nucleic acid. The present invention also provides the protein complex, the nucleic acid and the vector for use as a medicament. The present invention further provides a method of determining the amino acid sequence of HRI and/or of the amino acid sequence of HRII. The present invention also provides a method of producing amino acid chains of HRI and/or amino acid chains of HRII. The present invention further provides the protein complex for use in the prophylaxis, treatment or diagnosis of a disorder or a disease.

BACKGROUND

Bispecific antibodies find increasing interest for diagnostic and therapeutic applications. A comprehensive review is provided in Kontermann RE and Brinkmann U (2015) Drug Discovery Today; 20(7): 883 and references cited therein. While natural antibodies are monospecific, bispecific antibodies recognize two different epitopes either on the same or on different antigens. Applications of bispecific antibodies cover a broad spectrum from diagnosis, imaging and therapy. Initially, therapeutic applications focused mainly on effector cell retargeting for cancer therapy, including T-cells, which cannot be recruited to tumor cells by normal antibodies. However, during the past decade many other therapeutic strategies based on bispecific antibodies have been established, including besides retargeting of effector molecules, cells and genetic vehicles, also dual targeting strategies, half-life extension, and delivery through blood-brain barrier. Indications include cancer, chronic inflammatory diseases, autoimmunity, bleeding disorders, and infections.

Bispecific antibodies with defined specificities are artificial molecules, per se not found in nature. They have, therefore, to be generated by molecular or genetic means. The generation of bispecific IgG molecules faces two major problems due to the fact that the antigen-binding sites are built by the variable domains of the light and heavy chain (VL, VH). Firstly, a bispecific antibody requires two different heavy chains, and secondly, it requires also two different light chains. Bispecific IgG antibodies, thus exhibit asymmetry due to the presence of, at least, two different variable domain (Fv) regions. Promiscuous pairing of heavy and light chains of two antibodies expressed in one cell can theoretically result in 10 different combinations, with only one being bispecific and the remaining pairings resulting in non-functional or monospecific molecules (Schaefer et al., 2016). To direct and to force correct assembly of correct binding sites, i.e. heavy and light chains, is one of the challenges of generating bispecific antibodies.

Genetic engineering to force heterodimerization of heavy chains, described in the following section, targets one of the problems of bispecific IgG formation. Although, heterodimeric heavy chains can still assemble with two different light chains resulting in four possible combinations, one bispecific molecule, one non-functional combination, and two monospecific molecules, it reduces the possible combinations from 10 different molecules to 4 combinations. Heavy chain pairing is mediated by the last domain of the constant region, i.e. CH3 in IgG molecules, which forms high affinity homodimer complexes. Further interactions reside in the hinge region responsible for covalent linkage of two heavy chains, which form after heavy chain assembly.

Various strategies use either steric or electrostatic steering effects, or combination thereof, to generate a complementary interface favouring heterodimerization over homodimerization.

Ridgway and coworkers generated a CH3 interface favouring heterodimeric assembly by replacing on one CH3 interface small side chains with larger ones to generate a knob, and replacing on the other CH3 domain large side chains with smaller ones to generate a hole (Ridgway et al., 1996). Testing various variants demonstrated a preferential heterodimerization with substitution T366Y in one chain and Y407T on the other chain. These original knobs-into-holes mutations were, for example, used to produce an IgG directed against HER2 and IGF-1R. The knobs-into-holes approach was subsequently extended identifying further suitable combinations by phage display. These mutations were then used to generate bispecific IgG antibodies testing additional substitutions to allow for disulfide bond formation. One variant showed >95% heterodimer formation (S354C, T366W/Y349C, T366S, L368A, Y407V). This heterodimeric heavy chain was then applied to construct a bispecific antibody against Mlp and HER3 from a single-chain variable fragment (scFv) using an identical VL domain, thus expressing a common light chain (Merchant et al., 1998). The heteromeric heavy chains produced functional bispecific antibodies, allowed purification by protein A chromatography and retained Fc-mediated effector functions, such as ADCC. This approach was adopted to generate various bispecific antibodies and, nowadays, forms a versatile basis of producing bispecific IgG molecules, and derivatives thereof, including trivalent Ig-like antibodies, and bispecific Fc and CH3 fusion proteins.

One example is T-cell retargeting bispecific antibodies. To avoid systemic activation of T cells through bivalent binding to CD3, molecules were designed exhibiting only one binding site for CD3. This includes, scFv-Fc(kih), with one scFv on each Fc chain, and tandem-scFv-Fc(kih) (BiTE-KIH) with the tandem scFv fused to one of the Fc chain (Xu et al., 2015). In this study, the CD3 binding moiety was either fused to the knob or the hole-containing Fc chain (KIH, KIH'), respectively. Interestingly, the BiTE-KIHr outperformed the BiTE-KIH in terms of expression titers. However, no differences were observed regarding T-cell activation and tumor cell lysis. In a similar approach an Fc-KIH was used to generate bivalent, bispecific scFv-Fc fusion proteins directed against CD16 and HER2 for the retargeting of NK cells to tumor cells (Xie et al., 2005).

Monovalent binding can also be essential for antibodies targeting cell surface receptors, such as c-MET, in order to avoid receptor cross-linking and activation. Bispecific antibodies binding monovalently to cell surface receptors, with application for dual targeting and neutralization of two different receptors, were generated by fusing a Fab arm to the N-terminus of an Fc-hole chain and a disulfide-stabilized scFv to the C-terminus of the same Fc chain, and co-expression with an unfused Fc-knob.

Fusion of a VH domain to the C-terminus of one Fc (kih) chain and the VL domain either expressed separately or fused to the C-terminus of the other, resulted in a bispecific, trivalent IgG-Fv (mAb-Fv) fusion protein, with the Fv fragment stabilized by a interdomain disulfide bond (Metz et al., 2012). Flexibility of the Fv fragment in the IgG-Fv fusion could be increased by introducing a proteolytic cleavage site, e.g. for furin or MMP, in the linker connecting the VL domain with the Fc chain. After cleavage, this resulted in a bispecific molecule with the C-terminal Fv fragment connected only through the VH domain to the IgG. Similarly, a scFv-Fc-Fv fusion protein was generated exhibiting two binding sites for EGFR (scFv fused to the N-terminus of the Fc chain) and one for LPS (VH fused to the C-terminus of the Fc (knob) and VL fused to the C-terminus of Fc (hole)). Further derivatives of bispecific IgG (kih) antibodies include TriMAbs. Here, one or two disulfide-stabilized scFvs are fused to one or both Fc (kih) chains resulting in trispecific, trivalent or tetravalent antibodies, respectively. This was shown for TriMAbs targeting EGFR, IGF-1R and either cMet or HER3. In this approach, the Fab fragment was composed of a single-chain Fab fragment with disulfide-stabilized Fv domains.

Recently, the knobs-into-holes strategy was expanded to other IgG isotypes to generate IgG4 heterodimers, which are per se deficient in Fc©-mediated effector functions, e.g. to produce bispecific antibodies directed against IL-4 and IL-13.

Using structure- and sequence-based approaches to explore energies of paired variant combinations at the interface across the CH3 dimer, yielded a HA-TF variant (S364H, F405A/Y349T, 394F) which showed approximately 83% heterodimer formation in the context of a bispecific mAb-Fv (IgG-Fv) molecule, developed for co-targeting of HER2 (bivalent binding) and CD3 (monovalent binding). Further examples using this CH3 heterodimerization module include mono- and bivalent scFv-Fc fusion proteins.

Another rational structure-guided approach resulted in a set of mutations that were reported to have a high thermal stability and to form pure heterodimers with no detectable homodimers. The Fc design (ZW1) included T350V, L351Y, F405A, and Y407V substitutions in the first Fc chain and T350V, T366L, K392L, and T394W substitutions in the second Fc chain.

While the strategies described above mainly depend on hydrophobic interactions, other approaches utilize electrostatic interactions (steering) to avoid homodimerization of CH3 domains by electrostatic repulsion and to direct heterodimerization by electrostatic attraction. In the wild-type CH3 domains two charge interactions between K409 and D399 are found at the CH3-CH3 interface. Substituting in one CH3 domain K409 by an aspartate and in the other CH3 domain D399 by a lysine was found to favour formation of CH3 heterodimers. Further substitutions, e.g. K392D in one chain and E356K in the other chain, were introduced. Introduction of further charged pairs impaired productivity. This approach, using two charge pair substitutions (K409D, K392D/D399K, E356K; CH3 charge pairs) was applied to generate a bispecific scFv-Fc fusion protein directed against CD3 and TARTK and more recently to generate bispecific IgGs directed against EGFR and HER2 or sclerostin and DKK-1. This included the introduction of new charge pairs into the Fab arms to direct correct light chain pairing.

Electrostatic steering effects are also used in Biclonics, bispecific antibodies utilizing a common light chain and heterodimerizing heavy chains (Geuijen et al., 2014). Here, residues in one CH3 (366, 366+351) are substituted by a positively charge lysine residue, and one or more residues in the second CH3 (e.g. 349, 351, 355, 368) are substituted by negatively charged glutamic acid or aspartic acid residues. One bispecific antibody based on this technology (MCLA-128) directed against HER2 and HER3 is currently in a clinical phase I/II trial.

Preferential heavy chain heterodimerization has also been achieved introducing charge pairs into the hinge region of IgG1 and IgG2. For IgG, these hinge substitutions comprise D221E, P228E in the first hinge and D221R and P228R in the second hinge. For IgG2, substitutions comprise C223E and P228E in one hinge region and C223R, E225R, P228R in the other hinge region. Here, E225R is able to form an electrostatic interaction with a naturally occurring glutamic acid at position 225, thus only two substitutions are required in the first IgG2 hinge. These mutations were combined with L368E and K409R, respectively, to force heterodimeric assembly in the CH3 domains. Applicability was shown for anti-EGFR x anti-HER2 bispecific IgG antibodies as well as for an anti-CE x anti-CD20 antibody, utilizing separate expression of the two antibodies and subsequent assembly from half antibodies.

In another study, mutations favouring heterodimeric assembly of CH3 domains were identified by, firstly, substituting charged residues around the rim of the preserved hydrophobic core (L351, T366, L368, Y407) with larger or smaller hydrophobic amino acids to replace the symmetric electrostatic interactions with asymmetric hydrophobic ones, and, secondly, substituting amino acids weakly involved in interaction with amino acids carrying charged, long side chains to form asymmetric long-range electrostatic interactions. This resulted in a final combination of K360E, K409W in one CH3 with Q347R, D399V, F405T in the other CH3 (EW-RVT). Functionality was demonstrated for a bispecific scFv-Fc heterodimer targeting VEGFR-2 and Met. Introducing a disulfide bond into the CH3 domain (Y349C in the first domain and S354C in the second domain) increased heterodimer formation and thermodynamic stability. Furthermore, using yeast surface-displayed combinatorial Fc libraries variants carrying different mutations and exhibiting high heterodimerization yields (80-90%) were selected.

Based on the observation that IgG4 antibodies are able to exchange their Fab arms, a dynamic process involves separation of the two heavy chains and reassembly into full IgG4. This process was attributed to IgG4 core hinge sequences in conjugation with residues in the CH3 domain. This natural process of Fab arm exchange in IgG4 was adapted to generate bispecific IgG1 molecules by controlled Fab arm exchange (cFAE). A screening of mutations in the CH3 domain allowing cFAE in the context of a K409R mutation in a corresponding CH3 resulted in the identification of mutation F405L, which allowed efficient exchange of half antibodies of separately expressed antibodies after mixing and mild reduction with ®-mercaptoethanol. Scalability of this process was demonstrated for an anti-EGFR x anti-CD20 bispecific IgG (DuoBody) resulting in >95% bispecific molecules.

Complementarity in the CH3 interface allowing for a heterodimeric assembly of Fc chains was developed by designing strand-exchange engineered domain (SEED) heterodimers. These SEED CH3 domains are composed of alternating segments derived from human IgA and IgG CH3 sequences (AG SEED CH3 and GA SEED CH3) and were used to generate so-called SEEDbodies (Davis et al., 2010). Because molecular models suggested that interaction with neonatal Fc receptor (FcRn) is impaired in the AG SEED CH3, residues at the CH2-CH3 junction were returned to IgG sequences. Pharmacokinetic studies confirmed the long half-life of SEEDbodies comparable to other Fc fusion proteins and IgG1 (Muda et al., 2011). One example of SEEDbodies is the generation of a bispecific Fab-scFv-Fc fusion protein targeting two different epitopes on EGFR. This biparatopic antibody demonstrated enhanced activity, similar to the combination of the two parental antibodies.

A further CH3 heterodimerizing interface was generated by mimicking the natural association of the T cell receptor α and β chains. This BEAT technology (Bispecific Engagement by Antibodies based on the T cell receptor) was applied to generate a Fab/scFv-Fc fusion protein) to avoid light chain mispairing. This approach was used to generate a bispecific antibody directed against CD3 and HER2 for T cell retargeting.

Leaver-Fay and coworkers (Leaver-Fay et al., 2016) applied a multistage design (MSD), an approach which designs for multiple protein stages simultaneously, to generate a set of CH3 mutations at the Fc interface. Two sets (7.8.60 and 20.8.34) were used to generate bispecific IgGs derived from pertuzumab (anti-HER2), matuzumab (anti-EGFR), BHA10 (anti-LT®R), and MetMAb (anti-cMet), in combination with orthogonal Fab interface mutations, yielding in all cases at least 93% ofbispecific antibodies.

Heterodimeric assembly of heavy chains can be also achieved by using a separate heterodimerization module, which is subsequently removed from the bispecific antibody. This strategy was applied employing a leucine zipper structure derived from Acid.p 1 (Ap 1) and Base.p 1 (Bp1) peptides fused to the C-terminus of the two heavy chains. This LUZ-Y platform was used to generate monovalent Fab-Fc fusion proteins but also bispecific IgGs based on a common light chain or scFab arms directed against EGFR and HER3. The introduction of a proteolytic cleavage site between the C-terminus of the Fc chain and the leucine zipper sequences allows to remove the leucine zipper yielding bispecific IgG antibody with a natural composition.

While the use of modifications to force heterodimerization of Fc regions targets the heavy chain problem, these approaches still suffer from the light chain problem. Thus, using two different light chains still allows the generation of four different combinations, with only one being bispecific. Approaches have, therefore, being developed to target correct pairing of cognate heavy and light chains in combination with Fc-modified heavy chains.

The first approach described was the use of a common light chain (Merchant et al., 1998). This was based on the observation that antibodies isolated from phage display libraries against diverse antigens often use the same VL domain, reflecting the very limited size of the L chain repertoire in the phage library. In combination with the knobs-into-holes modification of the heavy chain, bispecific IgG molecules, e.g. directed against HER3 and Mpl were generated. Various bispecific IgGs with a common light chain have subsequently being produced using e.g. the knobs-into-holes modification but also other Fc modifications.

Several of the Fc-modifications described above utilized scFv fragments fused to the Fc chains to generate bispecific antibodies in order to circumvent the light chain problem. Based on the finding that Fab fragments can be expressed as single-chain derivative (scFab to connect the C-terminus of the light chain with the N-terminus of the VH domain), full IgG molecules were generated by the expression of a single polypeptide comprising a light chain connected to a heavy chain. Linker with a lengths of 30 residues, e.g. $(G_4S)_6$), to 38 residues have been utilized, including deletions of the connecting disulfide bond between CH1 and CL. An improved scFab platform was described for disulfide-linked scFab molecules using a linker of 60 flexible residues. A $G_4S_6$ linker was applied to generate a bispecific Fab-Fc fusion protein combined with knobs-into-holes mutations in the Fc region, which was further modified through C-terminal fusion of scFv fragments to obtain trispecific, trivalent and tetravalent molecules, examplified for targeting EGFR, IGF-1R, and either cMet or HER3. The scFab format was also combined with LUZ-Y Fc heterodmerization strategy. Here, proteolytic cleavage sites were introduced into the Fab linker to allow removal of the linkers from the correctly assembled bispecific IgG molecules. Furthermore, scFab were combined with unmodified Fab fragments to generate bispecific Fab-scFab-Fc fusion proteins in combination with Fc(kih) (OAscFab-IgG format), as shown for a bispecific IgG targeting EGFR and IGF-1R, which could be expressed at high yields.

A different approach is applied by the CrossMab technology. Here, in the context of knobs-into-holes heavy chains, either the light chain of one Fab arm is exchanged by the Fd fragment of the corresponding heavy chain (CrossMab$^{Fab}$), or only one pair of the variable (CrossMab$^{VH-VL}$) or constant domain (CrossMab$^{CH1-CL}$) of one Fab is swapped between the light and heavy chain. This results in pairing of the unmodified light chain with the corresponding unmodified heavy chain and pairing of the modified light chain with the corresponding modified heavy chain. Exemplified for a bispecific CrossMab directed against VEGF and Ang-2, simultaneous antigen binding with unaltered affinity was demonstrated, with the CrossMab$^{CH1-CL}$ showing a superior side-product profile. In a subsequent study, this antibody (A2V) showed to be able to reprogram tumor-associated macrophages leading to a prolonged survival in a number of extracranial tumor models. The antibody (RG7716) is currently in clinical development. In a recent study, the CrossMab$^{CH1-CL}$ format was applied to generate bispecific antibodies directed against the HIV Env protein and CD4/CCR5 for virus neutralization. Here, heterogeneity was observed in the original CrossMabs, due to incorrect pairing of the unmodified light chain, which could be improved by introducing additional mutations into this chain. The CrossMab approach has being developed into a versatile platform technology, allowing not only to generate bivalent, bispecific IgG molecules, but also tri- and tetravalent, bispecific IgG fusion proteins, e.g. by fusing an additional Fab fragment to the N-terminus one of the knobs-into-holes heavy chains, or two CrossMab Fab arms to the C-terminus of homodimerizing heavy chains, with many other formats enabled by the CrossMab technology, including bispecific, trivalent and tetravalent IgG-Fab fusion proteins, e.g. to generate bispecific molecules with one binding site for CD3 and two for a tumor-associated antigen. The concept was further evolved to generate tetravalent, tetraspecific four-in-one antibodies by applying a knobs-into-holes Fc region and the CrossMab technology to two-in-one Fab arms (see below).

Another approach to the light chain problem is the genetic engineering of the light and heavy chain interface to generate an orthogonal interface that allows a light chain to interact with higher affinity with its cognate heavy chain. Here, the interaction between the variable domains (VH-VL pair) and the first constant domains (CH1-CL) is modified. Testing various modifications identified by a multistage design application, a set of mutations was established which favors pairing of the orthogonal Fab fragments. These modification were applied to generate various bispecific IgG molecules, e.g. directed against EGFR x cMET, EGFR x HER2, Axl x cMet, and EGFR x LTβR, or against two epitopes on HER2 by combining the binding site of trastuzumab with that of pertuzumab. Here, Fc heterodimerization was pursued through electrostatic steering effects introduced into the CH3 domain (Gunasekaran et al., 2010). For example, a bispecific antibody with orthogonal Fab arms based on pertuzumab (anti-HER2) and matuzumab (anti-EGFR), both with a lambda light chain, was generated by substituting Q39K, R62E, H172A, F174G in the heavy chain and D1R, Q38R, L135Y, S176W in the light chain of pertuzumab (VRD1CRD2 modifications) combined with Q39Y in the heavy chain and Q38R in the light chain of matuzumab (VRD2 modifications), yielding 90% correct light chain assembly.

A further attempt to direct light chain pairing with its cognate heavy chain Fc fragment, was to substitute the CH1 and CL domains of one Fab arm with the Cα and Cβ domains from the T-cell receptor (TCR). This was applied to generate either a Fab-IgG molecule with the Fab arm fused with a (G$_4$S)$_5$ linker to the N-terminus of the heavy chain, or an IgG-Fab molecule with the Fab arm fused with a (G$_4$S)$_4$ linker to the C-terminus of the heavy chain, exemplified for bispecific antibodies derived from trastuzumab and pertuzumab. However, probably due to strong VH/VL interactions of the trastuzumab binding site, only a small fraction showed correct Fab arm pairings. This was improved to some extend by introducing an additional mutation in the VL domains (Y36F) to weaken the VH-VL interaction as well as introducing a charge-charge interaction between the VL and VH domains (VL Q38D, VH Q39K) in the trastuzumab Fv.

However, although there exist a number of approaches to direct heterodimerization of multispecific antibodies, these molecules are artificial. Especially immunogenicity remains an important issue to be resolved. Furthermore, the degree of heterodimerization is often non-satisfying and thermal stability and biophysical properties, e.g. half-life, are often not as expected.

To overcome the disadvantages in the prior art, the present inventors further investigated the generation of Ig domains which assemble into heterodimers, which can be used as building blocks to generate molecules with one, two or more specificity and valencies. A key feature is that these heterodimeric pairs are composed solely of human sequences and, these pairs provide a fully natural heterodimerization interface without any introduced mutations, hence minimizing the propensity to induce an immune response. In addition, the heterodimerizing Ig domains can be connected by a disulfide linkage, which is formed between cysteine residues, contained within the naturally occurring sequences and are presented in their evolutionary developed and hence optimal conformation. Moreover these domains can be further equipped with the ability to interact with e.g. the FcRn or with neighbouring Ig domains like CH2 or variable domains, which provide further advantageous properties to the heterodimerizing domains. Surprisingly, it was found that terminal half-life of the generated bivalent format could be improved and bioavailability was increased. Furthermore, these heterodimerizing Ig building blocks were used to generate bi- or tri-valent and bispecific scFv-Fc fusion proteins to retarget CD3 expressing T-cells to FAP (fibroblast activation protein) or Her3 expressing tumor cells or to tumor cells that are surrounded by FAP-expressing fibroblasts.

SUMMARY OF THE INVENTION

The underlying principle of the present invention is the generation of novel heterodimerizing regions or heterodimerizing protein domains (HRI and HRII) that can be comprised in two or more proteins of a protein complex, wherein the constant immunoglobulin domains are naturally heterodimerizing (1$^{st}$ and 3$^{rd}$ CRI) and which are modified to provide HRI and HRII with additional properties. These properties are transferred from one or more further constant immunoglobulin domains (2$^{nd}$ and 4$^{th}$ CRI) that are different from the 1$^{st}$ and 3$^{rd}$ CRI to the heterodimerizing constant immunoglobulin domains (1$^{st}$ and 3$^{rd}$ CRI) by replacement of amino acids of the heterodimerizing constant immunoglobulin domains (1$^{st}$ and 3$^{rd}$ CRI) with amino acids of the alternative constant immunoglobulin domains (2$^{nd}$ and 4$^{th}$ CRI). These properties are e.g. the interaction with the neonatal Fc receptor (FcRn) or the interaction with N- or C-terminally connected protein domains (e.g. further constant immunoglobulin domains, which are not 1$^{st}$, 2$^{nd}$, 3$^{rd}$ or 4$^{th}$ CRI).

Thus, in a first aspect the present invention provides a protein complex comprising at least two amino acid chains I and II, which are non-covalently bound to each other through a heterodimerization region I (HRI) comprised in amino acid chain I and a heterodimerization region II (HRII) comprised in amino acid chain II and wherein HRI and HRII respectively comprise the heterodimerizing domains of a human constant region of an immunoglobulin or an immunoglobulin-like protein wherein each heterodimerizing domain is modified in that amino acid sequences of a further immunoglobulin or an immunoglobulin-like protein are inserted into at least two preferably at least three regions of the respective heterodimerizing domain that are outside the heterodimerization interphase of the respective HRI and HRII, i.e. which are preferably solvent accessible after heterodimerization of HRI and HRII.

More specifically the protein complex of the invention comprises at least two amino acid chains I and II, which are non-covalently bound to each other through a heterodimerization region I (HRI) comprised in amino acid chain I and a heterodimerization region II (HRII) comprised in amino acid chain II, wherein (a) HRI comprises seven antiparallel beta strands AI, BI, CI, DI, EI, FI, and GI, six intervening regions bI, cI, dI, eI, fI, and gI, a N-terminal region aI and a C-terminal region hI positioned from N- to C-terminus in the following order:

aI-AI-bI-BI-cI-CI-dI-DI-eI-EI-fI-FI-gI-GI-hI, wherein HRI is a fusion protein of a first human constant region of an immunoglobulin or immunoglobulin-like protein (1$^{st}$ CRI, acceptor) interspersed with amino acids of a second human constant region of an immunoglobulin or immunoglobulin-like protein (2$^{nd}$ CRI, donor), wherein the 1$^{st}$ CRI comprises seven antiparallel beta strands A1, B1, C1, D1, E1, F1, and G1, six intervening regions b1, c1, d1, e1, f1, and g1, a N-terminal region a1 and a C-terminal region h1 arranged from N- to C-terminus in the following order:

a1-A1-b1-B1-c1-C1-d1-D1-e1-E1-f1-F1-g1-G1-h1, wherein the 2$^{nd}$ CRI comprises seven antiparallel beta strands A2, B2, C2, D2, E2, F2, and G2, six intervening regions b2, c2, d2, e2, f2, and g2, a N-terminal region a2 and a C-terminal region h2 positioned from N- to C-terminus in the following order:

a2-A2-b2-B2-c2-C2-d2-D2-e2-E2-f2-F2-g2-G2-h2, wherein HRI has the amino acid sequence of the $1^{st}$ CRI and wherein at least the following amino acids of the $1^{st}$ CRI are replaced with the following amino acids of the $2^{nd}$ CRI:

(i) at least 1 amino acid of a1 is replaced with at least 1 amino acid of a2 (Replacement 1);
(ii) at least 1 amino acid of c1 is replaced with at least 1 amino acid of c2 (Replacement 2); and
(iii) at least 1 amino acid of g1 is replaced with at least 1 amino acid of g2 (Replacement 3); and wherein (b) HRII comprises seven antiparallel beta strands AII, BII, CII, DII, EII, FII, and GII, six intervening regions bII, cII, dII, eII, fII, and gII, a N-terminal region aII and a C-terminal region hII positioned from N- to C-terminus in the following order:

aII-AII-bII-BII-cII-CII-dII-DII-eII-EII-fII-FII-gII-GII-hII, wherein the HRII is a fusion protein of a third human constant region of an immunoglobulin or immunoglobulin-like protein (3$^{rd}$ CRI, acceptor) interspersed with amino acids of a fourth human constant region of an immunoglobulin or immunoglobulin-like protein (4$^{th}$ CRI, donor), and wherein the 3$^{rd}$ CRI comprises seven antiparallel beta strands A3, B3, C3, D3, E3, F3, and G3, six intervening regions b3, c3, d3, e3, f3, and g3, aN-terminal region a3 and a C-terminal region h3 positioned from N- to C-terminus in the following order:

a3-A3-b3-B3-c3-C3-d3-D3-e3-E3-f3-F3-g3-G3-h3, wherein the 4$^{th}$ CRI comprises seven antiparallel beta strands A4, B4, C4, D4, E4, F4, and G4, six intervening regions b4, c4, d4, e4, f4, and g4, a N-terminal region a4 and a C-terminal region h4 positioned from N- to C-terminus in the following order:

a4-A4-b4-B4-c4-C4-d4-D4-e4-E4-f4-F4-g4-G4-h4, wherein HRII has the amino acid sequence of the 3$^{st}$ CRI and wherein at least the following amino acids of the 3$^{rd}$ CRI are replaced with the following amino acids of the 4$^{th}$ CRI:

(i) at least 1 amino acid of a3 is replaced with at least 1 amino acid of a4 (Replacement 4);
(ii) at least 1 amino acid of c3 is replaced with at least 1 amino acid of c4 (Replacement 5); and
(iii) at least 1 amino acid of g3 is replaced with at least 1 amino acid of g4 (Replacement 6), wherein the 1$^{st}$ CRI and the 3$^{rd}$ CRI are different from each other and specifically bind to each other under physiological conditions.

In a second aspect the present invention provides a nucleic acid encoding the amino acid chain I and/or II of the first aspect.

In a third aspect, the invention provides a vector comprising a nucleic acid of the second aspect.

In a fourth aspect, the present invention provides a method of determining (defining) the amino acid sequence of HRI of a, amino acid chain I and/or of HRII of an amino acid sequence II comprising the steps of:

(i) selecting a 1$^{st}$ CRI, a 2$^{nd}$ CRI, a 3$^{rd}$ CRI, and a 4$^{th}$ CRI;
(ii) determining (defining) the seven beta strands A, B, C, D, E, F and G of the 1$^{st}$ CRI, 2$^{nd}$ CRI, 3$^{rd}$ CRI, and 4$^{th}$ CRI, intervening sequences b, c, d, e, f, and g of the 1$^{st}$ CRI, 2$^{nd}$ CRI, 3$^{rd}$ CRI, and 4$^{th}$ CRI, N- and C-terminal sequences a and h, respectively of the 1$^{st}$ CRI, 2$^{nd}$ CRI, 3$^{rd}$ CRI, and 4$^{th}$ CRI;
(iii) replacing at least 1 amino acid of a of the 1$^{st}$ CRI with at least 1 amino acid of a of the 2$^{nd}$ (Replacement 1); replacing at least 1 amino acid of c of the 1$^{st}$ CRI with at least 1 amino acids of c of the 2$^{nd}$ CRI (Replacement 2); replacing at least 1 amino acid of g of the 1$^{st}$ CRI with at least 1 amino acid of g of the 2$^{nd}$ CRI (Replacement 3); replacing at least 1 amino acid of a of the 3$^{rd}$ CRI with at least 1 amino acid of a of the 4$^{th}$ CRI (Replacement 4); replacing at least 1 amino acid of c of the 3$^{rd}$ with at least 1 amino acid of c of the 4$^{th}$ CRI (Replacement 5); and replacing at least 1 amino acid of g of the 3 with at least 1 amino acid g of the 4$^{th}$ CRI (Replacement 6), wherein the 1$^{st}$ CRI and the 3$^{rd}$ CRI are different from each other and specifically bind to each other under physiological conditions.

In a fifth aspect, the invention provides a method of producing amino acid chain I comprising the HRI sequence determined (defined) according to the fourth aspect and/or amino acid chain II comprising the HRII sequence determined (defined) according to the fourth aspect.

In a sixth aspect, the invention provides the protein complex of the first aspect for use as a medicament.

LIST OF FIGURES

FIG. 1. Schematic picture of constant Ig domain sequence. Represented is the cartoon of a sequence of an Ig domain, while arrows indicate the position of beta strands and bars describe loop regions.

FIG. 2. Schematic view of the heterodimerizing Ig domains. Examplary set of heterodimerizing region I and II (HRI and HRII) with human constant regions of an immunoglobulin or immunoglobulin-like protein (CRI). Possible 1st and 3rd CRI sequences originate from two different heterodimerizing Ig domains (white part, 1$^{st}$ CRI and 3$^{rd}$ CRI) that e.g. hold the potential to form inter-chain disulfide bonds (black bar). Possible 2$^{nd}$ and 4$^{th}$ CRI sequences of Ig domains that interact e.g. with FcRn or other Ig domains 2$^{nd}$ CRI and 4$^{th}$ CRI) are indicated in black.

FIG. 3. Graphic study on a set of Ig domains. Shown is a cartoon of the superimposition of amino acid backbones of a set of Ig domains (see FIG. 4) where ß-strands are displayed in black, while the loop regions are displayed in grey.

FIG. 4. Sequence alignment of several Ig domains. Residues that were predicted to form beta strands are highlighted by black font and dark grey background. Residues that were predicted to form beta strands but excluded from beta strands A-G due to structure or sequence alignment are highlighted by black font and bright grey background. Residues that were not predicted to form beta strands, but included to beta strand A-G due to structure or sequence alignment are highlighted by white font and dark grey background.

FIG. 5. Schematic picture of 2$^{nd}$/4$^{th}$ CRI and 1$^{st}$/3$^{rd}$ CRI sequence definitions. Represented is the sequence of heterodimerizing Ig domains, while arrows indicate the position of beta strands and bars describe loop regions. White color indicates 1$^{st}$/3$^{rd}$ CRI sequences while black color indicates sequence stretches originating from 2$^{nd}$ CRI/4th CRI sequences. Different 2$^{nd}$/4$^{th}$ CRI sequence lengths account for special applications (A: CH31, B: CH3k, C: other domains).

Figure 6:
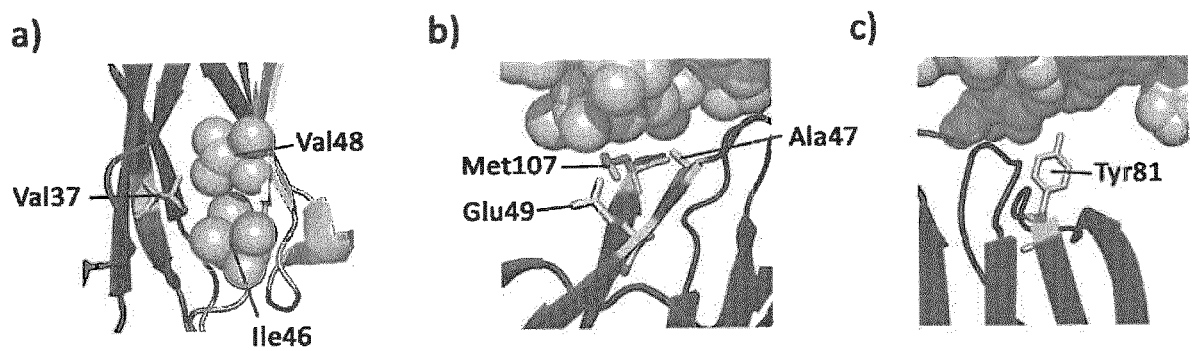

FIG. 6. Graphical study on the additional replacement of $1^{st}/3^{rd}$ CRI residues with $2^{nd}$ CRI/$4^{th}$ CRI amino acids. a) Interaction of Val37 (grey, sticks) of IgG1 CH3 with Ile46 and Val48 (grey spheres), grafted from IgG1 CH3 (grey) to a $1^{st}/3^{rd}$ CRI domain (black). b) Interaction of Glu49, Ala47 and Met107 from IgG CH3 (grey sticks) with residues of a IgG CH2 domain (grey spheres) fused to the N-terminus of the heterodimerizing Ig domain (black). c) Interaction of Tyr81 from IgG CH1 (grey sticks) or any light chain constant domain with a variable domain (grey spheres) fused to the N-terminus of the heterodimerizing Ig domain (black).

Figure 7:
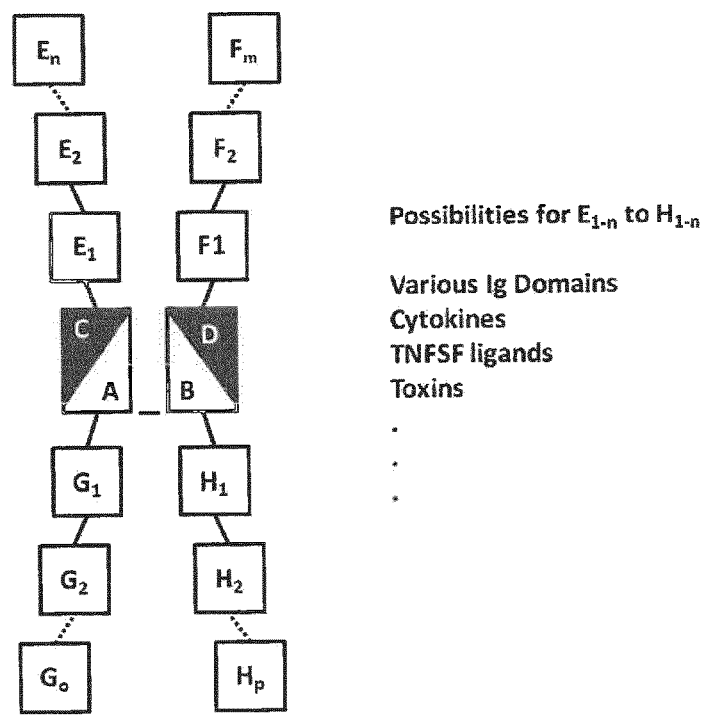

FIG. 7. Extension of the heterodimerizing Ig domains. N- and C-termini of the multifunctional protein complex (e.g. covalently linked heterodimers with FcRn binding ability) might be fused to further protein domains, comprising different Ig domains, TNFSF members, other cytokines, toxins etc.

FIG. 8. Sequence alignment of CH31 (HRI) and CH3k (HRII) Ig domains. Shown is the Alignment of IgG1-CH1 ($1^{st}$ CRI) with IgG1-CH3 ($2^{nd}$ CRI, upper panel) and alignment of Igkappa-CL ($3^{rd}$ CRI) with IgG1-CH3 (4th CRI, lower panel). Sequence parts which were used to create heterodimerizing Ig domains with FcRn binding ability are underlined. Residues that were predicted to form beta strands are highlighted by black font and dark grey background. Residues that were predicted to form beta strands but excluded from beta strands A-G due to structure or sequence alignment are highlighted by black font and bright grey background. Residues that were not predicted to form beta strands, but included to beta strands A-G due to structure or sequence alignment are highlighted by white font and dark grey background.

Figure 9:
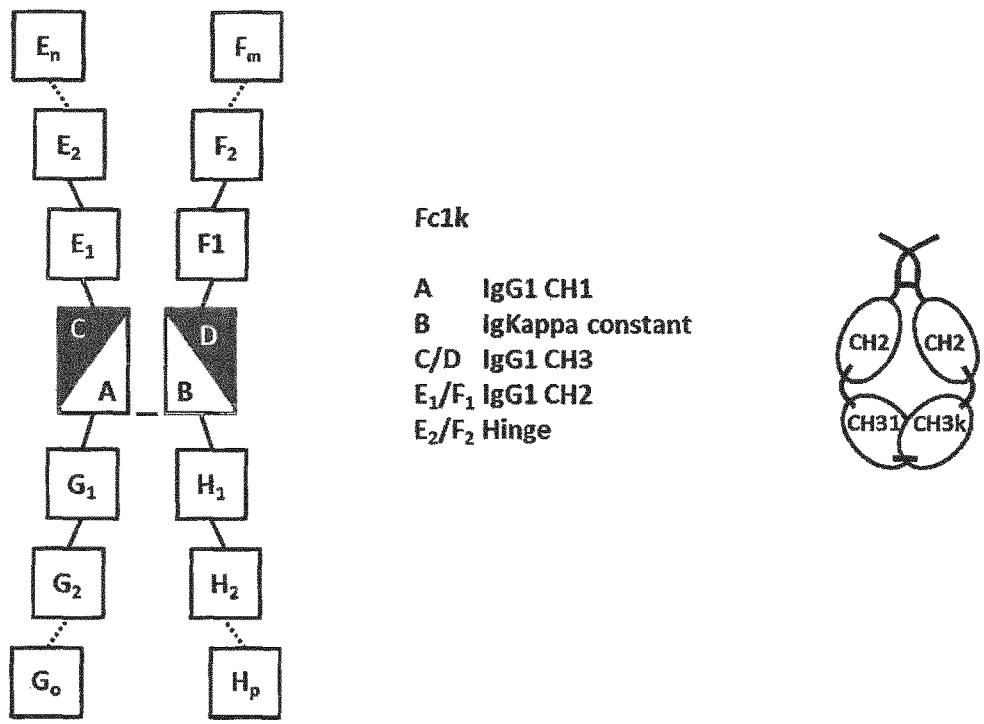

FIG. 9. Heterodimerizing Fc part. Example 1 shows the application of the presented system in order to create a heterodimerizing antibody Fc part. Therefore, IgG1-CH1 and Igkappa CL were used as $1^{st}$ CRI and $3^{rd}$ CRI, respectively with grafted IgG1-CH3 $2^{nd}$ CRI and 4th CRI sequences, fused to the C-termini of IgG1 Hinge and CH2 sequences (named Folk).

Figure 10:
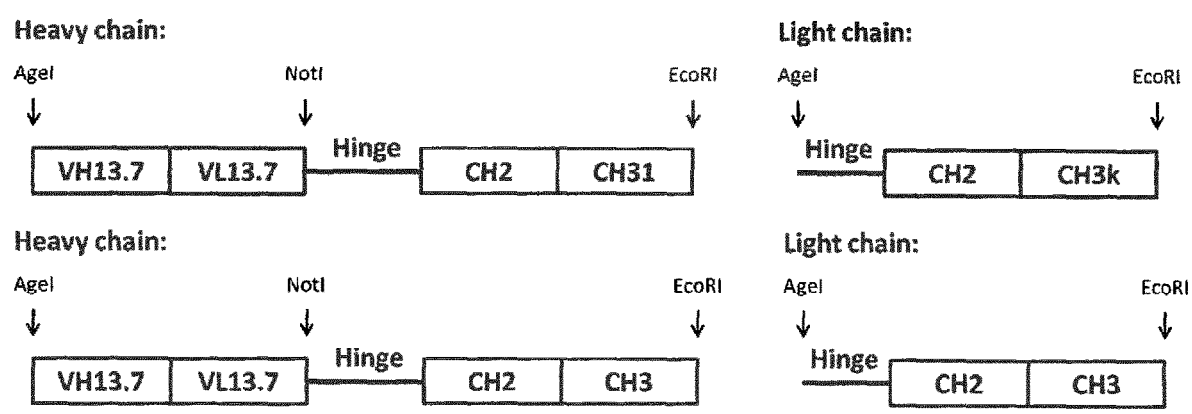

FIG. 10. Genotype of control constructs scFv13.7-Fc1k and scFv13.7-Fc. a) Genetic arrangement of heterodimerizing IgG domains of scFv13.7-Fc1k heavy and light chain including restriction sites used for cloning. b) Genetic arrangement of homodimerizing IgG domains of scFv13.7-Fc heavy and light chain including restriction sites used for cloning.

Figure 11:
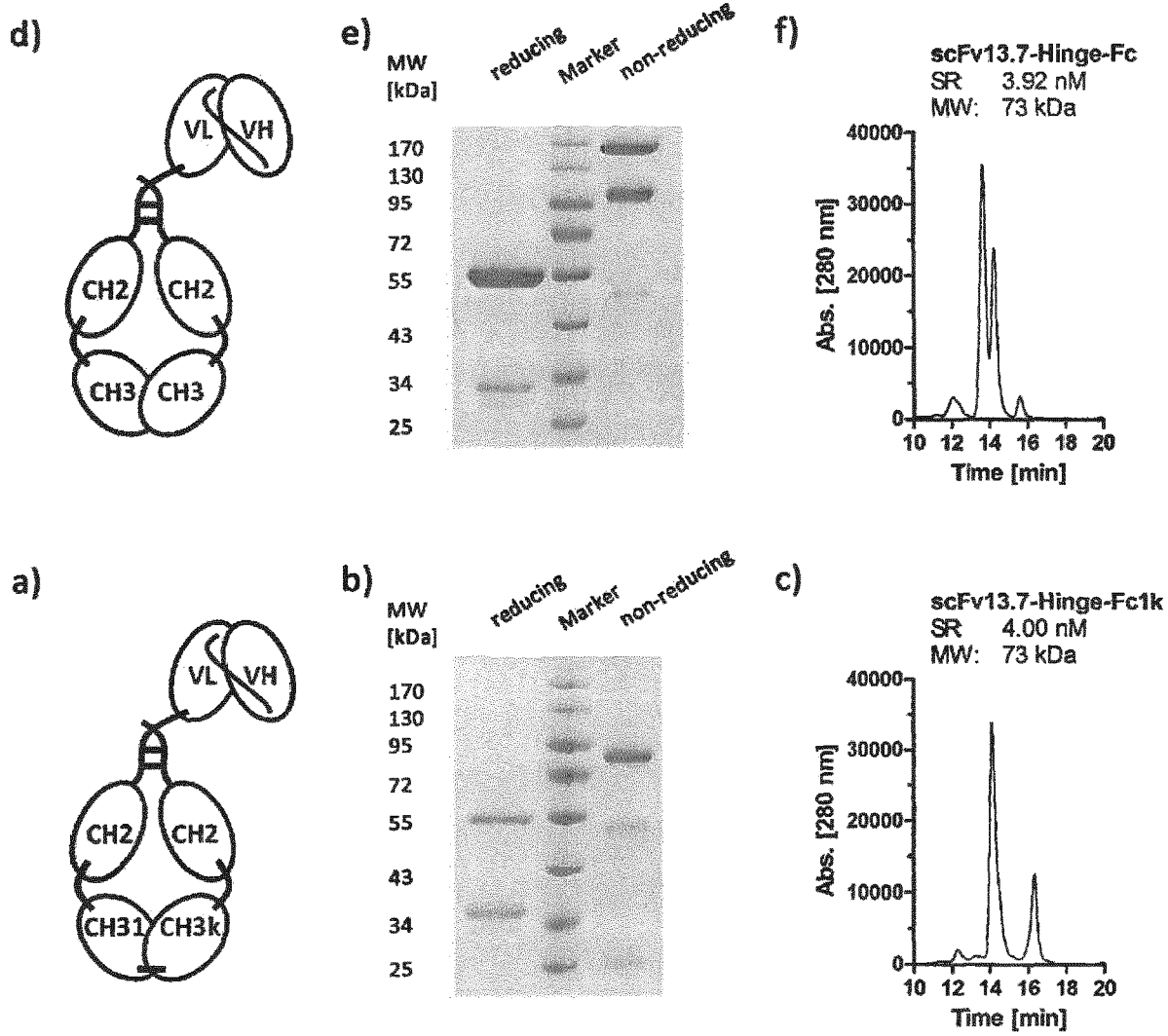

FIG. 11. Expression of control constructs scFv13.7-Fc1k and scFv13.7-Fc. a) Schematic illustration of scFv13.7-Fc1k. b) SDS-PAGE of purified scFv13.7-Fc1k (5% stacking gel, 12% resolution gel). c) Size exclusion chromatography of scFv13.7-Fc1k. d) Schematic illustration of scFv13.7-Fc. e) SDS-PAGE of purified scFv13.7-Fc (5% stacking gel, 12% resolution gel). f) Size exclusion chromatography of scFv13.7-Fc.

Figure 12:
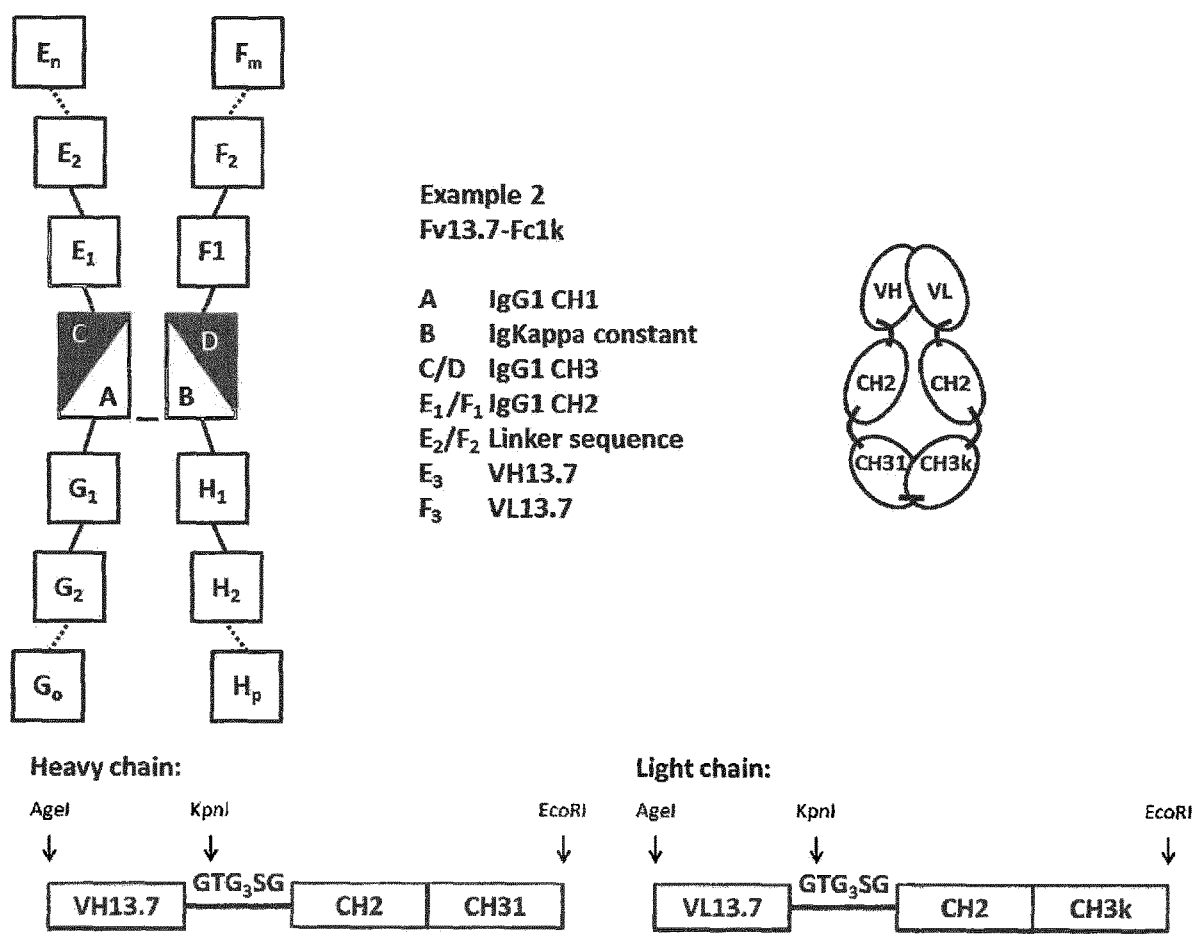

FIG. 12. Schematic view of example 2; Fv13.7-Fc1k. Upper panel, generation of multifunctional Ig domains. Therefore, IgG1-CH and Igkappa CL were used as $1^{st}$ CRI and $3^{rd}$ CRI, respectively with grafted IgG1-CH3 $2^{nd}$ CRI and $4^{th}$ CRI sequences, fused to the C-termini of IgG1-CH2 (named Fc1k). Fusing of VH13.7 or VL13.7 one to each of the CH2 domains connected via linker sequences resulted in the creation of the monovalent Fv13.7-Fc1k. Lower panel, genetic arrangement of IgG domains of Fv13.7-Fc1k heavy and light chain including restriction sites used for cloning.

Figure 13:
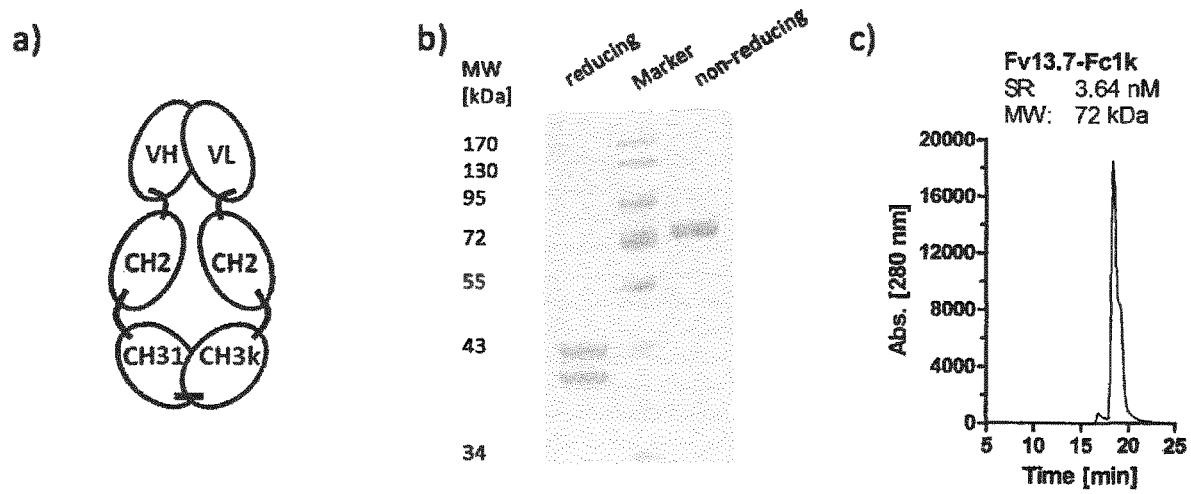

FIG. 13. Expression of Fv13.7-Fc1k. a) Schematic illustration of Fv13.7-Fc1k. b) SDS-PAGE of purified Fv13.7-Fc1k (5% stacking gel, 12% resolution gel). c) Size exclusion chromatography of Fv13.7-Fc1k.

Figure 14:
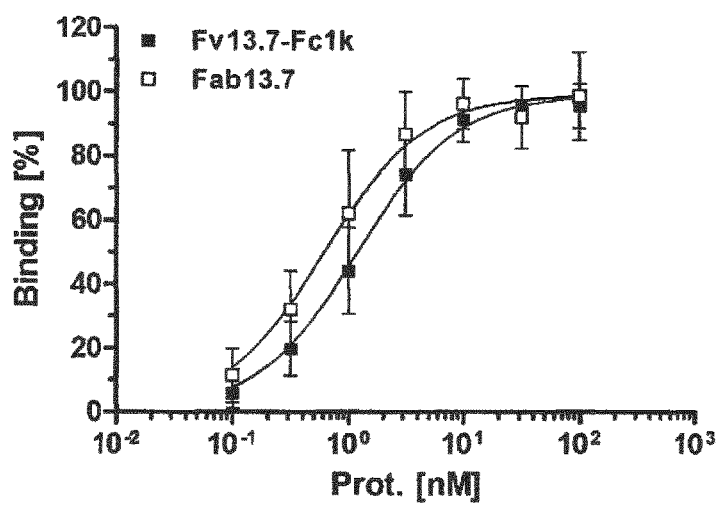

FIG. 14. Equilibrium binding of Fv13.7-Fc1k to human TNFR1-Fc. Increasing concentrations were tested for their binding to huTNFR1-Fc in ELISA (n=3, mean±SD). Fabl 3.7 served as control.

Figure 15:
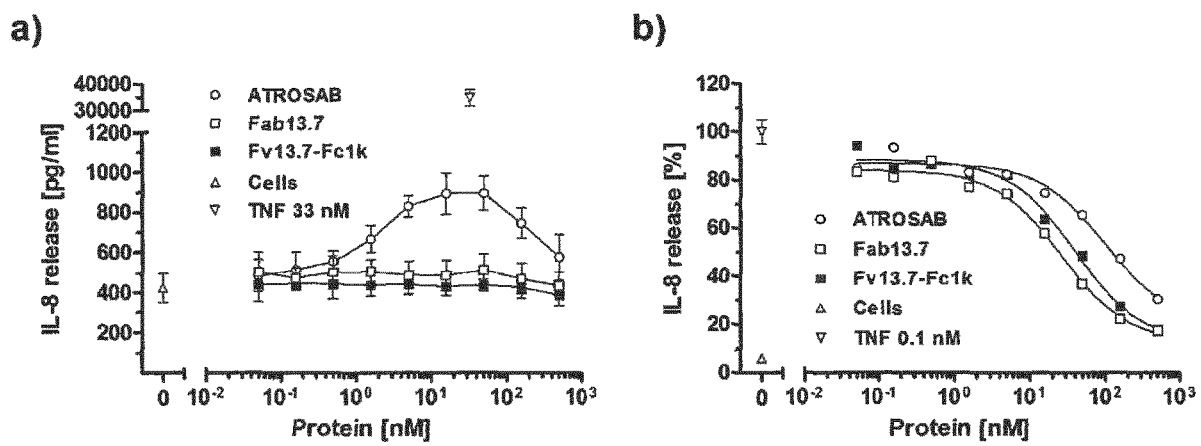

FIG. 15. Bioactivity of Fv13.7-Fc1k. a) IL-8 release from HT1080 cells, triggered by Fv13.7-Fc1k. Unstimulated cells, TNF (33 nM), ATROSAB and Fab13.7 served as controls. Presented are mean and SD of two individual experiments. b) Presented is the inhibition of IL-8, induced by 0.1 nM TNF. ATROSAB, Fab13.7, 0.1 nM TNF and unstimulated cells served as controls. Shown are mean and SD of two individual experiments.

Figure 16:
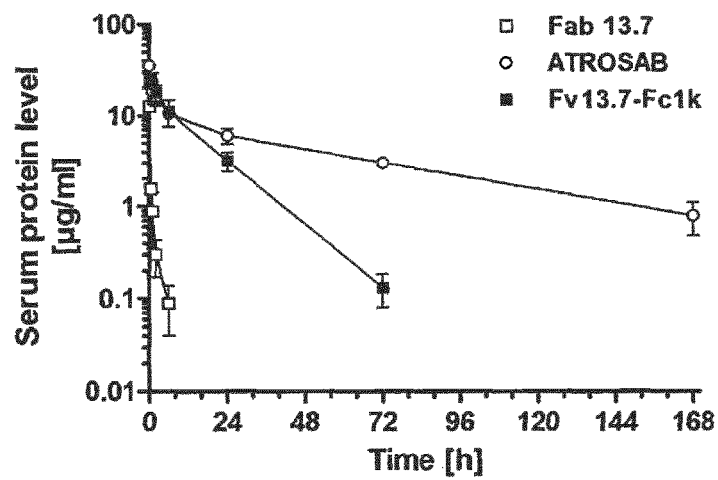

FIG. 16. Pharmacokinetic study of Fv13.7-Fc1k. Initial and terminal plasma half-live after single-dose injection (25 µg), as well as bioavailability (area under the curve) were determined using C57BL/6J mice (n=3/n=4 in case of ATROSAB) homozygously bearing the extracellular domain of human TNFR1 at the locus of the mouse gene. Remaining active antibody in serum samples was detected by ELISA. ATROSAB and Fab13.7 served as controls.

FIG. 17. Schematic view of example 3—$FAP_N$-$CH3_N$-hFc and $FAP_N$-CH3N-Fc. Two scFv fragments targeting either FAP or CD3 were fused N-terminally to the hinge region of the heterodimerizing Fc part Fc1k (example 3a). The same construct was created using a hinge sequence without cysteines in order to avoid hinge mediated covalent crosslinking (example 3b)

FIG. 18. Schematic view of example 4—$FAP_N$-CH3c-hFc and $FAP_N$-CH3c-Fc. Two scFv fragments targeting either FAP or CD3 were fused N-terminally (FAP) or C-terminally (CD3) to the heterodimerizing Fe part Fc1k (example 4a). The same construct was created using a hinge sequence without cysteines in order to avoid hinge mediated covalent crosslinking (example 4b)

FIG. 19. Schematic view of example 5—$FAP_{NN}$-CH3c-hFc and $FAP_{NN}$-CH3c-Fc. Two scFv fragments targeting FAP were fused N-terminally to the heterodimerizing Fe part Fc1k and another scFv targeting CD3 was fused to Fc1k C-terminally (example 5a). The same construct was created using a hinge sequence without cysteines in order to avoid hinge mediated covalent crosslinking (example 5b)

FIG. 20. Schematic view of example 6—$FAP_{NC}$-CH3c-hFc and $FAP_{NC}$-CH3c-Fe. Two scFv fragments targeting FAP were fused either N-terminally or C-terminally to the heterodimerizing Fc part Fc1k and another scFv targeting CD3 was fused to Fc1k C-terminally (example 6a). The same construct was created using a hinge sequence without cysteines in order to avoid hinge mediated covalent crosslinking (example 6b)

Figure 21:
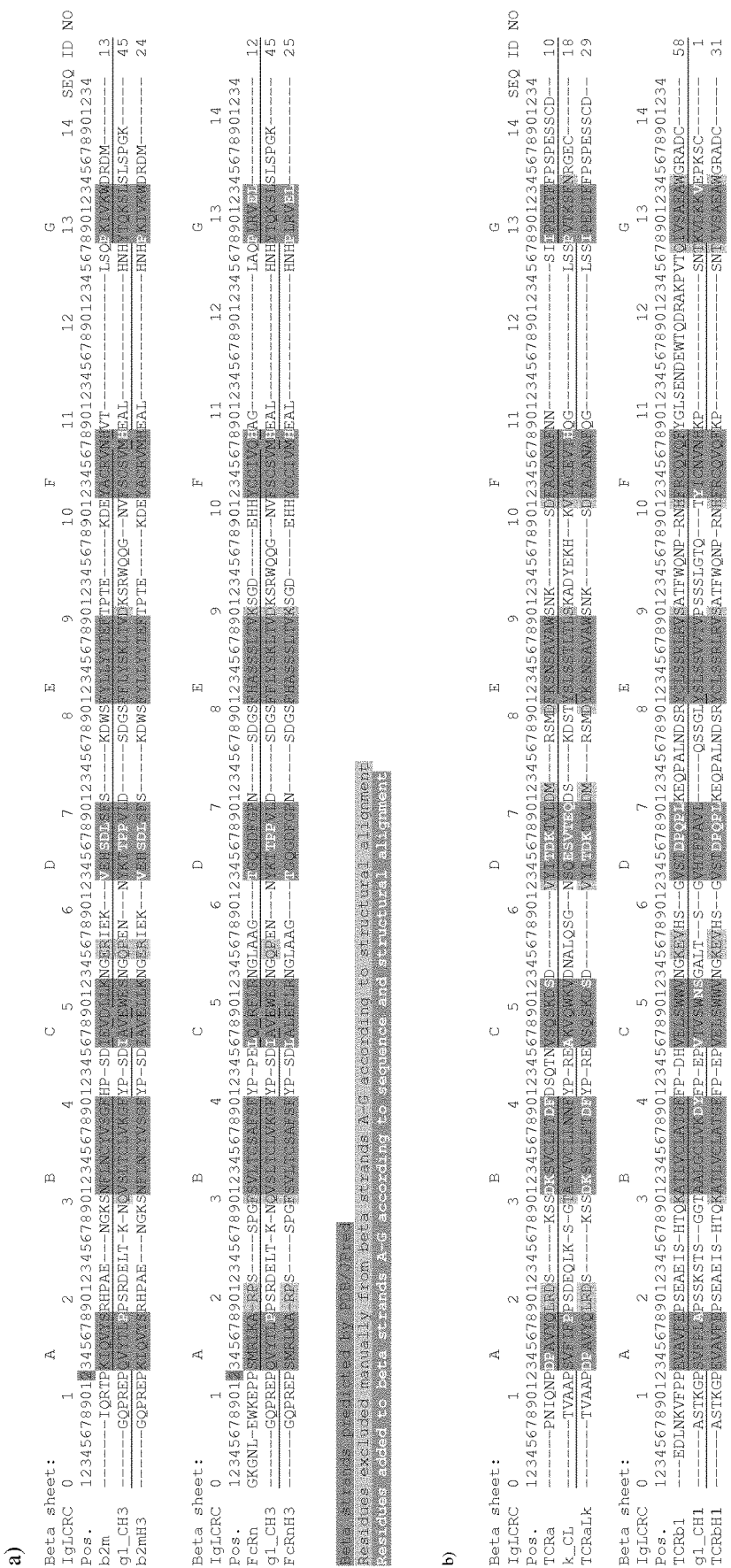

FIG. 21. Sequence alignment of $1^{st}$ CRI/$3^{rd}$ CRI and $2^{nd}$ CRI/$4^{th}$ CRI sequences for the generation of a bispecific IgG. FcRn alpha 3 and beta 2 microglobulin $1^{st}$ CRI and $3^{rd}$ CRI domain sequences are aligned to IgG CH3 $2^{nd}$ CRI and $4^{th}$ CRI domain sequences (a), and TCR alpha 2 and TCR beta 2 $1^{st}$ CRI and $3^{rd}$ CRI domain sequences are aligned to IgG CH1 and Igkappa constant domain $2^{nd}$ CRI and $4^{th}$ CRI sequences, respectively (b). Sequence parts which were used to create heterodimerizing Ig domains with FcRn binding (a) or inter-Ig domain interaction (b) ability are underlined. Residues that were predicted to form beta strands are highlighted by black font and dark grey background. Residues that were predicted to form beta strands but excluded from beta strands A-G due to structure or sequence alignment are highlighted by black font and bright grey background. Residues that were not predicted to form beta strands, but included to beta strands A-G due to structure or sequence alignment are highlighted by white font and dark grey background.

FIG. 22. Schematic view of example 7—bispecific IgG. Two multifunctional Ig domains have to be created in order to provide for Fc heterodimerization and solving the light chain problem. Fcb2Rn consists of FcRn alpha 3 and beta 2 microglobulin $1^{st}$ CRI and $3^{rd}$ CRI domain sequences and grafted IgG CH3 $2^{nd}$ CRI and $4^{th}$ CRI sequences (7a). FabTCR consists of TCR alpha 2 and TCR beta 2 $1^{st}$ CRI and $3^{rd}$ CRI domain sequences and grafted IgG CH1 and Igkappa constant domain $2^{nd}$ CRI and $4^{th}$ CRI sequences (7b).

FIG. 23. Schematic view of example 8—Fv13.7x-Fc1k. Upper panel, generation of multifunctional Ig domains. Therefore, IgG1-CH1 and Igkappa CL were used as 1st CRI and 3rd CRI, respectively with grafted IgG1-CH3 2nd CRI and 4th CRI sequences, fused to the C-termini of IgG1-CH2 (named Fc1k). Fusing of VH13.7 or VL13.7 one to each of the CH2 domains connected via linker sequences resulted in the creation of the monovalent Fv13.7x-Fc1k. Lower panel, genetic arrangement of IgG domains of Fv13.7x-Fc1k heavy and light chain including restriction sites used for cloning.

Figure 24:
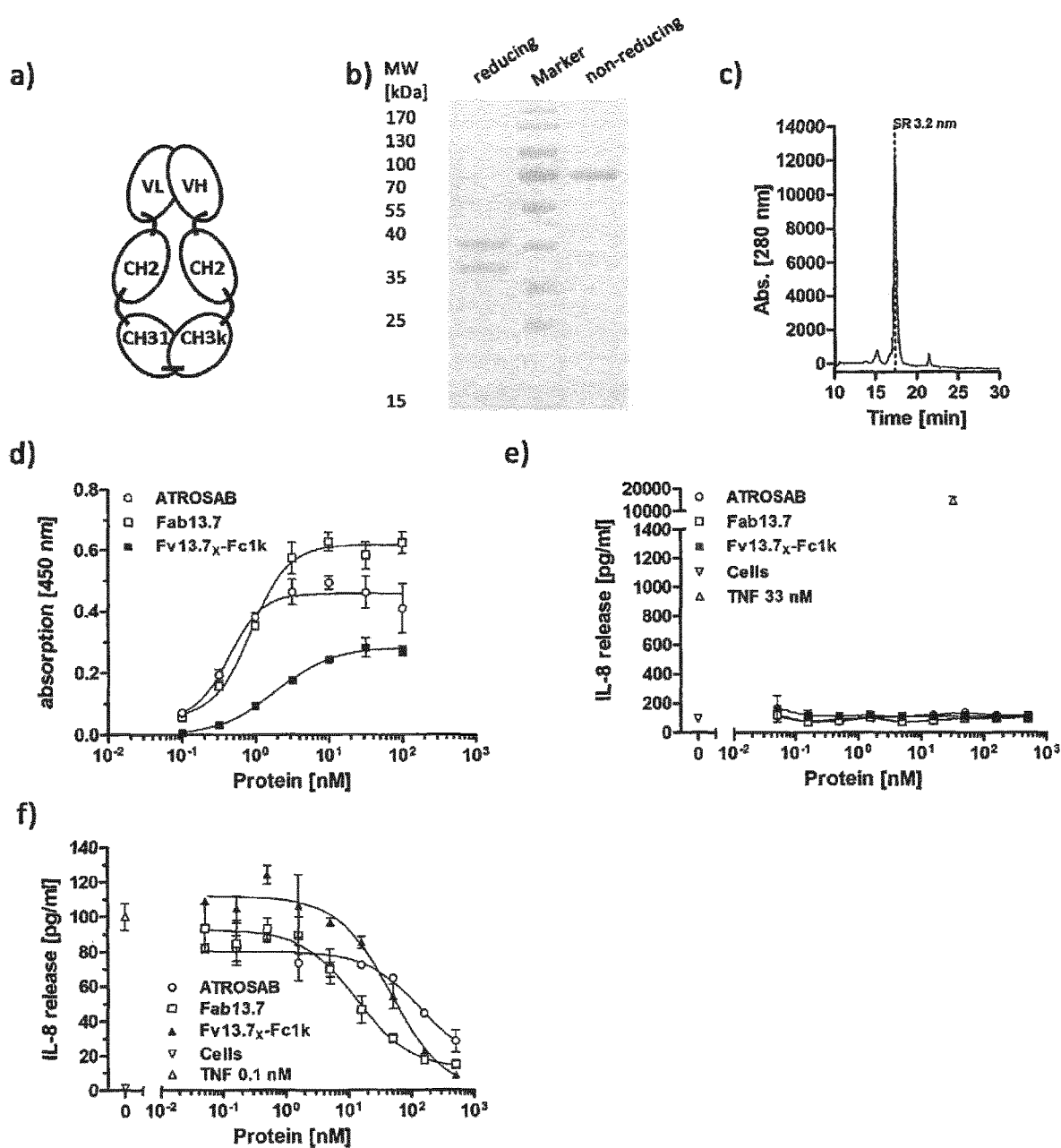

FIG. 24. Production and bioactivity of Fv13.7x-Fc. a) genotype of Fv13.7x Fc1k. b) Purified protein was analyzed by SDS-PAGE (10%, Coomassie-stained) and subsequently by SEC (c, Yarra SEC-3000 column, flow rate 0.5 ml/min). d) Fv13.7x Fc1k was tested by ELISA for binding to human TNFR1-Fc (n=1, Mean±SD of duplicates, ATROSAB and Fab13.7 served as controls). e) IL-8 release from HT1080 cells triggered by Fv13.7x Fc1k was analyzed (n=1, Mean±SD of duplicates, ATROSAB, Fab13.7, unstimulated cells and recombinant human TNF served as controls) as well as the inhibition of TNF-induced IL-8 release, using 0.1 nM recombinant human TNF (f, n=1, Mean±SD of duplicates, ATROSAB, Fab13.7, unstimulated cells and recombinant human TNF served as controls).

FIG. 25. Schematic view of example 9—FvCD3-Fc1k-scFvHer32. Upper panel, generation of multifunctional Ig domains. Therefore, IgG1-CH1 and Igkappa CL were used as 1st CRI and 3rd CRI, respectively with grafted IgG1-CH3 2nd CRI and 4th CRI sequences, fused to the C-termini of IgG1-CH2 (named Fc1k). Fusing of VHCD3 or VLCD3 one to each of the CH2 domains connected via linker sequences and, in addition, fusing one Her3-targeting scFv fragments to each C-terminus of the Folk resulted in the creation of the bispecific and trivalent FvCD3-Fc1k-scFvHer32. Lower panel, genetic arrangement of IgG domains of the FvCD3-Fc1k-scFvHer32 chains including restriction sites used for cloning.

Figure 26:
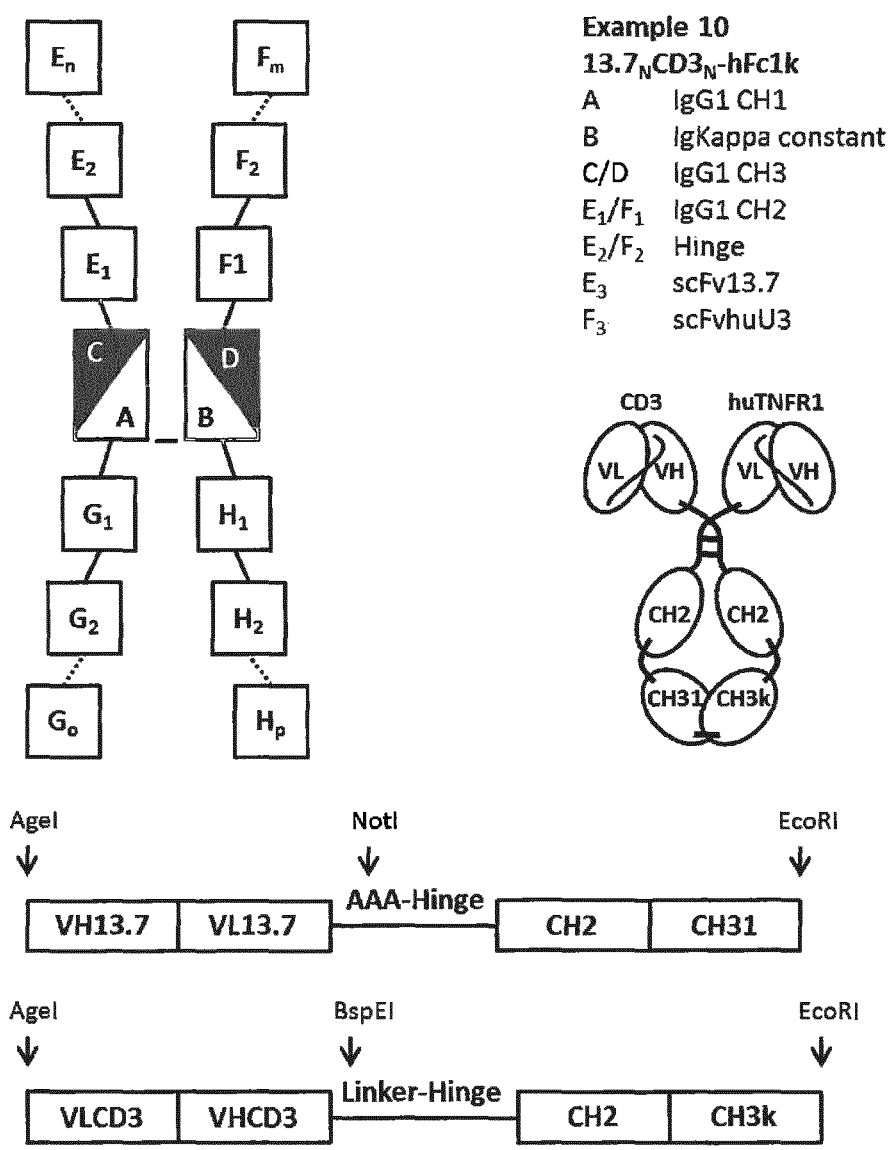

FIG. 26. Schematic view of example 10-13.7$_N$CD3$_N$-hFc1k. Upper panel, generation of multifunctional Ig domains. Therefore, IgG1-CH1 and Igkappa CL were used as $1^{st}$ CRI and $3^{rd}$ CRI, respectively with grafted IgG1-CH3 $2^{nd}$ CRI and 4th CRI sequences, fused to the C-termini of IgG1-CH2 (named Fc1k). Two scFv fragments targeting either human TNFR1 (scFv13.7) or CD3 were fused N-terminally to the hinge region of the heterodimerizing Fc part Fc1k. Lower panel, genetic arrangement of IgG domains of the 13.7$_N$CD3$_N$-hFc1k chains including restriction sites used for cloning.

Figure 27:
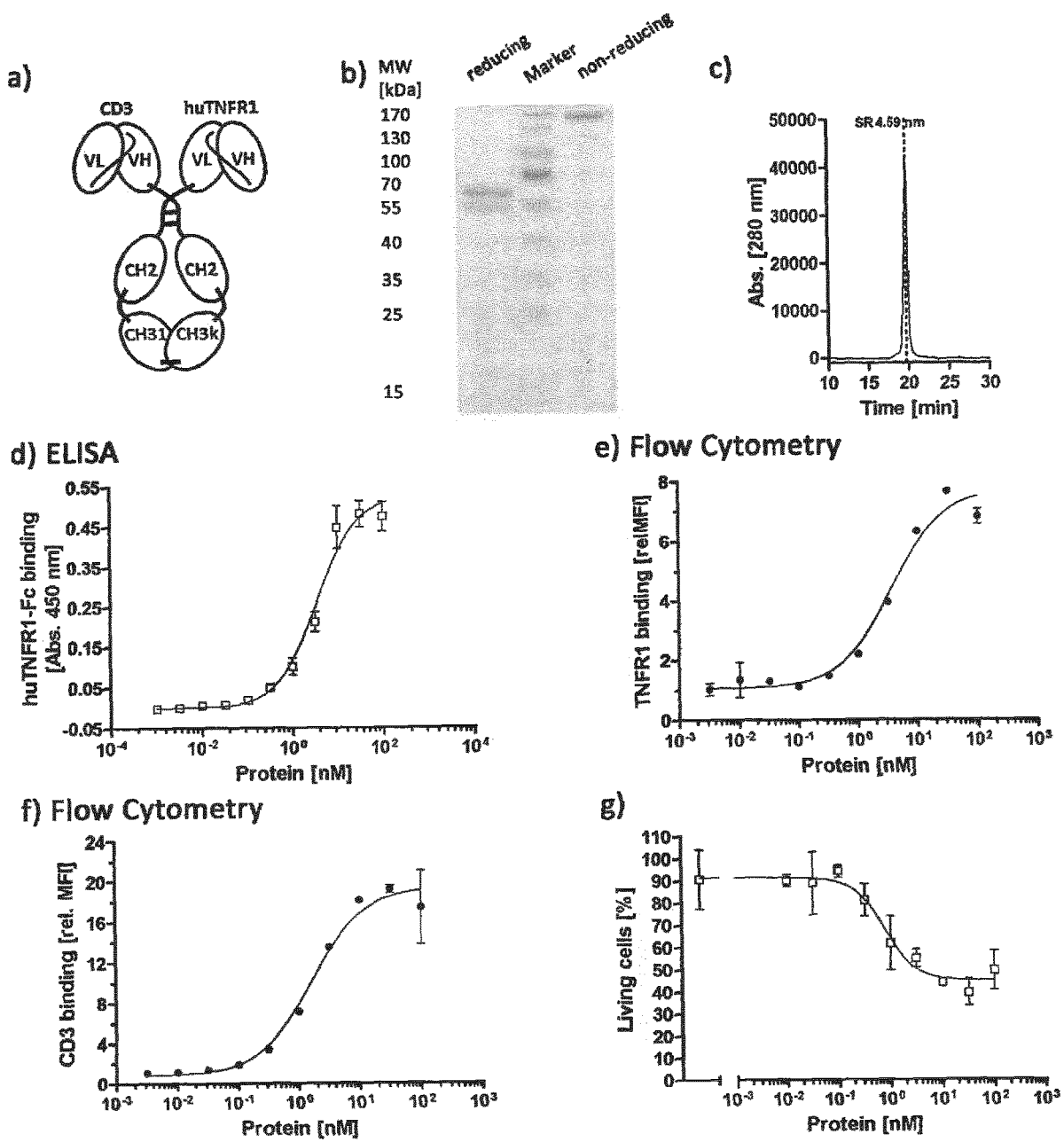

FIG. 27. Production and bioactivity of 13.7$_N$CD3$_N$-hFc1k. a) genotype of 13.7$_N$CD3$_N$-hFc1k. b) Purified protein was analyzed by SDS-PAGE (10%, Coomassie-stained) and subsequently by SEC (c, Yarra SEC-3000 column, flow rate 0.5 ml/min). d) 13.7$_N$CD3$_N$-hFc1k was tested by ELISA for binding to human TNFR1-Fc (n=1, Mean±SD of duplicates). e) Binding of 13.7$_N$CD3$_N$-hFc1k to TNFR1 expressing HT1080 cells (n=1, Mean±SD of duplicates) as well as to CD3 expressing Jurkat cells was analyzed by flow cytometry (f, n=1, Mean±SD of duplicates). g) Recruitment and activation of human peripheral blood mononuclear cells to TNFR1 expressing HT1080 cells was tested in vitro by crystal violet staining of surviving target cells after 5 days of stimulation (n=1, Mean±SD of duplicates).

Figure 28:
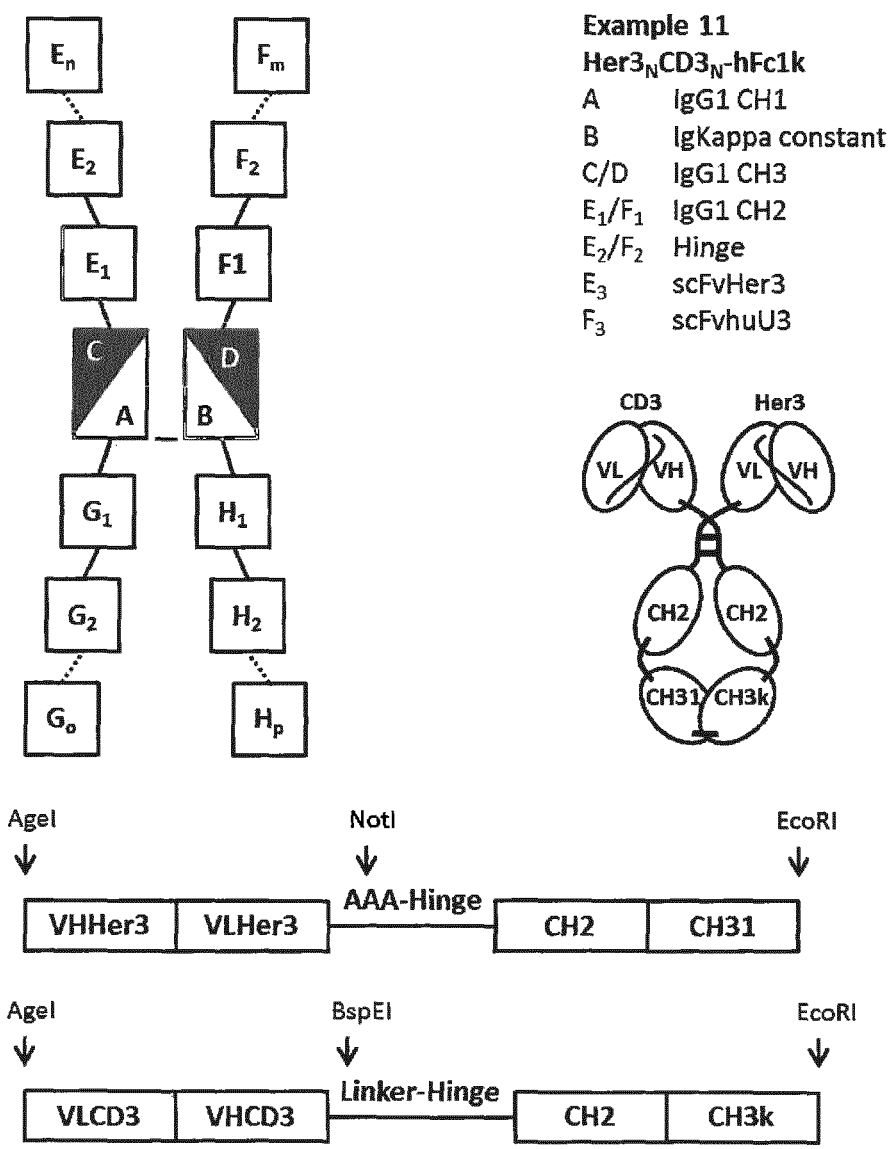

FIG. 28. Schematic view of example 10—Her3$_N$CD3$_N$-hFc1k. Upper panel, generation of multifunctional Ig domains. Therefore, IgG1-CH1 and Igkappa CL were used as $1^{st}$ CRI and $3^{rd}$ CRI, respectively with grafted IgG1-CH3 $2^{nd}$ CRI and $4^{th}$ CRI sequences, fused to the C-termini of IgG1-CH2 (named Fc1k). Two scFv fragments targeting either Her3 or CD3 were fused N-terminally to the hinge region of the heterodimerizing Fc part Fc1k. Lower panel, genetic arrangement of IgG domains of the Her3$_N$CD3$_N$-hFc1k chains including restriction sites used for cloning.

Figure 29:
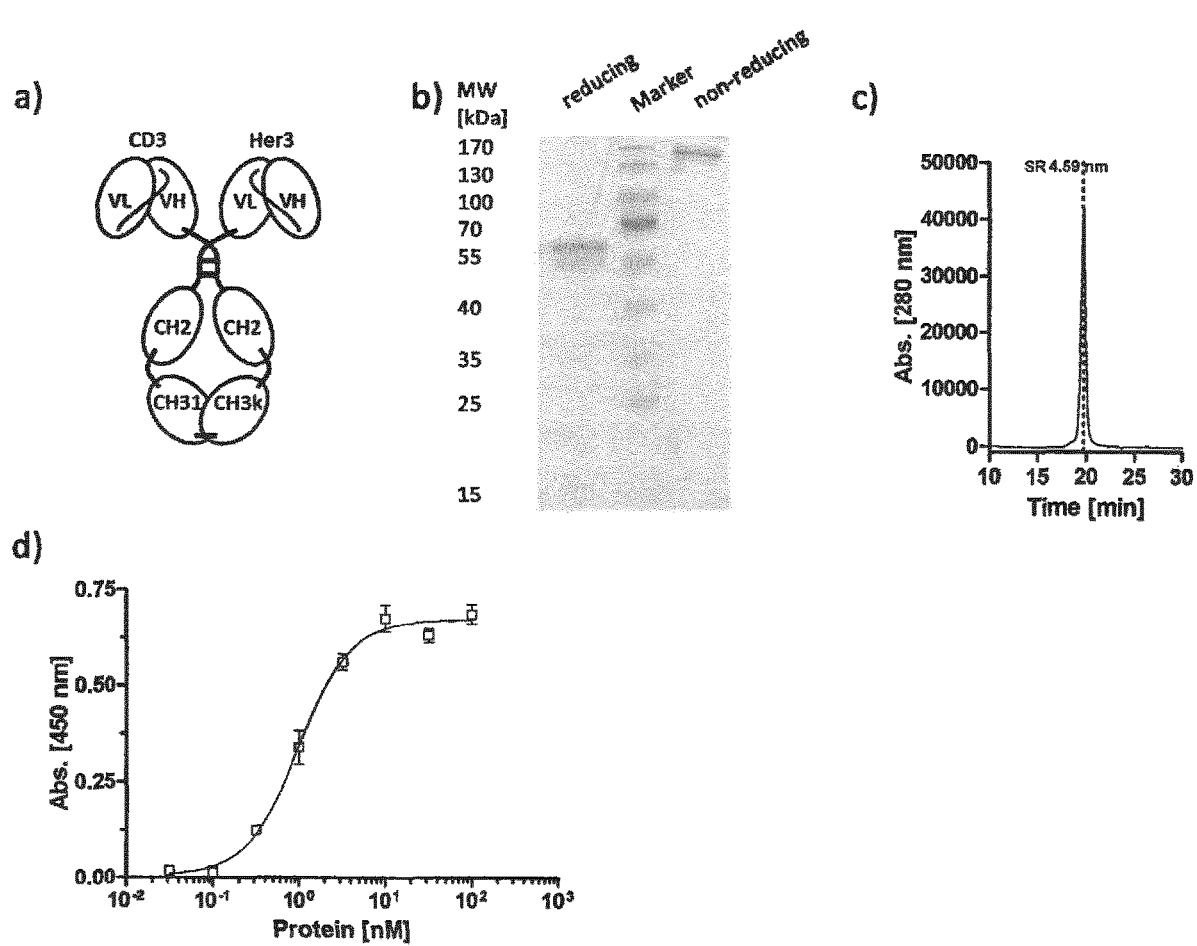

FIG. 29. Production and bioactivity of Her3$_N$CD3$_N$-hFc1k. a) genotype of Her3$_N$CD3$_N$-hFc1k. b) Purified protein was analyzed by SDS-PAGE (10%, Coomassie-stained) and subsequently by SEC (c, Yarra SEC-3000 column, flow rate 0.5 ml/min). d) Her3$_N$CD3$_N$-hFc1k was tested by ELISA for binding to Her3-Fc (n=1, Mean±SD of duplicates).

FIG. 30. Schematic view of example 10—MSCP$_N$CD3$_N$-hFc1k. Upper panel, generation of multifunctional Ig domains. Therefore, IgG1-CH1 and Igkappa CL were used as $1^{st}$ CRI and $3^{rd}$ CRI, respectively with grafted IgG1-CH3 $2^{nd}$ CRI and $4^{th}$ CRI sequences, fused to the C-termini of IgG1-CH2 (named Fc1k). Two scFv fragments targeting either MSCP or CD3 were fused N-terminally to the hinge region of the heterodimerizing Fc part Fc1k. Lower panel, genetic arrangement of IgG domains of the MSCP$_N$CD3$_N$-hFc1k chains including restriction sites used for cloning.

Figure 31:
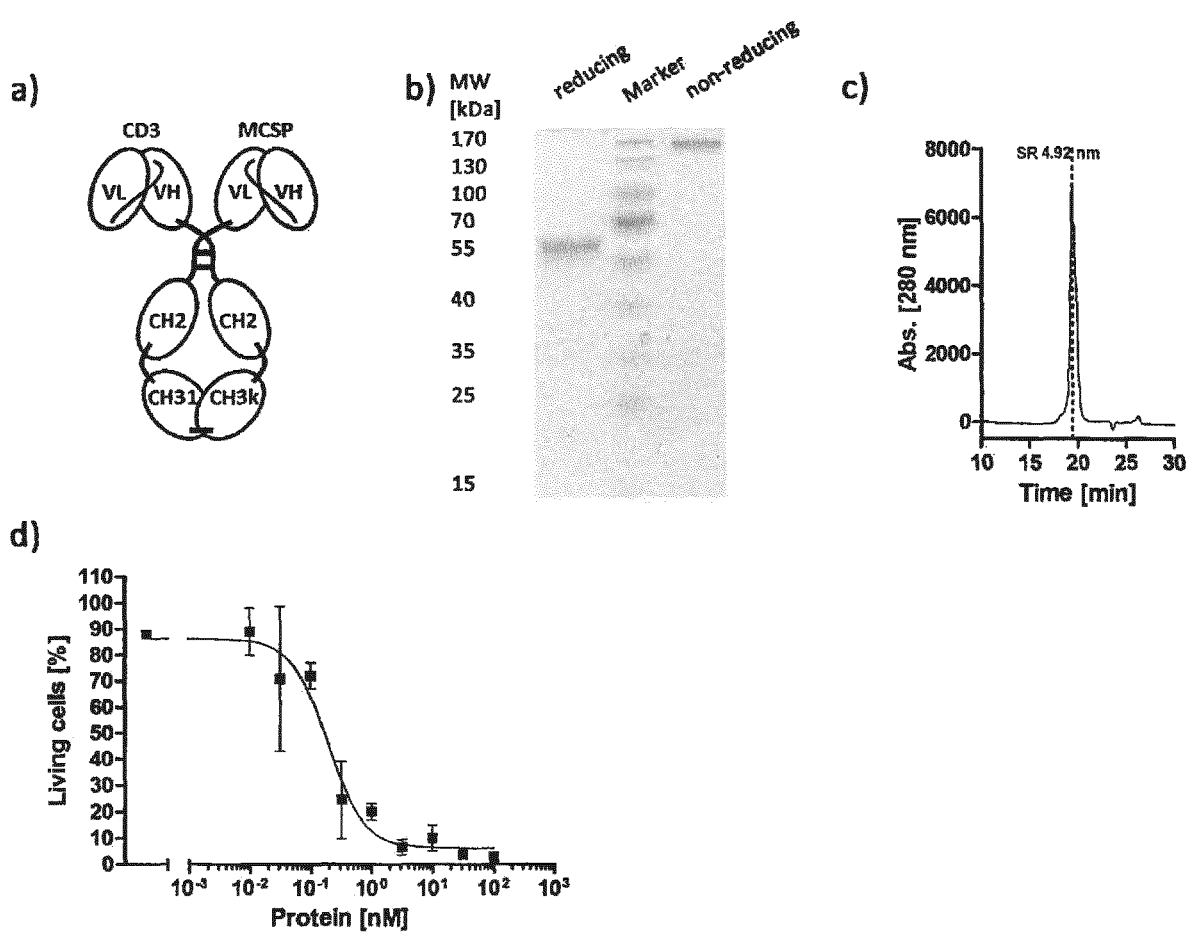

FIG. 31. Production and bioactivity of MSCP$_N$CD3$_N$-hFc1k. a) genotype of MSCP$_N$CD3$_N$-hFc1k. b) Purified protein was analyzed by SDS-PAGE (10%, Coomassie-stained) and subsequently by SEC (c, Yarra SEC-3000 column, flow rate 0.5 ml/min). d) Recruitment and activation of human peripheral blood mononuclear cells to MSCP expressing WM35 cells was tested in vitro by crystal violet staining of surviving target cells after 5 days of stimulation (n=1, Mean±SD of duplicates).

Figure 32:
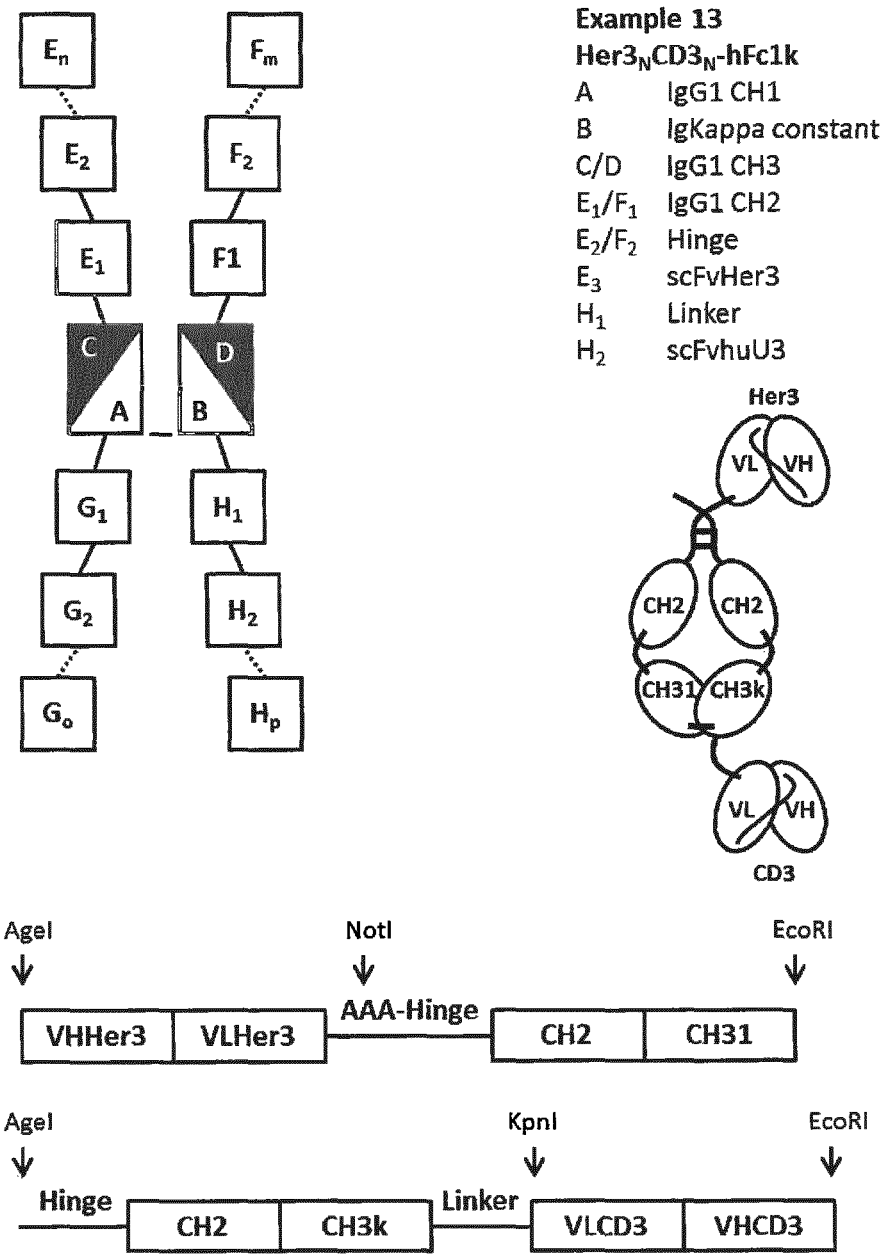

FIG. 32. Schematic view of example 10—Her3$_N$CD3c-hFc1k. Upper panel, generation of multifunctional Ig domains. Therefore, IgG1-CH1 and Igkappa CL were used as $1^{st}$ CRI and $3^{rd}$ CRI, respectively with grafted IgG1-CH3 $2^{nd}$ CRI and $4^{th}$ CRI sequences, fused to the C-termini of IgG1-CH2 (named Fc1k). Two scFv fragments targeting either Her3 or CD3 were fused N- or C-terminally to the hinge region of the heterodimerizing Fc part Fc1k, respectively. Lower panel, genetic arrangement of IgG domains of the Her3$_N$CD3c-hFc1k chains including restriction sites used for cloning.

Figure 33:
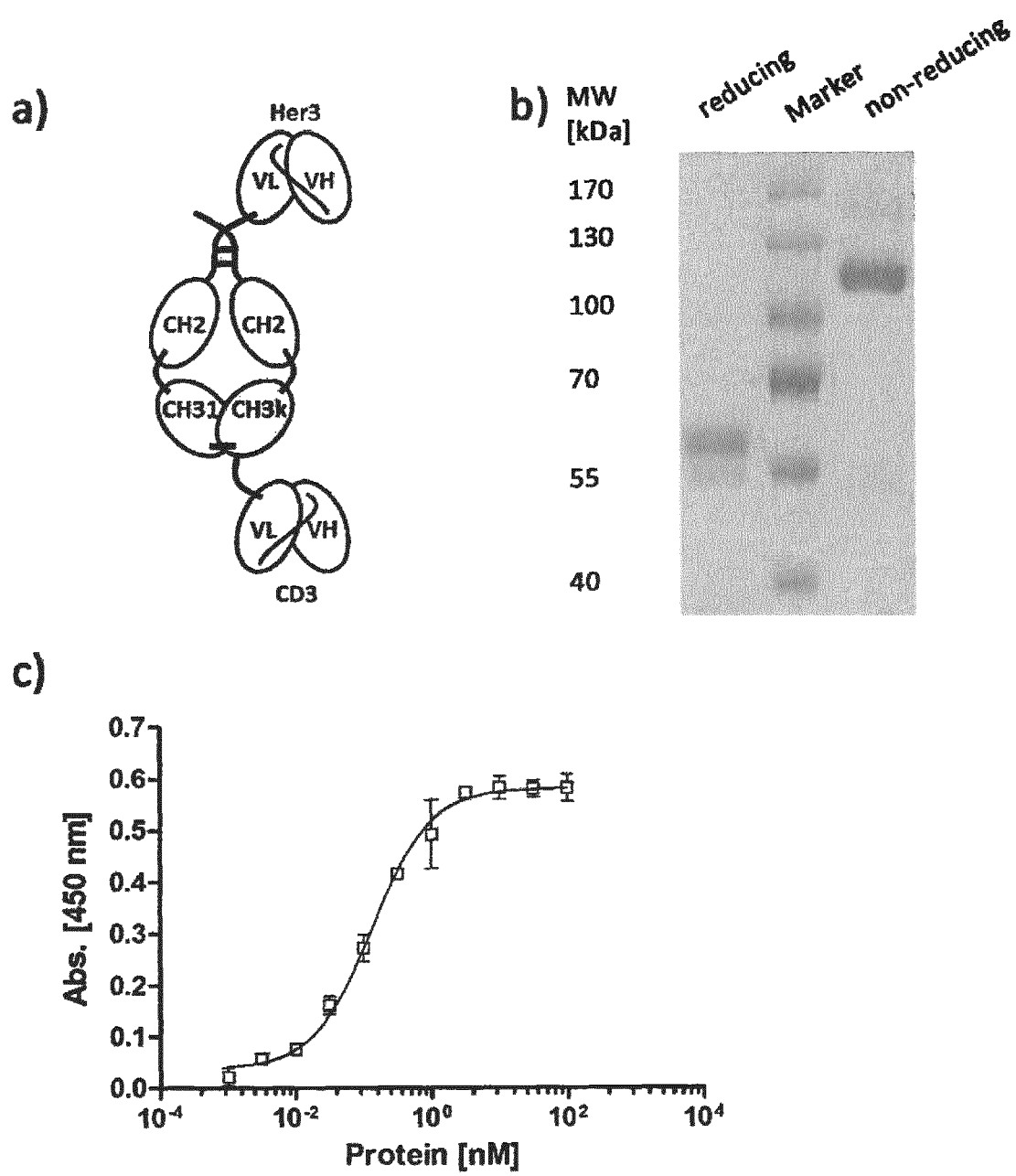

FIG. 33. Production and bioactivity of Her3$_N$CD3c-hFc1k. a) genotype of Her3$_N$CD3c-hFc1k. b) Purified protein was analyzed by SDS-PAGE (10%, Coomassie-stained) and subsequently by SEC (c, Yarra SEC-3000 column, flow rate 0.5 ml/min). d) Her3$_N$CD3c-hFc1k was tested by ELISA for binding to Her3-Fc (n=1, Mean±SD of duplicates).

FIG. 34. Sequences.

LIST OF SEQUENCES—FREE TEXT INFORMATION

SEQ ID NO: 1 Amino acid sequence of CH1 of IgG
SEQ ID NO: 2 Amino acid sequence of CH1 of IgG2

SEQ ID NO: 3 Amino acid sequence of CH1 of IgG3
SEQ ID NO: 4 Amino acid sequence of CH1 of IgG4
SEQ ID NO: 5 Amino acid sequence of CH1 of IgA1
SEQ ID NO: 6 Amino acid sequence of CH1 of IgA2
SEQ ID NO: 7 Amino acid sequence of CH1 of IgD
SEQ ID NO: 8 Amino acid sequence of CH1 of IgE
SEQ ID NO: 9 Amino acid sequence of CH1 of IgM
SEQ ID NO: 10 Amino acid sequence of TCR α
SEQ ID NO: 11 Amino acid sequence of TCR β
SEQ ID NO: 12 Amino acid sequence of FcRn alpha 3
SEQ ID NO: 13 Amino acid sequence of β 2 micro globulin
SEQ ID NO: 14 Amino acid sequence of HLA-A
SEQ ID NO: 15 Amino acid sequence of HLA-B α3
SEQ ID NO: 16 Amino acid sequence of HLA-D α2
SEQ ID NO: 17 Amino acid sequence of HLA-D β2
SEQ ID NO: 18 Amino acid sequence of Igκ constant region
SEQ ID NO: 19 Amino acid sequence of Igλ constant region
SEQ ID NO: 20 Amino acid sequence of CH3I, 1st CRI: CH1(IgG1), 2nd CRI: CH3(IgG1)
SEQ ID NO: 21 Amino acid sequence of CH3κ, 3rd CRI: CLκ, 2nd CRI: CH3(IgG1)
SEQ ID NO: 22 Amino acid sequence of CH1H3, 1st CRI: CH1 (IgG1), 2nd CRI: CH3 (IgG1)
SEQ ID NO: 23 Amino acid sequence of CLκH3, 3rd CRI: CLκ, 4th CRI: CH3 (IgG1)
SEQ ID NO: 24 Amino acid sequence of b2mH3, 1st CRI: beta 2 microglobulin, 2nd CRI: CH3 (IgG1)
SEQ ID NO: 25 Amino acid sequence of FcRnH3, 3rd CRI: FcRn alpha 3 domain, 4th CRI: CH3 (IgG1)
SEQ ID NO: 26 Amino acid sequence of TCRaH3, 1st CRI: TCR alpha chain constant domain, 2nd CRI: CH3 (IgG1)
SEQ ID NO: 27 Amino acid sequence of TCRbH3, 3rd CRI: TCR beta chain constant domain, 4th CRI: CH3 (IgG1)
SEQ ID NO: 28 Amino acid sequence of TCRaH1, 1st CRI: TCR alpha chain constant domain, 2nd CRI: CH1 (IgG1)
SEQ ID NO: 29 Amino acid sequence of TCRaLk, 3rd CRI: TCR alpha chain constant domain, 4th CRI: CLκ
SEQ ID NO: 30 Amino acid sequence of TCRaLL, 3rd CRI: TCR alpha chain constant domain, 4th CRI: CLλ
SEQ ID NO: 31 Amino acid sequence of TCRbH1, 1st CRI: TCR beta chain constant domain, 2nd CRI: CH1 (IgG1)
SEQ ID NO: 32 Amino acid sequence of TCRb 1Lk, 3rd CRI: TCR beta chain constant domain, 4th CRI: CLk
SEQ ID NO: 33 Amino acid sequence of TCRbLL, 3rd CRI: TCR beta chain constant domain, 4th CRI: CLλ
SEQ ID NO: 34 Amino acid sequence of VH13.7-CH2-CH31
SEQ ID NO: 35 Amino acid sequence of VL13.7-CH2-CH3κ
SEQ ID NO: 36 Amino acid sequence of scFv13.7-Hinge-CH2-CH31
SEQ ID NO: 37 Amino acid sequence of Hinge-CH2-CH3κ
SEQ ID NO: 38 Amino acid sequence of scFvhuU3-Hinge-CH2-CH3κ
SEQ ID NO: 39 Amino acid sequence of scFv3-43-Hinge-CH2-CH31
SEQ ID NO: 40 Amino acid sequence of scFhuMCSP-Hinge-CH2-CH31
SEQ ID NO: 41 Amino acid sequence of VH13.7-CH2-CH3k
SEQ ID NO: 42 Amino acid sequence of VL13.7-CH2-CH31
SEQ ID NO: 43 Amino acid sequence of VHCD3-CH2-CH3k-scFvHer3
SEQ ID NO: 44 Amino acid sequence of VLCD3-CH2-CH31-scFvHer3
SEQ ID NO: 45 Amino acid sequence of IgG1 CH3
SEQ ID NO: 46 Amino acid sequence of IgG2 CH3
SEQ ID NO: 47 Amino acid sequence of IgG3 CH3
SEQ ID NO: 48 Amino acid sequence of IgG4 CH3
SEQ ID NO: 49 Amino acid sequence of IgM CH4
SEQ ID NO: 50 Amino acid sequence of IgA1 CH3
SEQ ID NO: 51 Amino acid sequence of IgA2 CH3
SEQ ID NO: 52 Amino acid sequence of IgD CH3
SEQ ID NO: 53 Amino acid sequence of IgE CH4
SEQ ID NO: 54 Amino acid sequence of Igλ constant region
SEQ ID NO: 55 Amino acid sequence of Igλ constant region
SEQ ID NO: 56 Amino acid sequence of Igλ constant region
SEQ ID NO: 57 Amino acid sequence of TCR β1
SEQ ID NO: 58 Amino acid sequence of HLA-D β2

Figure 35:
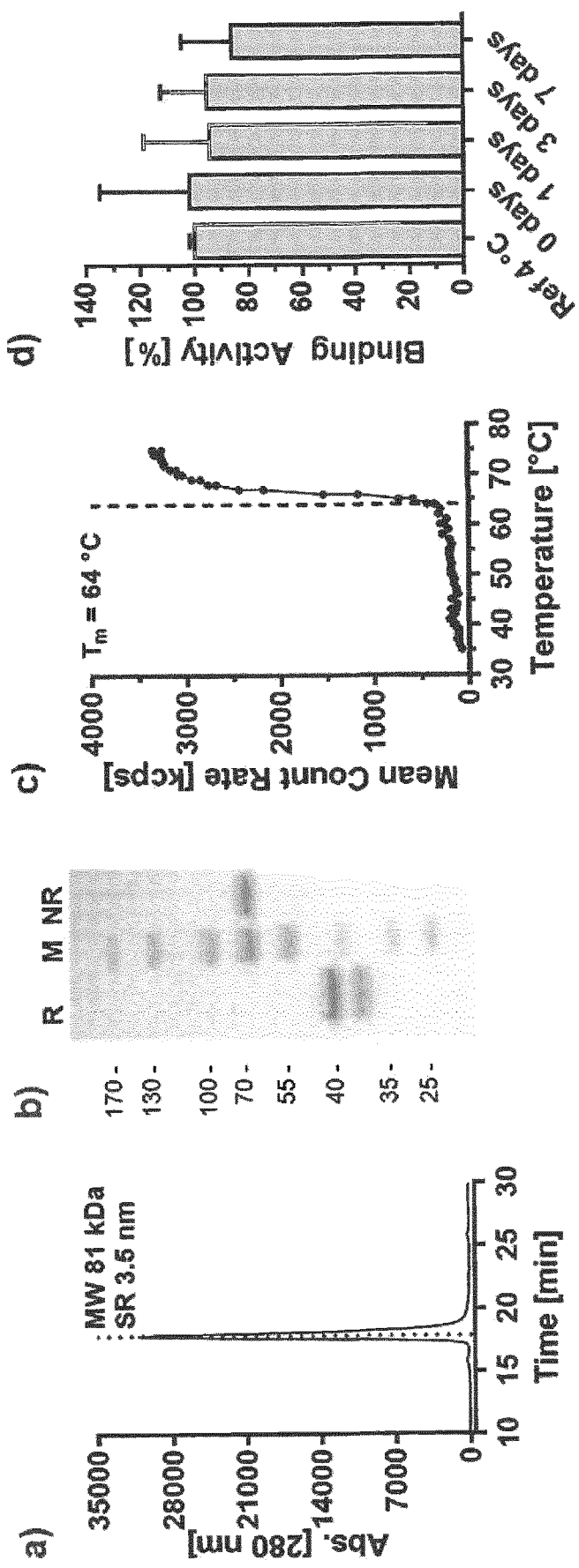

FIG. 35. Biochemical characterization of Fv13.7X-Fc1k. Fv13.7X-Fc1k was produced from a CHO cell pool after stable lentiviral transduction and purified by Protein A chromatography and subsequent preparative SEC. Characterization was performed by analytical SEC (a, TSKgel SuperSW mAb HR, Flow rate 0.5 ml/min, mobile phase Na2HPO4/NaH2PO4) and SDS-PAGE (b, NuPAGE™ 4-12% Bis-TRIS Midi Gel) under reducing (R) and non-reducing conditions (NR). M: Marker. c) The melting temperature was determined by dynamic light scattering and visual interpretation of the obtained results. Plasma stability analysis was performed after incubation in human plasma for the indicated time points followed by analysis of the $EC_{50}$ values of residual binding protein by ELISA (d).

Figure 36:
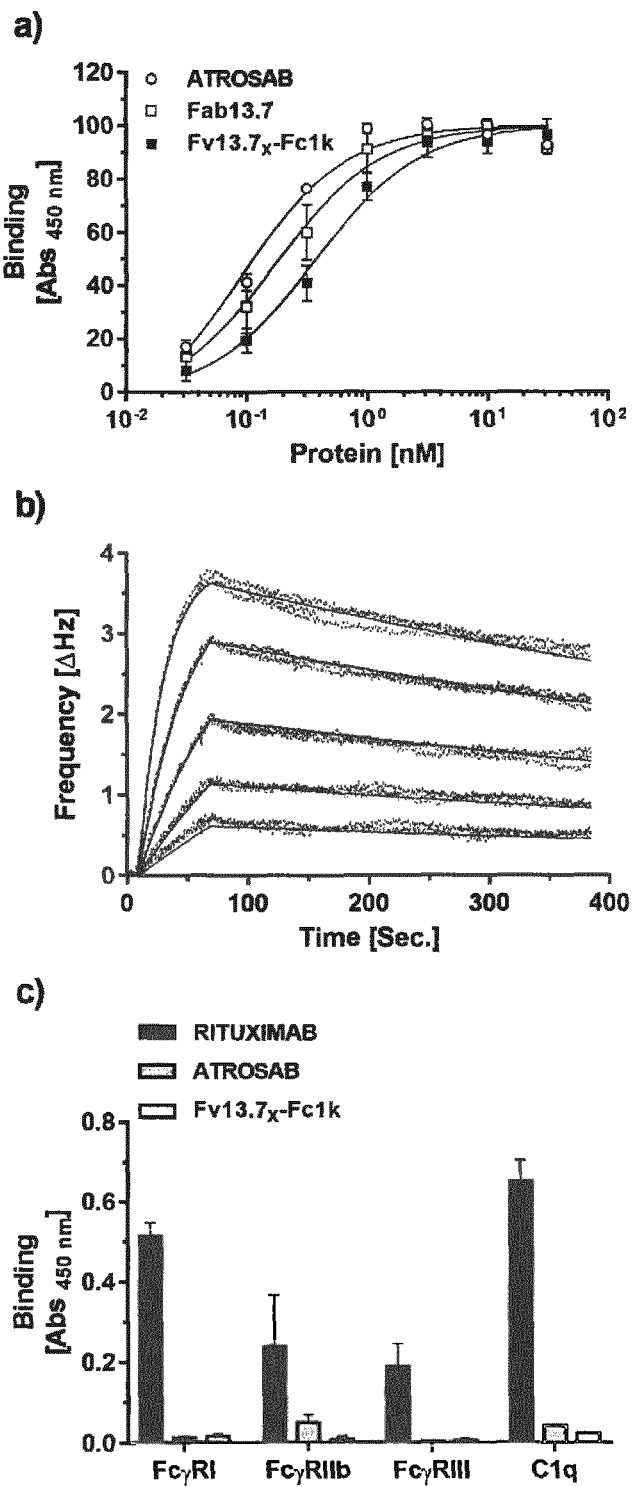

FIG. 36. Antigen and Fc receptor binding of Fv13.7X-Fc1k. Binding of Fv13.7X-Fc1k to human TNFR1-Fc was analyzed in ELISA (a, n=3, mean±SD) and QCM (b). Five concentrations between 128 nM and 4 nM were used to generate the kinetic data in b) and a one-to-one binding algorithm was employed for fitting. C) Binding of human Fc gamma Receptors I, IIb and III and the complement protein C1q to immobilized Fv13.7X-Fc1k was analyzed in ELISA. Rituximab (wild-type Fc part) and ATROSAB (silent Fc) were used as controls (n=2, mean±SD).

Figure 37:
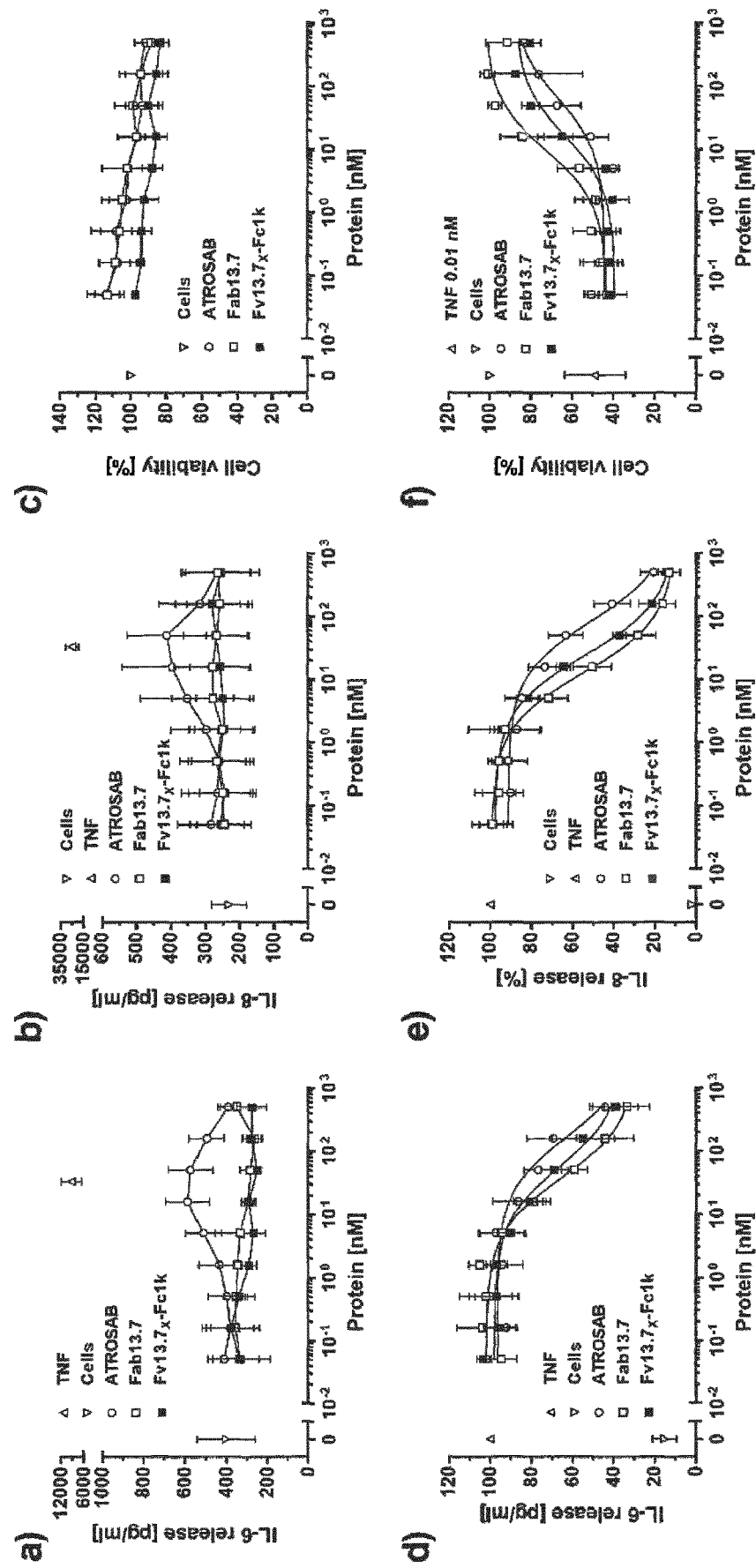

FIG. 37. Lack of agonistic and antagonistic bioactivity of Fv13.7X-Fc1k. The inherent lack of agonistic activity of Fv13.7X-Fc1k in terms of TNFR1 activation was demonstrated in three individual assays. A) IL 6 release from HeLa cells, b) IL-8 release from HT1080 cells and in a cell death induction assay using Kym 1 cells (c). The inhibitory potential of Fv13.7X-Fc1k was shown as well in an IL-6 release assay using HeLa cells (d), an IL-8 release assay using HT1080 cells (e) and in a cell death induction assay using Kym-1 cells (f), which were performed in the presence of a constant concentration of 0.1 nM TNF (d and e) or 0.01 nM TNF (f). Fab 13.7, ATROSAB and TNF alone served as control molecules for the activation of TNFR1 (TNF and ATROSAB in a, b and c) as well for the inhibition of TNF-induced TNFR1 activation (Fab 13.7 and ATROSAB in d, e and f). All graphs represent the mean of three individual Experiments, error bars indicate SD.

FIG. 38. Lack of agonistic bioactivity of Fv13.7X-Fc1k in the presence of anti-human IgG antibodies. The activation of TNFR1 on the surface of HT1080 cells by Fv13.7X-Fc1k in the presence of a constant concentration (ca. 15.8 nM) of three different anti-human IgG serum preparations (a, b and c) was determined by the detection IL-8 release into the culture supernatant. Cells alone and 33 nM TNF were used as controls. The agonistic effect of potentially crosslinking antibodies was compared to Fab 13.7 and ATROSAB. All experiments show Mean±SD of three individual experiments.

Figure 39:
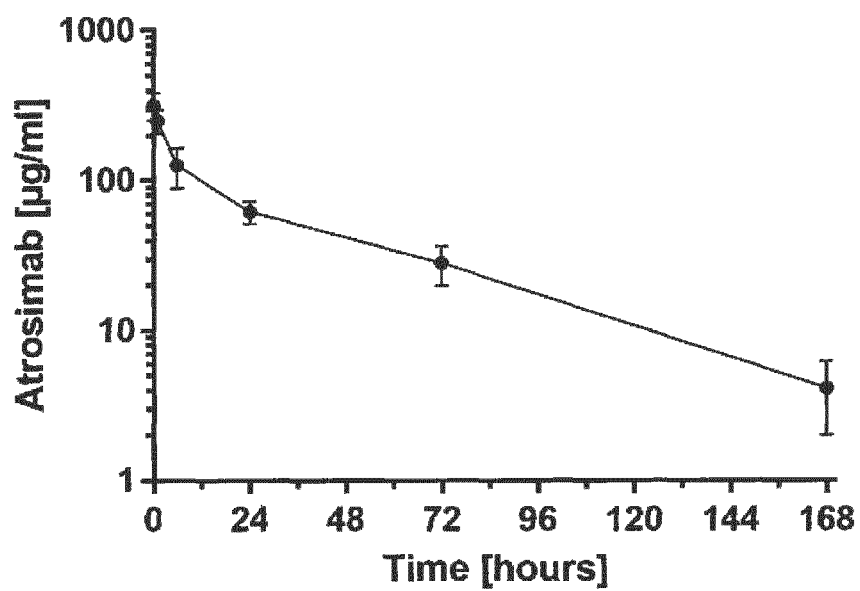

FIG. 39. Pharmacokinetic analysis of Fv13.7X-Fc1k. 400 µg of Fv13.7X-Fc1k were injected into C56BL/6J knock-in mice, carrying the gene of the human TNFR1 extra cellular domain connected to the mouse transmembrane and intracellular domains instead of the wild-type mouse gene. Remaining intact protein in the serum was determined by ELISA upon binding to TNFRI at the indicated time points. Shown are the mean±SD of five mice.

DETAILED DESCRIPTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kilbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

Definitions

The word "comprise", and variations such as "comprises" and "comprising", will be understood to imply the inclusion of a stated integer or step or group of integers or steps but not the exclusion of any other integer or step or group of integers or steps.

As used in this specification and the appended claims, the singular forms "a", "an", and "the" include plural referents, unless the content clearly dictates otherwise.

Concentrations, amounts, and other numerical data may be expressed or presented herein in a "range" format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "150 mg to 600 mg" should be interpreted to include not only the explicitly recited values of 150 mg to 600 mg, but to also include individual values and sub-ranges within the indicated range. Thus, included in this numerical range are individual values such as 150, 160, 170, 180, 190, . . . 580, 590, 600 mg and sub-ranges such as from 150 to 200, 150 to 250, 250 to 300, 350 to 600, etc. This same principle applies to ranges reciting only one numerical value. Furthermore, such an interpretation should apply regardless of the breadth of the range or the characteristics being described.

The term "about" when used in connection with a numerical value is meant to encompass numerical values within a range having a lower limit that is 5% smaller than the indicated numerical value and having an upper limit that is 5% larger than the indicated numerical value.

The term "nucleic acid" and "nucleic acid molecule" are used synonymously herein and are understood as single or double-stranded oligo- or polymers of deoxyribonucleotide or ribonucleotide bases or both. Nucleotide monomers are composed of a nucleobase, a five-carbon sugar (such as but not limited to ribose or 2'-deoxyribose), and one to three phosphate groups. Typically, a nucleic acid is formed through phosphodiester bonds between the individual nucleotide monomers. In the context of the present invention, the term nucleic acid includes but is not limited to ribonucleic acid (RNA) and deoxyribonucleic acid (DNA) molecules but also includes synthetic forms of nucleic acids comprising other linkages (e.g., peptide nucleic acids as described in Nielsen et al. (Science 254:1497-1500, 1991). Typically, nucleic acids are single- or double-stranded molecules and are composed of naturally occuring nucleotides. The depiction of a single strand of a nucleic acid also defines (at least partially) the sequence of the complementary strand. The nucleic acid may be single or double stranded, or may contain portions of both double and single stranded sequences. Exemplified, double-stranded nucleic acid molecules can have 3' or 5' overhangs and as such are not required or assumed to be completely double-stranded over their entire length. The nucleic acid may be obtained by biological, biochemical or chemical synthesis methods or any of the methods known in the art, including but not limited to methods of amplification, and reverse transcription of RNA. The term nucleic acid comprises chromosomes or chromosomal segments, vectors (e.g., expression vectors), expression cassettes, naked DNA or RNA polymer, primers, probes, cDNA, genomic DNA, recombinant DNA, cRNA, mRNA, tRNA, microRNA (miRNA) or small interfering RNA (siRNA). A nucleic acid can be, e.g., single-stranded, double-stranded, or triple-stranded and is not limited to any particular length. Unless otherwise indicated, a particular nucleic acid sequence comprises or encodes complementary sequences, in addition to any sequence explicitly indicated.

Nucleic acids may be degraded by endonucleases or exonucleases, in particular by DNases and RNases which can be found in the cell. It may, therefore, be advantageous to modify the nucleic acids of the invention in order to stabilize them against degradation, thereby ensuring that a high concentration of the nucleic acid is maintained in the cell over a long period of time. Typically, such stabilization can be obtained by introducing one or more internucleotide phosphorus groups or by introducing one or more non-phosphorus internucleotides. Accordingly, nucleic acids can be composed of non-naturally occurring nucleotides and/or modifications to naturally occurring nucleotides, and/or changes to the backbone of the molecule. Modified internucleotide phosphate radicals and/or non-phosphorus bridges in a nucleic acid include but are not limited to methyl phosphonate, phosphorothioate, phosphoramidate, phosphorodithioate and/or phosphate esters, whereas non-phosphorus internucleotide analogues include but are not limited to, siloxane bridges, carbonate bridges, carboxymethyl esters, acetamidate bridges and/or thioether bridges. Further examples of nucleotide modifications include but are not limited to: phosphorylation of 5' or 3' nucleotides to allow for ligation or prevention of exonuclease degradation/polymerase extension, respectively; amino, thiol, alkyne, or biotinyl modifications for covalent and near covalent attachments; fluorophores and quenchers; and modified bases such as deoxyInosine (dI), 5-Bromo-deoxyuridine (5-BromodU), deoxyUridine, 2-Aminopurine, 2,6-Diaminopurine, inverted dT, inverted Dideoxy-T, dideoxyCytidine (ddC 5-Methyl deoxyCytidine (5-Methyl dC), locked nucleic acids (LNA's), 5-Nitroindole, Iso-dC and -dG bases, 2'-O-Methyl RNA bases, Hydroxmethyl dC, 5-hydroxybutynl-2'-deoxyuridine, 8-aza-7-deazaguanosineand Fluorine Modified Bases. Thus, the nucleic acid can also be an artificial nucleic acid which includes but is not limited to polyamide or peptide nucleic acid (PNA), morpholino and locked nucleic acid (LNA), as well as glycol nucleic acid (GNA) and threose nucleic acid (TNA).

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

The term "polynucleotide", when used in the context of the present invention, refers to a nucleic acid of more than about 50 nucleotides in length, e.g. 51 or more nucleotides in length.

Polypeptides of the invention are prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method ofNarang et al. (Meth. Enzymol. 68:90-99, 1979); the phosphodiester method of Brown et al. (Meth. Enzymol. 68:109-151, 1979); the diethylphosphoramidite method of Beaucage et al. (Tetrahedron Lett. 22:1859-1862, 1981); the triester method of Matteucci et al. (J. Am. Chem. Soc. 103:3185-3191, 1981); automated synthesis methods; or the solid support method of U.S. Pat. No. 4,458,066, or other methods known to those skilled in the art.

As used herein, the term "vector" refers to a protein or a polynucleotide or a mixture thereof which is capable of being introduced or of introducing proteins and/or nucleic acids comprised therein into a cell. Examples of vectors include but are not limited to plasmids, cosmids, phages, viruses or artificial chromosomes. In particular, a vector is used to transport a gene product of interest, such as e.g. foreign or heterologous DNA into a suitable host cell. Vectors may contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Vectors may further encompass "expression control sequences" that regulate the expression of the gene of interest. Typically, expression control sequences are polypeptides or polynucleotides such as but not limited to promoters, enhancers, silencers, insulators, or repressors. In a vector comprising more than one polynucleotide encoding for one or more gene products of interest, the expression may be controlled together or separately by one or more expression control sequences. More specifically, each polynucleotide comprised on the vector may be control by a separate expression control sequence or all polynucleotides comprised on the vector may be controlled by a single expression control sequence. Polynucleotides comprised on a single vector controlled by a single expression control sequence may form an open reading frame. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized.

The term "amino acid" generally refers to any monomer unit that comprises a substituted or unsubstituted amino group, a substituted or unsubstituted carboxy group, and one or more side chains or groups, or analogs of any of these groups. Exemplary side chains include, e.g., thiol, seleno, sulfonyl, alkyl, aryl, acyl, keto, azido, hydroxyl, hydrazine, cyano, halo, hydrazide, alkenyl, alkynl, ether, borate, boronate, phospho, phosphono, phosphine, heterocyclic, enone, imine, aldehyde, ester, thioacid, hydroxylamine, or any combination of these groups. Other representative amino acids include, but are not limited to, amino acids comprising photoactivatable cross-linkers, metal binding amino acids, spin-labeled amino acids, fluorescent amino acids, metal-containing amino acids, amino acids with novel functional groups, amino acids that covalently or noncovalently interact with other molecules, photocaged and/or photoisomerizable amino acids, radioactive amino acids, amino acids comprising biotin or a biotin analog, glycosylated amino acids, other carbohydrate modified amino acids, amino acids comprising polyethylene glycol or polyether, heavy atom substituted amino acids, chemically cleavable and/or photocleavable amino acids, carbon-linked sugar-containing amino acids, redox-active amino acids, amino thioacid containing amino acids, and amino acids comprising one or more toxic moieties. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). In cases where "X" residues are undefined, these should be defined as "any amino acid." The structures of these twenty natural amino acids are shown in, e.g., Stryer et al., Biochemistry, 5th ed., Freeman and Company (2002). Additional amino acids, such as selenocysteine and pyrrolysine, can also be genetically coded for (Stadtman (1996) "Selenocysteine," Annu Rev Biochem. 65:83-100 and Ibba et al. (2002) "Genetic code: introducing pyrrolysine," Curr Biol. 12(13):R464-R466). The term "amino acid" also includes unnatural amino acids, modified amino acids (e.g., having modified side chains and/or backbones), and amino acid analogs. See, e.g., Zhang et al. (2004) "Selective incorporation of 5-hydroxytryptophan into proteins in mammalian cells," Proc. Natl. Acad. Sci. U.S.A. 101(24):8882-8887, Anderson et al. (2004) "An expanded genetic code with a functional quadruplet codon" Proc. Natl. Acad. Sci. U.S.A. 101(20):7566-7571, Ikeda et al. (2003) "Synthesis of a novel histidine analogue and its efficient incorporation into a protein in vivo," Protein Eng. Des. Sel. 16(9):699-706, Chin et al. (2003) "An Expanded Eukaryotic Genetic Code," Science 301(5635):964-967, James et al. (2001) "Kinetic characterization of ribonuclease S mutants containing photoisomerizable phenylazophenylalanine residues," Protein Eng. Des.

Sel. 14(12):983-991, Kohrer et al. (2001) "Import of amber and ochre suppressor tRNAs into mammalian cells: A general approach to site-specific insertion of amino acid analogues into proteins," Proc. Natl. Acad. Sci. U.S.A. 98(25): 14310-14315, Bacher et al. (2001) "Selection and Characterization of *Escherichia coli* Variants Capable of Growth on an Otherwise Toxic Tryptophan Analogue," J. Bacteriol. 183(18):5414-5425, Hamano-Takaku et al. (2000) "A Mutant *Escherichia coli* Tyrosyl-tRNA Synthetase Utilizes the Unnatural Amino Acid Azatyrosine More Efficiently than Tyrosine," J. Biol. Chem. 275(51):40324-40328, and Budisa et al. (2001) "Proteins with {beta}-(thienopyrrolyl) alanines as alternative chromophores and pharmaceutically active amino acids," Protein Sci. 10(7): 1281-1292. Amino acids can be merged into peptides, polypeptides, or proteins.

In the context of the present invention, the term "peptide" refers to a short polymer of amino acids linked by peptide bonds. It has the same chemical (peptide) bonds as proteins, but is commonly shorter in length. The shortest peptide is a dipeptide, consisting of two amino acids joined by a single peptide bond. There can also be a tripeptide, tetrapeptide, pentapeptide, etc. Typically, a peptide has a length of up to 8, 10, 12, 15, 18 or 20 amino acids. A peptide has an amino end and a carboxyl end, unless it is a cyclic peptide.

In the context of the present invention, the term "polypeptide chain" or "amino acid chain "refers to a single linear chain of amino acids bonded together by peptide bonds and typically comprises at least about 21 amino acids.

The term "protein complex" as used herein, refers to a group of two or more associated polypeptide or amino acid chains. The different polypeptide chains may have different functions. Protein complexes are a form of quaternary structure. Proteins in a protein complex are linked by noncovalent protein-protein interactions, and optionally additionally by covalent bonds, e.g. formed between two adjacent Cys residues in two different polypeptide chains. Depending on the stability of the non-covalent and optionally the covalent bonds different protein complexes have different degrees of stability over time.

Figure 3:
Figure 4:
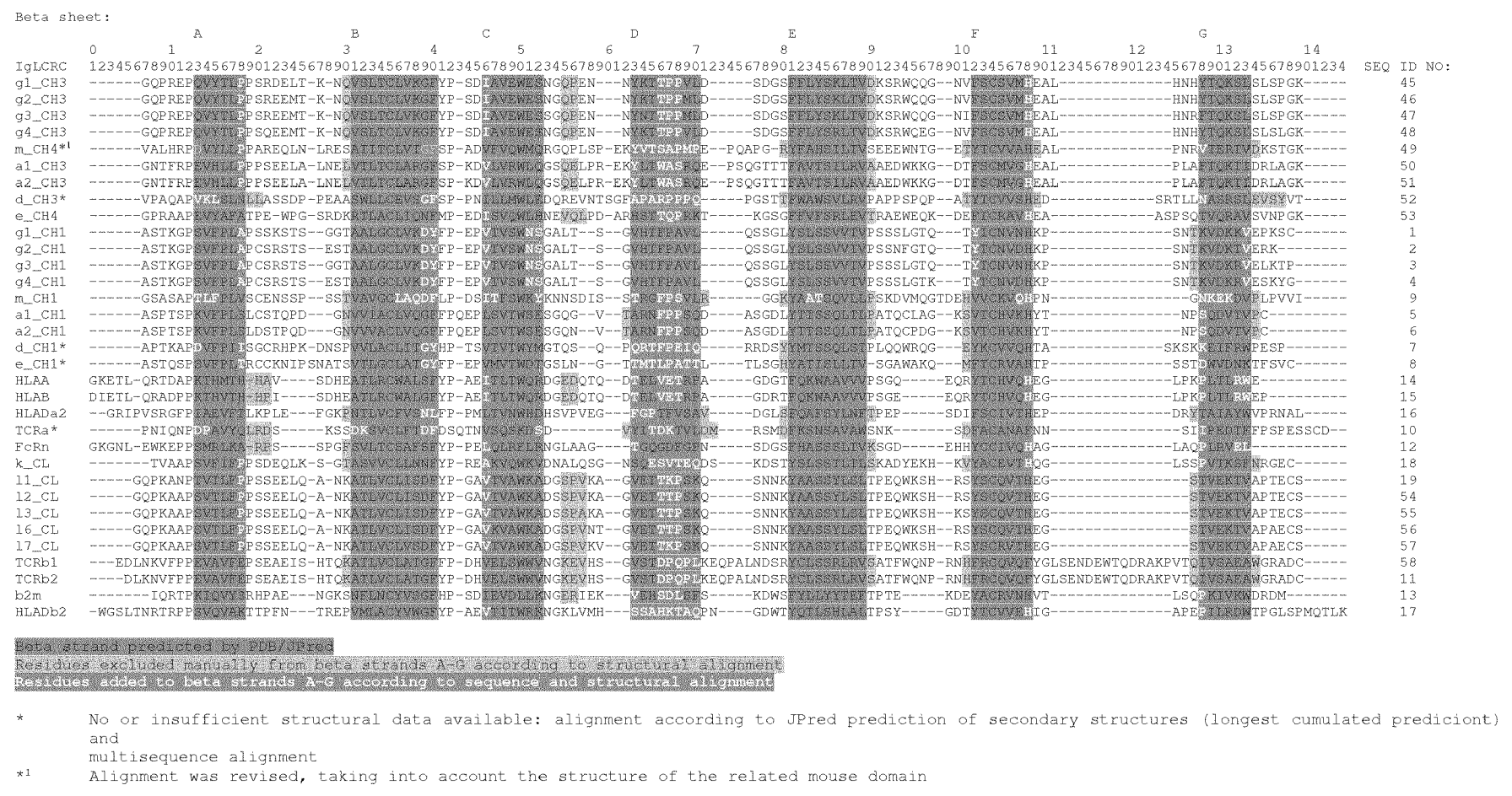
Figure 5:
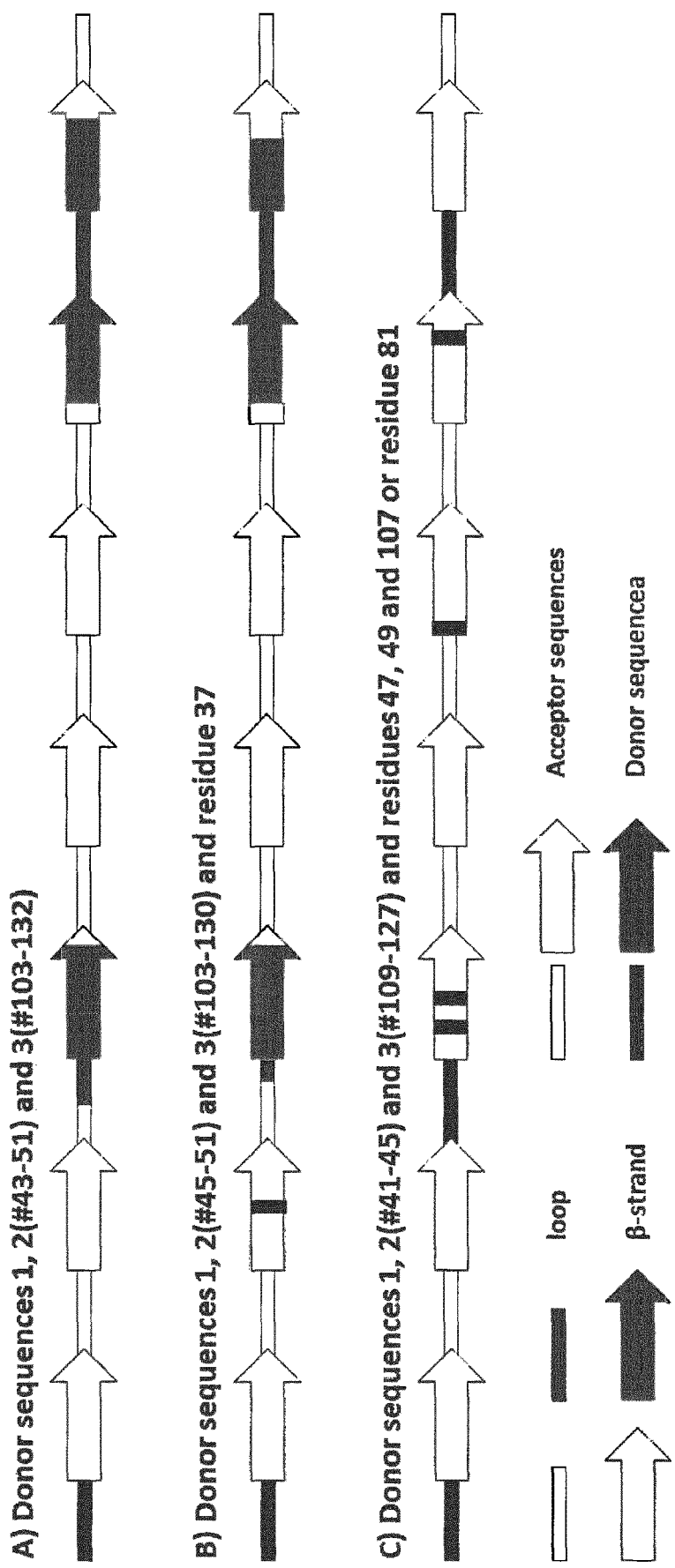

The term "human constant region of an immunoglobulin or an immunoglobulin-like protein (CRI)" is used in the context of the present invention to refer to an amino acid sequence of between 60 to 150 amino acid length comprising seven antiparallel beta strands forming a sandwich-like globular structure of two cysteine-connected beta sheets. An exemplary sheet structure is shown in FIG. 3. The amino acid sequences of the most preferred CRIs to be used in the context of the present invention are indicated in FIG. 4. This term also comprises variants of the specifically indicated sequences in as long as the variants can still fold into a beta sheet-based Ig domain-like sandwich conformation.

The term "heterodimerizing region" (HRI, HRII) as used herein, refers to an amino acid sequence stretch within the respective larger amino acid chains I and II which specifically bind to each other, preferably under physiological conditions and which are, thus responsible for heterodimerization of amino acid chain I and II. The term heterodimerizing region also implies that the amino acid sequence of amino acid chain I and II are different. As for the protein complex defined above, the binding between HRI and HRII is primarily mediated by non-covalent interaction. However, if HRI and HRII each comprise a Cys residue in adjacent positions within the binding interface of HRI and HRII covalent bonds between these Cys residues can stabilize the binding between HRI and HRII. HRI and HRII each form a beta sheet structure similar to the one shown in FIG. 3.

The term "Fc-function" is used to refer to the ability of immunoglobulins to stimulate phagocytic or cytotoxic cells to destroy microbes, or infected cells by antibody-mediated phagocytosis, antibody-dependent cell-mediated cytotoxicity or complement-mediated cytolysis. This function is based on the binding of the antibody to Fc receptors present on the surface of certain cells of the immune cells, in particular B lymphocytes, follicular dendritic cells, natural killer cells, macrophages, neutrophils, eosinophils, basophils, human platelets, and mast cells. "Fe function" further refers to the ability to bind to the neonatal Fc receptor (FcRn) mediating a prolonged half-life. The skilled person is well aware how to measure Fc function of an antibody of antibody fragment. The Fc-function of immunoglobulins primarily in the CH2 and/or CH3 domain, in particular of IgGs.

In the context of present invention, the "primary structure" of a protein or polypeptide is the sequence of amino acids in the polypeptide chain. The "secondary structure" in a protein is the general three-dimensional form of local segments of the protein. It does not, however, describe specific atomic positions in three-dimensional space, which are considered to be tertiary structure. In proteins, the secondary structure is defined by patterns of hydrogen bonds between backbone amide and carboxyl groups. The "tertiary structure" of a protein is the three-dimensional structure of the protein determined by the atomic coordinates. The "quaternary structure" is the arrangement of multiple folded or coiled protein or polypeptide molecules in a multi-subunit complex.

The term "folding" or "protein folding" as used herein refers to the process by which a protein assumes its three-dimensional shape or conformation, i.e. whereby the protein is directed to form a specific three-dimensional shape through noncovalent and/or covalent interactions, such as but not limited to hydrogen bonding, metal coordination, hydrophobic forces, van der Waals forces, pi-pi interactions, electrostatic effects and/or intramolecular Cys bonds. The term "folded protein" thus, refers to a protein its three-dimensional shape, such as its secondary, tertiary, or quaternary structure.

The term "beta strand" as used in the context of the present invention refers to a 5 to 10 amino acid long section within a polypeptide chain in which the torsion angle of N—Cα-C—N in the backbone is about 120 degrees. Beta strands within a given protein sequence can be predicted after (multiple) sequence alignment (e.g. using Clustal omega) by retrieving annotations from pdb files. If not all 7 beta strands are assigned (e.g. indicated with a asterisk in FIG. 4) prediction of beta strands can be additionally performed using commonly available software tools like JPred (for alignment in FIG. 4, the longest cumulated prediction using default settings was used). Start and end positions of the seven beta strands can be confirmed by additional structural alignment of PDB files using pyMol. The multiple sequence alignment might thereby be refined according to structurally conserved residues upon (i) the inclusion of formally not assigned residues into the strands or (ii) the exclusion of formerly assigned residues from strands, as well as (iii) the deletion of gaps inside of the beta strands, introduced into the sequences by multi sequence alignment, or (iv) by the insertion of novel gaps outside of the beta strands (as performed for 4 exceptions in FIG. 4, d_CH3: position 111; m_CH1: position #72; HLAA/HLAB: position #60). Inserted/elongated or deleted/curtailed gap positions should be compensated for by deletion or insertion of gap positions in the following already existing gap, introduced into the sequences during multi sequence alignment, respectively, in order to maintain the alignment of the sequences in regions located closer to the c-terminus. Hence, the seven beta strands can be defined by these means as follows:

A) the six residues subsequent to a conserved proline residue N-terminal to the predicted first beta strand (positions 13-18 in FIG. 4).

B) the four residues N-terminally and the five residues C-terminally neighboring a conserved cysteine residue included in the second predicted beta strand (positions 13-18 in FIG. 4 31-40).

C) the four residues N-terminally and the two residues C-terminally neighboring a conserved tryptophan residue included in the third predicted beta strand (positions 46-52 in FIG. 4).

D) positions 63-70 in FIG. 4, however, connection to a conserved residue throughout the whole alignment was not feasible.

E) eight residues starting with a conserved Tyrosine/Phenylalanine residue, located to the beginning or N-terminally to fourth predicted beta strand (positions 81-89 in FIG. 4).

F) was defined as the two residues N-terminally and the four residues C-terminally neighboring a conserved cysteine residue included in the sixth predicted beta strand (positions 102-108 in FIG. 4

G) positions 128-133 in FIG. 4, however, connection to a conserved residue throughout the whole alignment was not feasible.

For a given constant region of an immunoglobulin or immnunoglobulin-like protein (CRI) the skilled person can, thus easily determine the seven beta strands. Alternatively, a given CRI not included in FIG. 4 can be added to the alignment of FIG. 4. Beta strand A spans IgLCRC positions 13 to 18, beta strand B spans IgLCRC positions 31 to 40, beta strand C spans IgLCRC positions 46 to 52, beta strand D spans IgLCRC positions 63 to 70, beta strand E spans IgLCRC positions 81 to 89, beta strand F spans IgLCRC positions 102 to 108, beta strand G spans IgLCRC positions 128 to 133.

The term "beta sheet" as used in the context of the present invention refers to antiparallel orientated ß-strands which form the beta sheet. The beta sheet is a common motif of regular secondary structure in proteins. Because peptide chains have a directionality conferred by their N-terminus and C-terminus, β-strands too can be said to be directional. They are usually represented in protein topology diagrams by an arrow pointing toward the C-terminus. Adjacent β-strands can form hydrogen bonds in antiparallel, parallel, or mixed arrangements. In an antiparallel arrangement, the successive β-strands alternate directions so that the N-terminus of one strand is adjacent to the C-terminus of the next. This is the arrangement that produces the strongest inter-strand stability because it allows the inter-strand hydrogen bonds between carbonyls and amines to be planar, which is their preferred orientation. A β structure is characterized by long extended polypeptide chains. The amino acid composition of β strands tends to favor hydrophobic (water fearing) amino acid residues. The side chains of these residues tend to be less soluble in water than those of more hydrophilic (water loving) residues. β structures tend to be found inside the core structure of proteins where the hydrogen bonds between strands are protected from competition with water molecules. As is apparent from FIG. 3 the seven antiparallel beta strands comprised in each CRI and thus also in HRI and HRII each derived from two CRIs form a beta sheet structure.

The term "intervening regions" as used in the context of the human immunoglobulin or human immunoglobulin-like protein refers to the amino acid chains between two beta strands. The intervening regions are less structured, e.g. form loops, and may comprise short α-helices. for a given CRI the skilled person can determine intervening regions by structural and/or sequence alignment. A CRI not already comprised in FIG. 4 can be added to the alignment. Once aligned intervening regions "b", "c", "d", "e", "f" and "g" span IgLCRC positions 19 to 30, IgLCRC positions 41 to 45, IgLCRC positions 53 to 62, IgLCRC positions 71 to 80, IgLCRC positions 90 to 101, and IgLCRC positions 109 to 127, respectively. Each intervening region can comprise one or more amino acid deletion in as long as the seven antiparallel beta strands can still form a beta sheet. Thus, an intervening regions can have less or more amino acids then suggested by the IgLCRC positions of that intervening region. The N- and C-terminal amino acid of the intervening region and, thus its length is determined by the N- and C-terminal amino acid of the beta sheets of the human immunoglobulin or human immunoglobulin-like proteins of the invention. Accordingly, intervening region "b" may have a length of between 5 to 12, in particular 6 to 11, in particular 7 to 10 and more particularly 8 to 9 amino acids, intervening region "c" may have a length of between 1 to 5, in particular 2 to 4, and more particularly 3 amino acids, intervening region "d" may have a length of between 1 to 10, in particular 3 to 8, and more particularly 4 to 6 amino acids, intervening region "e" may have a length of between 1 to 10, in particular 2 to 8, and more particularly 4 to 6 amino acids, intervening region "f" may have a length of between 1 to 12, in particular 3 to 10, and more particularly 5 to 8 amino acids, and intervening region "g" may have a length of between 4 to 19, in particular 5 to 15, and more particularly 7 to 11 amino acids. As noted the intervening regions of some human immunoglobulin or human immunoglobulin-like protein may be longer than the typical lengths indicated above. If an intervening region comprises more amino acids than IgLCRC positions for that intervening regions, e.g. the intervening region "b" of a particular human immunoglobulin or human immunoglobulin-like protein may have a length of 15 amino acids, while intervening region "b" only span IgLCRC positions 19 to 30. In this case the amino acids of the intervening regions are aligned and the excess amino acids that do not align well are given an IgLCRC position with the additional designaton "a", "b" etc. Thus, an intervening region "b" of 15 amino acids may span the following IgLCRC designations: 19, 19a, 19b, 19c, and 20 to 30.

The term "N-terminal region a" and "C-terminal region h", respectively refer to a less structured part at the respective ends of the CRI and the HRI and HRII derived therefrom. The N-terminal region a may span IgLCRC positions 1 to 12 (see FIG. 4). In particular the length may be between 4 to 12 amino acids, in particular between 5 to 10, more particularly between 6 to 8 amino acids. The C-terminal region h may span IgLCRC positions 134 to 144 (see FIG. 4). In particular the length may be between 4 to 11 amino acids, in particular between 5 to 10, more particularly between 6 to 8 amino acids.

The term "fragment" used herein refers to naturally occurring fragments (e.g. splice variants) as well as artificially constructed fragments, in particular to those obtained by gene-technological means. Typically, a fragment has a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, or 300 amino acids at its N-terminus and/or at its C-terminus and/or internally as compared to the parent polypeptide, preferably at its N-terminus, at its N- and C-terminus, or at its C-terminus.

An "epitope", also known as antigenic determinant, is the segment of a macromolecule that is recognized by the immune system, specifically by antibodies, B cells, or T cells. Such epitope is that part or segment of a macromolecule capable of binding to an antibody or antigen-binding fragment thereof. In this context, the term "binding" preferably relates to a specific binding. In the context of the present invention it is preferred that the term "epitope" refers to the segment of protein or polyprotein that is recognized by the immune system. Epitopes usually consist of chemically active surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents.

As used herein, a "conformational epitope" refers to an epitope of a linear macromolecule (e.g. a polypeptide) that is formed by the three-dimensional structure of said macromolecule. In the context of the present application, a "conformational epitope" is a "discontinuous epitope", i.e. the conformational epitope on the macromolecule (e.g. a polypeptide) which is formed from at least two separate regions in the primary sequence of the macromolecule (e.g. the amino acid sequence of a polypeptide). In other words, an epitope is considered to be a "conformational epitope" in the context of the present invention, if the epitope consists of at least two separate regions in the primary sequence to which a binding moiety of the invention (e.g. an antibody or an antigen-binding fragment thereof) binds simultaneously, wherein these at least two separate regions are interrupted by one more region in the primary sequence to which a binding moiety of the invention does not bind. In particular, such a "conformational epitope" is present on a polypeptide, and the two separate regions in the primary sequence are two separate amino acid sequences to which a binding moiety of the invention (e.g. an antibody or an antigen-binding fragment thereof) binds, wherein these at least two separate amino acid sequences are interrupted by one more amino acid sequences in the primary sequence to which a binding moiety of the invention does not bind. In particular, the interrupting amino acid sequence is a contiguous amino acid sequence comprising two or more amino acids to which the binding moiety does not bind. The at least two separate amino acid sequences to which a binding moiety of the invention binds are not particularly limited with regard to their length. Such a separate amino acid sequence may consist of only one amino acid as long as the total number of amino acids within said at least two separate amino acid sequences is sufficiently large to effect specific binding between the binding moiety and the conformational epitope.

A "paratope" is the part of an antibody that recognizes the epitope. In the context of the present invention, a "paratope" is the part of a binding moiety (e.g. an antibody or antigen-binding fragment thereof) as described herein that recognizes the epitope.

A "peptide linker" in the context of the present invention refers to an amino acid sequence which sterically separates two parts or moieties of a complex, e.g. two peptides or proteins. Typically such linker consists of between 1 and 100 amino acids having a minimum length of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids, and a maximum length of at least 100, 95, 90, 85, 80, 75, 70, 65, 60, 55, 50, 45, 40, 35, 34, 33, 32, 31, 30, 29, 28, 27, 26, 25, 24, 23, 22, 21, 20, 19, 18, 17, 16, or 15 amino acids or less. The indicated preferred minimum and maximum lengths of the peptide linker according to the present invention may be combined, if such a combination makes mathematically sense, e.g. such linker may consist of 1-15, or 12-40, or 25-75, or 1-100 amino acids. Peptide linkers may also provide flexibility among the two moieties that are linked together. Such flexibility is generally increased if the amino acids are small. Accordingly, flexible peptide linkers comprise an increased content of small amino acids, in particular of glycins and/or alanines, and/or hydrophilic amino acids such as serines, threonines, asparagines and glutamines. Preferably, more than 20%, 30%, 40%, 50%, 60% or more of the amino acids of the peptide linker are small amino acids.

As used herein, the term "variant" is to be understood as a polypeptide or polynucleotide which differs in comparison to the polypeptide or polynucleotide from which it is derived by one or more changes in its length or sequence. The polypeptide or polynucleotide from which a polypeptide or polynucleotide variant is derived is also known as the parent polypeptide or polynucleotide. The term "variant" comprises "fragments" or "derivatives" of the parent molecule. Typically, "fragments" are smaller in length or size than the parent molecule, whilst "derivatives" exhibit one or more differences in their sequence in comparison to the parent molecule. Also encompassed are modified molecules such as but not limited to post-translationally modified proteins (e.g. glycosylated, biotinylated, phosphorylated, ubiquitinated, palmitoylated, or proteolytically cleaved proteins) and modified nucleic acids such as methylated DNA. Also mixtures of different molecules such as but not limited to RNA-DNA hybrids, are encompassed by the term "variant". Typically, a variant is constructed artificially, preferably by gene-technological means, whilst the parent protein or polynucleotide is a wild-type protein or polynucleotide, or a consensus sequence thereof. However, also naturally occurring variants are to be understood to be encompassed by the term "variant" as used herein. Further, the variants usable in the present invention may also be derived from homologs, orthologs, or paralogs of the parent molecule or from artificially constructed variant, provided that the variant exhibits at least one biological activity of the parent molecule, i.e. is functionally active. In particular, the term "peptide variant", "polypeptide variant", "protein variant" is to be understood as a peptide, polypeptide, or protein which differs in comparison to the peptide, polypeptide, or protein from which it is derived by one or more changes in the amino acid sequence. The peptide, polypeptide, or protein, from which a peptide, polypeptide, or protein variant is derived, is also known as the parent peptide, polypeptide, or protein. Further, the variants usable in the present invention may also be derived from homologs, orthologs, or paralogs of the parent peptide, polypeptide, or protein or from artificially constructed variant, provided that the variant exhibits at least one biological activity of the parent peptide, polypeptide, or protein. The changes in the amino acid sequence may be amino acid exchanges, insertions, deletions, N-terminal truncations, or C-terminal truncations, or any combination of these changes, which may occur at one or several sites.

The "percentage of sequences identity" is determined by comparing two optimally aligned sequences over a comparison window, wherein the portion of the sequence in the comparison window can comprise additions or deletions (i.e.

gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" in the context of two or more nucleic acids or polypeptide sequences, refers to two or more sequences or subsequences that are the same, i.e. comprise the same sequence of nucleotides or amino acids. Sequences are "substantially identical" to each other if they have a specified percentage of nucleotides or amino acid residues that are the same (e.g., at least 70%, at least 75%, at least 80, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity over a specified region), when compared and aligned for maximum correspondence over a comparison window, or designated region as measured using one of the following sequence comparison algorithms or by manual alignment and visual inspection. These definitions also refer to the complement of a test sequence. Accordingly, the term "at least 80% sequence identity" is used throughout the specification with regard to polypeptide and polynucleotide sequence comparisons. This expression preferably refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide.

For term "sequence comparison" refers to the process wherein one sequence acts as a reference sequence, to which test sequences are compared. When using a sequence comparison algorithm, test and reference sequences are entered into a computer, if necessary subsequence coordinates are designated, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters. In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence indicated by SEQ ID, if not specifically indicated otherwise.

In a sequence alignment, the term "comparison window" refers to those stretches of contiguous positions of a sequence which are compared to a reference stretch of contiguous positions of a sequence having the same number of positions. The number of contiguous positions selected may range from 4 to 1000, i.e. may comprise 4, 5, 10, 20, 30, 40, 50, 60, 70, 80, 90, 100, 150, 200, 250, 300, 350, 400, 450, 500, 550, 600, 650, 700, 750, 800, 850, 900, 950, or 1000 contiguous positions. Typically, the number of contiguous positions ranges from about 20 to 800 contiguous positions, from about 20 to 600 contiguous positions, from about 50 to 400 contiguous positions, from about 50 to about 200 contiguous positions, from about 100 to about 150 contiguous positions.

Methods of alignment of sequences for comparison are well known in the art. Optimal alignment of sequences for comparison can be conducted, for example, by the local homology algorithm of Smith and Waterman (Adv. Appl. Math. 2:482, 1970), by the homology alignment algorithm of Needleman and Wunsch (J. Mol. Biol. 48:443, 1970), by the search for similarity method of Pearson and Lipman (Proc. Natl. Acad. Sci. USA 85:2444, 1988), by computerized implementations of these algorithms (e.g., GAP, BEST-FIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)). Algorithms suitable for determining percent sequence identity and sequence similarity are the BLAST and BLAST 2.0 algorithms, which are described in Altschul et al. (Nuc. Acids Res. 25:33 89-402, 1977), and Altschul et al. (J. Mol. Biol. 215:403-10, 1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands. The BLAST algorithm also performs a statistical analysis of the similarity between two sequences (see, e.g., Karlin and Altschul, Proc. Natl. Acad. Sci. USA 90:5873-87, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

Semi-conservative and especially conservative amino acid substitutions, wherein an amino acid is substituted with a chemically related amino acid are preferred. Typical substitutions are among the aliphatic amino acids, among the amino acids having aliphatic hydroxyl side chain, among the amino acids having acidic residues, among the amide derivatives, among the amino acids with basic residues, or the amino acids having aromatic residues. Typical semi-conservative and conservative substitutions are:

| Amino | Conservative | Semi-conservative |
|---|---|---|
| A | G; S; T | N; V; C |
| C | A; V; L | M; I; F; G |
| D | E; N; Q | A; S; T; K; R; H |
| E | D; Q; N | A; S; T; K; R; H |
| F | W; Y; L; M; H | I; V; A |
| G | A | S; N; T; D; E; N; Q |
| H | Y; F; K; R | L; M; A |
| I | V; L; M; A | F; Y; W; G |
| K | R; H | D; E; N; Q; S; T; A |
| L | M; I; V; A | F; Y; W; H; C |
| M | L; I; V; A | F; Y; W; C; |
| N | Q | D; E; S; T; A; G; K; R |
| P | V; I | L; A; M; W; Y; S; T; C; F |
| Q | N | D; E; A; S; T; L; M; K; R |
| R | K; H | N; Q; S; T; D; E; A |
| S | A; T; G; N | D; E; R; K |
| T | A; S; G; N; V | D; E; R; K; I |
| V | A; L; I | M; T; C; N |
| W | F; Y; H | L; M; I; V; C |
| Y | F; W; H | L; M; I; V; C |

Changing from A, F, H, I, L, M, P, V, W or Y to C is semi-conservative if the new cysteine remains as a free thiol. Furthermore, the skilled person will appreciate that glycines at sterically demanding positions should not be substituted and that P should not be introduced into parts of the protein which have an alpha-helical or a beta-sheet structure.

A tag (or marker or label) is any kind of substance which is able to indicate the presence of another substance or complex of substances. The marker can be a substance that is linked to or introduced in the substance to be detected. Detectable markers are used in molecular biology and biotechnology to detect e.g. a protein, a product of an enzymatic reaction, a second messenger, DNA, interactions of molecules etc. Examples of suitable tags or labels include fluorophores, chromophores, radiolabels, metal colloids, enzymes, or chemiluminescent or bioluminescent molecules. In the context of the present invention suitable tags are preferably protein tags whose peptide sequences is genetically grafted into or onto a recombinant protein. Protein tags may e.g. encompass affinity tags, solubilization tags, chromatography tags, epitope tags, or Fluorescence tags.

"Affinity tags" are appended to proteins so that the protein can be purified from its crude biological source using an affinity technique. These include chitin binding protein (CBP), maltose binding protein (MBP), and glutathione-S-transferase (GST). The poly(His) tag is a widely used protein tag which binds to metal matrices.

"Solubilization tags" are used, especially for recombinant proteins expressed in chaperone-deficient species to assist in the proper folding in proteins and keep them from precipitating. These include thioredoxin (TRX) and poly(NANP). Some affinity tags have a dual role as a solubilization agent, such as MBP, and GST.

"Chromatography tags" are used to alter chromatographic properties of the protein to afford different resolution across a particular separation technique. Often, these consist of polyanionic amino acids, such as FLAG-tag.

The term "epitope tags" as used in the context of the present invention are short peptide sequences which are chosen because high-affinity antibodies can be reliably produced in many different species. These are usually derived from viral genes, which explain their high immunoreactivity. Epitope tags include V5-tag, Myc-tag, and HA-tag. These tags are particularly useful for western blotting, immunofluorescence and immunoprecipitation experiments, although they also find use in antibody purification.

"Fluorescence tags" are used to give visual readout on a protein. GFP and its variants are the most commonly used fluorescence tags. More advanced applications of GFP include using it as a folding reporter (fluorescent if folded, colourless if not). Further examples of fluorophores include fluorescein, rhodamine, and sulfoindocyanine dye Cy5.

The term "binding" according to the invention preferably relates to a specific binding. The term "binding affinity" generally refers to the strength of the sum total of noncovalent interactions between a single binding site of a molecule (e.g., an antibody) and its binding partner (e.g., target or antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). "Specific binding" means that a binding moiety (e.g. an antibody) binds stronger to a target such as an epitope for which it is specific compared to the binding to another target. A binding moiety binds stronger to a first target compared to a second target if it binds to the first target with a dissociation constant ($K_D$) which is lower than the dissociation constant for the second target. The dissociation constant ($K_D$) for the target to which the binding moiety binds specifically is more than 10-fold, preferably more than 20-fold, more preferably more than 50-fold, even more preferably more than 100-fold, 200-fold, 500-fold or 1000-fold lower than the dissociation constant ($K_D$) for the target to which the binding moiety does not bind specifically.

Accordingly, the term "$K_D$" (measured in "mol/L", sometimes abbreviated as "M") is intended to refer to the dissociation equilibrium constant of the particular interaction between a binding moiety (e.g. an antibody or fragment thereof) and a target molecule (e.g. an antigen or epitope thereof). Affinity can be measured by common methods known in the art, including but not limited to surface plasmon resonance based assay (such as the BIAcore assay); quartz crystal microbalance assays (such as Attana assay); enzyme-linked immunoabsorbent assay (ELISA); and competition assays (e.g. RIA's). Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

Typically, antibodies or antibody mimetics included in amino acid chains I and/or II bind with a sufficient binding affinity to their target, for example, with a $K_D$ value of between 500 nM-1 pM, i.e. 500 nM, 450 nM, 400 nM, 350 nM, 300 nM, 250 nM, 200 nM, 150 nM, 100 nM, 50 nM, 10 nM, 1 nM, 900 pM, 800 pM, 700 pM, 600 pM, 500 pM, 400 pM, 300 pM, 200 pM, 100 pM, 50 pM, 1 pM.

The term "immunoglobulin (Ig)" as used herein refers to immunity conferring glycoproteins of the immunoglobulin superfamily. "Surface immunoglobulins" are attached to the membrane of e.g. effector cells or endothelial cells by their transmembrane region and encompass molecules such as but not limited to neonatal Fc-receptor, B-cell receptors, T-cell receptors, class I and II major histocompatibility complex (MHC) proteins, beta-2 microglobulin (β2M), CD3, CD4 and CD8.

Typically, the term "antibody" as used herein refers to secreted immunoglobulins which lack the transmembrane region and can thus, be released into the bloodstream and body cavities. Human antibodies are grouped into different isotypes based on the heavy chain they possess. There are five types of human Ig heavy chains denoted by the Greek letters: α, γ, δ, ε, and μ. The type of heavy chain present defines the class of antibody, i.e. these chains are found in IgA, IgD, IgE, IgG, and IgM antibodies, respectively, each performing different roles, and directing the appropriate immune response against different types of antigens. Distinct heavy chains differ in size and composition; and may comprise approximately 450 amino acids (Janeway et al. (2001) Immunobiology, Garland Science). IgA is found in mucosal areas, such as the gut, respiratory tract and urogenital tract, as well as in saliva, tears, and breast milk and prevents colonization by pathogens (Underdown & Schiff (1986) Annu. Rev. Immunol. 4:389-417). IgD mainly functions as an antigen receptor on B cells that have not been exposed to antigens and is involved in activating basophils and mast cells to produce antimicrobial factors (Geisberger et al. (2006) Immunology 118:429-437; Chen et al. (2009) Nat. Immunol. 10:889-898). IgE is involved in allergic reactions via its binding to allergens triggering the release of histamine from mast cells and basophils. IgE is also involved in protecting against parasitic worms (Pier et al. (2004) Immunology, Infection, and Immunity, ASM Press). IgG provides the majority of antibody-based immunity against invading pathogens and is the only antibody isotype capable of crossing the placenta to give passive immunity to fetus (Pier et al. (2004) Immunology, Infection, and Immunity, ASM Press). In humans there are four different IgG subclasses (IgG1, 2, 3, and 4), named in order of their abundance in serum with IgG1 being the most abundant (~66%), followed by IgG2 (~23%), IgG3 (~7%) and IgG (~4%). The biological profile of the different IgG classes is determined by the structure of the respective hinge region. IgM is expressed on the surface of B cells in a monomeric form and in a secreted pentameric form with very high avidity. IgM is involved in eliminating pathogens in the early stages of B cell mediated (humoral) immunity before sufficient IgG is produced (Geisberger et al. (2006) Immunology 118:429-437). Antibodies are not only found as monomers but are also known to form dimers of two Ig units (e.g. IgA), tetramers of four Ig units (e.g. IgM of teleost fish), or pentamers of five Ig units (e.g. mammalian IgM). Antibodies are typically made of four polypeptide chains comprising two identical heavy chains and two identical light chains which are connected via disulfide bonds and resemble a "Y"-shaped macro-molecule. Each of the chains comprises a number of immunoglobulin domains out of which some are constant domains and others are variable domains. Immunoglobulin domains consist of a 2-layer sandwich of between 7 and 9 antiparallel n-strands arranged in two β-sheets. Typically, the heavy chain of an antibody comprises four Ig domains with three of them being constant (CH domains: CH1, CH2, CH3) domains and one of them being a variable domain (VH). The light chain typically comprises one constant Ig domain (CL) and one variable Ig domain (V L). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "Ig-like constant region consensus (IgLCRC)" describes the numbering derived from an alignment of human immunoglobulin or human immunoglobulin-like proteins as indicated in FIG. 4. The skilled person knows how to add further human immunoglobulin or human immunoglobulin-like proteins to this alignment using sequence identity and/or structural information. Thus, the skilled person can determine for each amino acid of a given human immunoglobulin or human immunoglobulin-like protein its respective IgLCRC number. For example, the six intervening regions "b", "c", "d", "e", "f" and "g" of CH3 of IgG1 span IgLCRC 19 to 30 (without comprising the amino acid at IgLCRC position 26 and 28), IgLCRC 41 to 45 (without comprising the amino acid at IgLCRC position 43), IgLCRC 53 to 62 (without comprising amino acids at IgLCRC positions 59 to 61), e spans IgLCRC positions 71 to 80 (without comprising the amino acid at IgLCRC position 72 to 76), IgLCRC 90 to 101 (without comprising amino acids at IgLCRC 98 and 99), and IgLCRC 109 to 127 (without comprising amino acids at IgLCRC positions 112 to 124). CH3 of IgG1 lacks amino acids at some IgLCRC positions. This is due to the higher variability in these less structured regions of human immunoglobulin or human immunoglobulin-like proteins, which are amenable to amino acid deletions and insertions without altering the overall structure of the human immunoglobulin or human immunoglobulin-like protein. Similarly, the seven beta strands "A", "B", "C", "D", "E", "F", and "G" of CH3 of IgG1 span IgLCRC positions 13 to 18, 31 to 40, 46 to 52, 63 to 70, 81 to 89, 102 to 108, and 128 to 133. Furthermore, the N-terminal region "a" of CH3 of IgG1 spans IgLCRC 7 to 12 and the C-terminal region "h" spans IgLCRC 134 to 139. In an analogous manner the skilled person can also determine for each given human immunoglobulin or human immunoglobulin-like protein the N-terminal and C-terminal end, respectively, of each element within a given human immunoglobulin or human immunoglobulin-like protein. The number of gaps in the amino acid sequence of a given aligned human immunoglobulin or human immunoglobulin-like protein may vary. However, beta strand A spans IgLCRC positions 13 to 18, beta strand B spans IgLCRC positions 31 to 40, beta strand C spans IgLCRC positions 46 to 52, beta strand D spans IgLCRC positions 63 to 70, beta strand E spans IgLCRC positions 81 to 89, beta strand F spans IgLCRC positions 102 to 108, beta strand G spans IgLCRC positions 128 to 133, and the intervening region b spans IgLCRC positions 19 to 30, the intervening region c spans IgLCRC positions 41 to 45, the intervening region d spans IgLCRC positions 53 to 62, the intervening region e spans IgLCRC positions 71 to 80, the intervening region f spans IgLCRC positions 90 to 101 and the intervening region g spans IgLCRC positions 109 to 127 of CH3. The N-terminal region a spans IgLCRC positions 1 to 12 and the C-terminal region h IgLCRC positions 134 up to the C-terminus of the respective human immunoglobulin or human immunoglobulin-like protein.

In case of amino acid sequences not included in FIG. 4 which may comprise one or more intervening regions of a length that exceed the herein defined intervening regions b (22 residues), c (5 residues), d (10 residues), e (12 residues), f (19 residues), or that comprise a N-terminal region of a length that exceeds the herein defined N-terminal region a (12 residues), additional residues can be introduced into the IgLCRC numbering scheme subsequent to position 6 by designating additional residues 6a, 6b, 6c etc, or subsequent to position 25 by designating additional residues 25a, 25b, 25c etc, or subsequent to position 42 by designating additional residues 42a, 42b, 42c etc, or subsequent to position 58 by designating additional residues 58a, 58b, 58c etc, or subsequent to position 71 by designating additional residues 71a, 71b, 71c etc, or subsequent to position 91 by designating additional residues 91a, 91b, 91c etc, or subsequent to position 111 by designating additional residues 111a, 111b, 111c etc. Moreover, since the respective amino acid sequence of a given human immunoglobulin or human immunoglobulin-like protein does not necessarily start at IgLCRC position 1 and may also have gaps when aligned as indicated in FIG. 4 the IgLCRC position does not directly reflect the amino acid position within the sequences included in the sequence listing. For example, a preferred CH3 of IgG1 has the amino acid sequence according to SEQ ID NO: 45. The N-terminal region spans IgLCRC positions 7 to 12, which correspond to amino acids 1 to 6 of SEQ ID NO: 45, beta strands "A", "B", "C", "D", "E", "F", and "G" of CH3 of IgG1 span IgLCRC positions 13 to 18, 31 to 40, 46 to 52, 63 to 70, 81 to 89, 102 to 108, and 128 to 133, which corresponds respectively to amino acids 7 to 12, 23 to 32, 37 to 43, 51 to 58, 64 to 72, 83 to 88, 95 to 100 of SEQ ID NO: 45. The C-terminal region spans amino acids 101 to 107. The five intervening regions "b", "c", "d", "e", "f" and "g" of CH3 of IgG1 span 1 IgLCRC positions 19 to 30, 41 to 45, 53 to 62, 71 to80, 90 to 101, and 109 to 127, which corresponds respectively to amino acids 13 to 22, 33 to 36, 44 to 50, 53 to 63, 59 to 63, 73 to 82 and 89 to 94 of SEQ ID NO: 45. Given these considerations the skilled person can determine each element of the $1^{st}$, $2^{nd}$, $3^{rd}$ and $4^{th}$ CRI without undue burden. Once the elements are determined and the sequences of the $1^{st}$ and $2^{nd}$ CRI on one hand and the $3^{rd}$ and $4^{th}$ CRI on the other hand are aligned, it is also straightforward for the skilled person to follow the instructions given below and to replace amino acids of the $1^{st}$ and $3^{rd}$ CRI with amino acids of the $3^{rd}$ and $4^{th}$ CRI, respectively.

The term "antigen-binding protein", as used herein, refers to immunoglobulin molecules and immunologically active portions of immunoglobulin molecules, i.e. molecules that contain an antigen-binding site that immunospecifically binds an antigen. Also comprised are immunoglobulin-like proteins that are selected through techniques including, for example, phage display to specifically bind to a target molecule or target epitope. In assessing the binding and/or specificity of an antigen binding protein, e.g., an antibody or immunologically functional fragment thereof, an antibody or fragment can substantially inhibit binding of a ligand to its binding partner when an excess of antibody reduces the quantity of binding partner bound to the ligand by at least about 1-20%, 20-30%, 30-40%, 40-50%, 50-60%, 60-70%, 70-80%, 80-85%, 85-90%, 90-95%, 95-97%, 97-98%, 98-99% or more (e.g. as measured in an in vitro competitive binding assay). The neutralizing ability may be described in terms of an $IC_{50}$ or $EC_{50}$ value.

The "$IC_{50}$" value refers to the half maximal inhibitory concentration and is thus a measure of the effectiveness of a substance in inhibiting a specific biological or biochemical function. The values are typically expressed as molar concentration. The $IC_{50}$ of a drug can be determined in functional antagonistic assays by constructing a dose-response curve and examining the inhibitory effect of the examined substance at different concentrations. Alternatively, competition binding assays may be performed in order to determine the $IC_{50}$ value. Typically, inhibitory antibodies of the present invention exhibit an $IC_{50}$ value of between 50 nM-1 pM, i.e. 50 nM, 10 nM, 1 nM, 900 pM, 800 pM, 700 pM, 600 pM, 500 pM, 400 pM, 300 pM, 200 pM, 100 pM, 50 pM, 1 pM.

The "$EC_{50}$" value refers to half maximal effective concentration of a substance and is thus a measure of the concentration of said substance which induces a response halfway between the baseline and maximum after a specified exposure time. It is commonly used as a measure of drug's potency. The $EC_{50}$ of a graded dose response curve therefore represents the concentration of a substance where 50% of its maximal effect is observed. The $EC_{50}$ of a quantal dose response curve represents the concentration of a compound where 50% of the population exhibit a response, after a specified exposure duration. Typically, inhibitory antibodies of the present invention exhibit an $EC_{50}$ value of between 50 nM to 1 pM, i.e. 50 nM, 10 nM, 1 nM, 900 pM, 800 pM, 700 pM, 600 pM, 500 pM, 400 pM, 300 pM, 200 pM, 100 pM, 50 pM, or 1 pM.

The term "antigen-binding fragment" of an antibody (or simply "binding portion"), as used herein, refers to one or more fragments of an antibody that retain the ability to specifically bind to an antigen. It has been shown that the antigen-binding function of an antibody can be performed by fragments of a full-length antibody.

As used herein, "human antibodies" include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). Human antibodies of the invention include antibodies isolated from human immunoglobulin libraries or from animals transgenic for one or more human immunoglobulin and that do not express endogenous immunoglobulins, as described for example in U.S. Pat. No. 5,939,598 by Kucherlapati & Jakobovits.

The term "monoclonal antibody" as used herein refers to a preparation of antibody molecules of single molecular composition. A monoclonal antibody displays a single binding specificity and affinity for a particular epitope. In one embodiment, the monoclonal antibodies are produced by a hybridoma which includes a B cell obtained from a non-human animal, e.g. mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g. from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human is less likely to elicit an immune response from a human subject when the antibodies are injected than would the constant region from a non-human source. However, the definition is not limited to this particular example.

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen-binding sites may be wild-type or modified by one or more amino acid substitutions, e.g. modified to resemble human imunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

Different methods for humanizing antibodies are known to the skilled person, as reviewed by Almagro & Fransson, 2008, the content of which is herein incorporated by reference in its entirety. The review article by Almagro & Fransson is briefly summarized in the following. Almagro & Fransson distinguish between rational approaches and empirical approaches. Rational approaches are characterized by generating few variants of the engineered antibody and assessing their binding or any other property of interest. If the designed variants do not produce the expected results, a new cycle of design and binding assessment is initiated. Rational approaches include CDR grafting, Resurfacing, Superhumanization, and Human String Content Optimization. In contrast, empirical approaches are based on the generation of large libraries of humanized variants and selection of the best clones using enrichment technologies or high-throughput screening. Accordingly, empirical approaches are dependent on a reliable selection and/or screening system that is able to search through a vast space of antibody variants. In vitro display technologies, such as phage display and ribosome display fulfill these requirements and are well-known to the skilled person. Empirical approaches include FR libraries, Guided selection, Framework-shuffling, and Humaneering.

A "bivalent antibody" comprises two antigen binding sites. Bivalent antibodies may be monospecific or bispecific. In case, the bivalent antibody is monospecific, the two binding sites of the antibody have the same antigen specificities. A "bispecific" or "bifunctional" antigen binding protein or antibody is a hybrid antigen binding protein or antibody, respectively, having two different antigen binding sites. The two binding sites of a bispecific antigen binding protein or antibody bind to two different epitopes residing either on the same or on different antigens. Bispecific antigen binding proteins and antibodies are a species of multispecific antigen binding protein antibody and can be produced by a variety of methods including, but not limited to, fusion of hybridomas, chemical linking of IgG or IgG fragments such as Fab', or by genetic means. See, e.g., Songsivilai and Lachmann, 1990, Clin. Exp. Immunol. 79:315-321; Kostelny et al., 1992, J. Immunol. 148:1547-1553; Kontermann, 2014, MAbs 4:182-197.

A "trifunctional antibody" is a type of bispecific antibody which comprises the two binding sites targeting different antigens as well as an intact Fc-part which can bind to an Fc receptor on accessory cells (e.g. monocytes/macrophages, natural killer cells, dendritic cells or other). For example, a trifunctional antibody may comprise a binding site targeting an epitope on the surface of a cancer cell, the second binding site may target an epitope on the surface of a T cell (e.g. CD3) and the Fc-part may bind to the Fc receptor on the surface of a macrophage. Such trifunctional antibody is thus able to link T cells and macrophages to the tumor cells, leading to their destruction.

Papain digestion of antibodies produces two identical antigen binding fragments, called "Fab fragments" (also referred to as "Fab portion" or "Fab region") each with a single antigen binding site, and a "Fe fragment" (also referred to as "Fc portion" or "Fc region") whose name reflects its ability to crystallize readily. The crystal structure of the human IgG Fc region has been determined (Deisenhofer (1981) Biochemistry 20:2361-2370). In IgG, IgA and IgD isotypes, the Fc region is composed of two identical protein fragments, derived from the CH2 and CH3 domains of the antibody's two heavy chains; in IgM and IgE isotypes, the Fc regions contain three heavy chain constant domains (CH2-4) in each polypeptide chain. In addition, smaller immunoglobulin molecules exist naturally or have been constructed artificially. The term "Fab' fragment" refers to a Fab fragment additionally comprise the hinge region of an Ig molecule whilst "F(ab')2 fragments" are understood to comprise two Fab' fragments being either chemically linked or connected via a disulfide bond. Whilst "single domain antibodies (sdAb)" (Desmyter et al. (1996) Nat. Structure Biol. 3:803-811) and "Nanobodies" only comprise a single VH domain, "single chain Fv (scFv)" fragments comprise the heavy chain variable domain joined via a short linker peptide to the light chain variable domain (Huston et al. (1988) Proc. Natl. Acad. Sci. USA 85, 5879-5883). Divalent single-chain variable fragments (di-scFvs) can be engineered by linking two scFvs (scFvA-scFvB). This can be done by producing a single peptide chain with two VH and two VL regions, yielding "tandem scFvs" (VHA-VLA-VHB-VLB). Another possibility is the creation of scFvs with linkers that are too short for the two variable regions to fold together, forcing scFvs to dimerize. Usually linkers with a length of 5 residues are used to generate these dimers. This type is known as "diabodies". Still shorter linkers (one or two amino acids) between a V H and V L domain lead to the formation of monospecific trimers, so-called "triabodies" or "tribodies". Bispecific diabodies are formed by expressing to chains with the arrangement VHA-VLB and VHB-VLA or VLA-VHB and VLB-VHA, respectively. Single-chain diabodies (scDb) comprise a VHA-VLB and a VHB-VLA fragment which are linked by a linker peptide (P) of 12-20 amino acids, preferably 14 amino acids, (VHA-VLB-P-VHB-VLA). "Bi-specific T-cell engagers (BiTEs)" are fusion proteins consisting of two scFvs of different antibodies wherein one of the scFvs binds to T cells via the CD3 receptor, and the other to a tumor cell via a tumor specific molecule (Kufer et al. (2004) Trends Biotechnol. 22:238-244). Dual affinity retargeting molecules ("DART" molecules) are diabodies additionally stabilized through a C-terminal disulfide bridge.

As used herein, the term "antibody-like protein" or immunoglobulin-like protein refers to a protein that has been engineered (e.g. by mutagenesis of loops) to specifically bind to a target molecule. Typically, such an antibody-like protein comprises at least one variable peptide loop attached at both ends to a protein scaffold. This double structural constraint greatly increases the binding affinity of the antibody-like protein to levels comparable to that of an antibody. The length of the variable peptide loop typically consists of 10 to 20 amino acids. The scaffold protein may be any protein having good solubility properties. Preferably, the scaffold protein is a small globular protein. Antibody-like proteins include without limitation affibodies, anticalins, and designed ankyrin repeat proteins (for review see: Binz H. K. et al. (2005) Engineering novel binding proteins from non-immunoglobulin domains. Nat. Biotechnol. 23(10):1257-1268). Antibody-like proteins can be derived from large libraries of mutants, e.g. be panned from large phage display libraries and can be isolated in analogy to regular antibodies. Also, antibody-like binding proteins can be obtained by combinatorial mutagenesis of surface-exposed residues in globular proteins. Antibody-like proteins are sometimes referred to as "peptide aptamers".

As used herein, a "peptidomimetic" is a small protein-like chain designed to mimic a peptide. Peptidomimetics typically arise from modification of an existing peptide in order to alter the molecule's properties. For example, they may arise from modifications to change the molecule's stability or biological activity. This can have a role in the development of drug-like compounds from existing peptides. These modifications involve changes to the peptide that will not occur naturally (such as altered backbones and the incorporation of nonnatural amino acids).

The term "target" refers to a molecule or a portion of a molecule capable of being bound by an antigen binding protein. In certain embodiments, a target can have one or more epitopes. In certain embodiments, a target is an antigen. The use of "antigen" in the phrase "antigen binding protein" simply denotes that the protein sequence that comprises the antigen can be bound by an antibody. In this context, it does not require that the protein be foreign or that it be capable of inducing an immune response.

The term "recombinant" refers to an amino acid sequence or a nucleotide sequence that is intentionally modified by recombinant methods. The term "recombinant nucleic acid" as used herein refers to a nucleic acid which is formed in vitro, and optionally further manipulated by endonucleases to form a nucleic acid molecule not normally found in nature. Exemplified, recombinant nucleic acids include cDNA, in a linear form, as well as vectors formed in vitro by ligating DNA molecules that are not normally joined. It is understood that once a recombinant nucleic acid is made and introduced into a host cell, it will replicate non-recombinantly, i.e. using the in vivo cellular machinery of the host cell rather than in vitro manipulations. Accordingly, nucleic acids which were produced recombinantly, may be replicated subsequently non-recombinantly. A "recombinant protein" is a protein made using recombinant techniques, e.g. through the expression of a recombinant nucleic acid as depicted above. The term "recombinant vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

The term "host cell" refers to a cell that harbours a vector (e.g. a plasmid or virus). Such host cell may either be a prokaryotic (e.g. a bacterial cell) or a eukaryotic cell (e.g. a fungal, plant or animal cell). Host cells include both single-cellular prokaryote and eukaryote organisms (e.g., bacteria, yeast, and actinomycetes) as well as single cells from higher order plants or animals when being grown in cell culture. "Recombinant host cell", as used herein, refers to a host cell that comprises a polynucleotide that codes for a polypeptide fragment of interest, i.e., the fragment of the viral PA subunit or variants thereof according to the invention. This polynucleotide may be found inside the host cell (i) freely dispersed as such, (ii) incorporated in a recombinant vector, or (iii) integrated into the host cell genome or mitochondrial DNA. The recombinant cell can be used for expression of a polynucleotide of interest or for amplification of the polynucleotide or the recombinant vector of the invention. The term "recombinant host cell" includes the progeny of the original cell which has been transformed, transfected, or infected with the polynucleotide or the recombinant vector of the invention. A recombinant host cell may be a bacterial cell such as an *E. coli* cell, a yeast cell such as *Saccharomyces cerevisiae* or *Pichia pastoris*, a plant cell, an insect cell such as SF9 or High Five cells, or a mammalian cell. Preferred examples of mammalian cells are Chinese hamster ovary (CHO) cells, green African monkey kidney (COS) cells, human embryonic kidney (HEK293) cells, HELA cells, and the like.

The terms "individual", "subject", or "patient" are used interchangeably herein and refer to any mammal, reptile or bird that may benefit from the present invention. In particular, an individual is selected from the group consisting of laboratory animals (e.g. mouse, rat or rabbit), domestic animals (including e.g. guinea pig, rabbit, horse, donkey, cow, sheep, goat, pig, chicken, duck, camel, cat, dog, turtle, tortoise, snake, or lizard), or primates including chimpanzees, bonobos, gorillas and human beings. In particular, the "individual" is a human being.

The term "disease" and "disorder" are used interchangeably herein, referring to an abnormal condition, especially an abnormal medical condition such as an illness or injury, wherein a tissue, an organ or an individual is not able to efficiently fulfil its function anymore. Typically, but not necessarily, a disease is associated with specific symptoms or signs indicating the presence of such disease. The presence of such symptoms or signs may thus, be indicative for a tissue, an organ or an individual suffering from a disease. An alteration of these symptoms or signs may be indicative for the progression of such a disease. A progression of a disease is typically characterised by an increase or decrease of such symptoms or signs which may indicate a "worsening" or "bettering" of the disease. The "worsening" of a disease is characterised by a decreasing ability of a tissue, organ or organism to fulfil its function efficiently, whereas the "bettering" of a disease is typically characterised by an increase in the ability of a tissue, an organ or an individual to fulfil its function efficiently. A tissue, an organ or an individual being at "risk of developing" a disease is in a healthy state but shows potential of a disease emerging. Typically, the risk of developing a disease is associated with early or weak signs or symptoms of such disease. In such case, the onset of the disease may still be prevented by treatment. Examples of a disease include but are not limited to infectious diseases, traumatic diseases, inflammatory diseases, cutaneous conditions, endocrine diseases, intestinal diseases, neurological disorders, joint diseases, genetic disorders, autoimmune diseases, and various types of cancer.

By "tumor" is meant an abnormal group of cells or tissue that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign or malignant.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

"Symptoms" of a disease or disorder are implication of the disease or disorder noticeable by the tissue, organ or organism having such disease or disorder and include but are not limited to pain, weakness, tenderness, strain, stiffness, and spasm of the tissue, an organ or an individual as well as the presence, absence, increase, decrease, of specific indicators such as biomarkers or molecular markers. The term "disease" and "disorder" as used herein, refer to an abnormal condition, especially an abnormal medical condition such as an illness or injury, wherein a tissue, an organ or an individual is not able to efficiently fulfil its function anymore. Typically, but not necessarily, a disease or disorder is associated with specific symptoms or signs indicating the presence of such disease or disorder. Diseases or disorders include but are not limited to autoimmune diseases, allergic diseases, cancer type diseases, cutaneous conditions, endocrine diseases, blood diseases and disorders, eye diseases and disorders, genetic disorders, inflammatory diseases, infectious diseases, intestinal diseases, neurological disorders, and mental illness. Exemplified, cancer type diseases include but are not limited to Basal cell carcinoma, Bladder cancer, Bone cancer, Brain tumor, Breast cancer, Burkitt lymphoma, Cervical cancer, Colon Cancer, Cutaneous T-cell lymphoma, Esophageal cancer, Retinoblastoma, Gastric (Stomach) cancer, Gastrointestinal stromal tumor, Glioma, Hodgkin lymphoma, Kaposi sarcoma, Leukemias, Lymphomas, Melanoma, Oropharyngeal cancer, Ovarian cancer, Pancreatic cancer, Pleuropulmonary blastoma, Prostate cancer, Throat cancer, Thyroid cancer, and Urethral cancer.

As used herein, "treat", "treating", "treatment" or "therapy" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in an individual that has previously had the disorder(s); and (e) limiting or preventing recurrence of symptoms in individuals that were previously symptomatic for the disorder(s). Accordingly, a moiety having a therapeutic effect treats the symptoms of a disease or disorder by accomplishing one or more of above named effects (a)-(e).

As used herein, "prevent", "preventing", "prevention", or "prophylaxis" of a disease or disorder means preventing that such disease or disorder occurs in patient.

The terms "IgG1, IgG2, IgG3, IgG4, IgA1, IgA2, IgD, IgE, IgM Igκ, Igλ, TCR," as used herein, describe antibodies or molecules containing domains of the Ig-superfamily and can be of human, murine, rat, other rodent, bovine and other origin, in particular human origin.

The terms "HLA" as used herein, describes a human leucocyte antigen, which is also named MHC (major histocompatibility complex), includes MHC class 1 and II type molecules, containing domains of the Ig-superfamily and can be of human, murine, rat, other rodent, bovine and other origin.

The term "ASL" as used herein, describes an antigen-specific ligand. Accordingly, a ASLAn1 refers to an antigen-specific ligand which is specific to antigen 1, a ASLAn2 is specific to antigen 2, a ASLAn3 is specific to antigen 3, and so on The terms "pharmaceutical", "medicament" and "drug" are used interchangeably herein, referring to a substance and/or a combination of substances being used for the identification, prevention or treatment of a disease or disorder.

"Atrosab" is a humanized monoclonal antibody that specifically blocks the pro-inflammatory TNF receptor 1 (TNFR1), without interacting with the TNF receptor 2 (TNFR2). Atrosab is currently under development for further clinical studies.

EMBODIMENTS

In a first aspect the present invention provides a protein complex comprising at least two amino acid chains I and II, which are non-covalently bound to each other through a heterodimerization region I (HRI) comprised in amino acid chain I and a heterodimerization region II (HRII) comprised in amino acid chain II, wherein (a) HRI comprises seven antiparallel beta strands AI, BI, CI, DI, EI, FI, and GI, six intervening regions bI, cI, dI, eI, fI, and gI, a N-terminal region aI and a C-terminal region hI positioned from N- to C-terminus in the following order aI-AI-bI-BI-cI-CI-dI-DI-eI-EI-fI-FI-gI-GI-hI, wherein the HRI is a fusion protein of a first human constant region of an immunoglobulin or immunoglobulin-like protein (1$^{st}$ CRI, acceptor) interspersed with amino acids of a second human constant region of an immunoglobulin or immunoglobulin-like protein (2$^{nd}$ CRI, donor), wherein the 1$^{st}$ CRI comprises seven antiparallel beta strands A1, B1, C1, D1, E1, F1, and G1, six intervening regions b1, c1, d1, e1, f1, and g1, a N-terminal region a1 and a C-terminal region h1 arranged from N- to C-terminus in the following order a1-A1-b1-B1-c1-C1-d1-D1-e1-E1-f1-F1-g1-G1-h1, wherein the $2^{nd}$ CRI comprises seven antiparallel beta strands A2, B2, C2, D2, E2, F2, and G2, six intervening regions b2, c2, d2, e2, f2, and g2, aN-terminal region a2 and a C-terminal region h2 positioned from N- to C-terminus in the following order a2-A2-b2-B2-c2-C2-d2-D2-e2-E2-f2-F2-g2-G2-h2, wherein HRI has the amino acid sequence of the $1^{st}$ CRI and wherein at least the following amino acids of the $1^{st}$ CRI are replaced with the following amino acids of the $2^{nd}$ CRI:
(i) at least 1 amino acid of a1 is replaced with at least 1 amino acid of a2 (Replacement 1), in a preferred embodiment at least 4 to 12 amino acids, i.e. 4, 5, 6, 7, 8, 9, 10, 11, or 12, more preferably 6 to 8 amino acids of a1 are replaced with at least 4 to 12 amino acids, i.e. 4, 5, 6, 7, 8, 9, 10, 11, or 12, more preferably 6 to 8 amino acids of a2; and (ii) at least 1 amino acid of c1 is replaced with at least 1 amino acid of c2 (Replacement 2), in a preferred embodiment a continuous amino acid stretch consisting of 1 to 5 amino acid of c1, i.e. 1, 2, 3, 4, or 5, and 1 to 6 amino acids of C1, i.e. 1, 2, 3, 4, 5, or 6, more preferably a continuous amino acid stretch comprising or consisting of 2 to 5 amino acids of c1 and 4 to 6 amino acids of C1, is replaced with a continuous amino acid stretch consisting of 1 to 5 amino acid of c2, i.e. 1, 2, 3, 4, or 5, and 1 to 6 amino acids of C2, i.e. 1, 2, 3, 4, 5, or 6, more preferably with a continuous amino acid stretch comprising or consisting of 2 to 5 amino acids of c2 and 4 to 6 amino acids of C2, more preferably 1 to 5 amino acids of c1 are replaced with 1 to 5 amino acids of c2, preferably the residue replaced in Replacement 2 comprise IgLCRC positions 47 and 49, preferably the total length of the replaced continuous amino acid stretch is between 5 to 11, more preferably 5 to 9 and even more preferably 5 to 7 amino acids; and (iii) at least 1 amino acid of g1 is replaced with at least 1 amino acid of g2 (Replacement 3), in a preferred embodiment a continuous amino acid stretch comprising or consisting of 1 to 10 amino acids of g1, i.e. 1, 2, 3, 4, 5, 6, 7, 8, 9, or 10, preferably 1 to 6 amino acids of F1, i.e. 1, 2, 3, 4, 5, or 6, 1 to 10 amino acids of g1, i.e. 1, 2, 3, 4, 5, 6, 7, 8, 9, or 10, and 0 to 3 amino acids of G1, i.e. 0, 1, 2, or 3, is replaced with a continuous amino acid stretch comprising or consisting of at 1 to 10 amino acids of g2, i.e. 1, 2, 3, 4, 5, 6, 7, 8, 9 or 10, preferably 1 to 6 amino acids of F2 i.e. 1, 2, 3, 4, 5, or 6, 1 to 10 amino acids of g1, i.e. 1, 2, 3, 4, 5, 6, 7, 8, 9, or 10, and 0 to 3 amino acids of G2 i.e. 0, 1, 2, or 3, it is preferred that the total length of the replaced continuous amino acid stretch is between 3 to 20 more preferably 3 to 18, even more preferably 3 to 15; and wherein (b) HRII comprises seven antiparallel beta strands AII, BII, CII, DII, EII, FII, and GII, six intervening regions bII, cII, dII, eII, fII, and gII, a N-terminal region all and a C-terminal region hII positioned from N- to C-terminus in the following order aII-AII-bII-BII-cII-CII-dII-DII-eII-EII-fII-FII-gII-GII-hII, wherein the HRII is a fusion protein of a third human constant region of an immunoglobulin or immunoglobulin-like protein ($3^{rd}$ CRI, acceptor) interspersed with amino acids of a fourth human constant region of an immunoglobulin or immunoglobulin-like protein ($4^{th}$ CRI, donor), and wherein the $3^{rd}$ CRI comprises seven antiparallel beta strands A3, B3, C3, D3, E3, F3, and G3, six intervening regions b3, c3, d3, e3, f3, and g3, a N-terminal region a3 and a C-terminal region h3 positioned from N- to C-terminus in the following order a3-A3-b3-B3-c3-C3-d3-D3-e3-E3-f3-F3-g3-G3-h3, wherein the $4^{th}$ CRI comprises seven antiparallel beta strands A4, B4, C4, D4, E4, F4, and G4, six intervening regions b4, c4, d4, e4, f4, and g4, a N-terminal region a4 and a C-terminal region h4 positioned from N- to C-terminus in the following order a4-A4-b4-B4-c4-C4-d4-D4-e4-E4-f4-F4-g4-G4-h4, wherein HRII has the amino acid sequence of the $3^{st}$ CRI and wherein at least the following amino acids amino acids of the $3^{rd}$ CRI are replaced with the following amino acids of the 4th CRI:

(i) at least 1 amino acid of a3 is replaced with at least 1 amino acid of a4 (Replacement 4), in a preferred embodiment at least 4 to 12 amino acids, i.e. 4, 5, 6, 7, 8, 9, 10, 11, or 12, more preferably 6 to 10 amino acids of a3 are replaced with at least 4 to 12 amino acids, i.e. 4, 5, 6, 7, 8, 9, 10, 11, or 12, more preferably 6 to 10 amino acids of a4; and (ii) at least 1 amino acid of c3 is replaced with at least 1 amino acid of c4 (Replacement 5), in a preferred embodiment a continuous amino acid stretch consisting of 1 to 5 amino acid of c3, i.e. 1, 2, 3, 4, or 5, and 1 to 6 amino acids of C3, i.e. 1, 2, 3, 4, 5, or 6, more preferably a continuous amino acid stretch consisting of 2 to 5 amino acids of c3 and 4 to 6 amino acids of C3, is replaced with a continuous amino acid stretch consisting of 1 to 5 amino acid of c4, i.e. 1, 2, 3, 4, or 5, and 1 to 6 amino acids of C4, i.e. 1, 2, 3, 4, 5, or 6, more preferably with a continuous amino acid stretch consisting of 2 to 5 amino acids of c4 and 4 to 6 amino acids of C4;

more preferably 1 to 5 amino acids of c3 are replaced with 1 to 5 amino acids of c4, preferably the residue replaced in Replacement 5 comprise IgLCRC positions 47 and 49, preferably the total length of the replaced continuous amino acid stretch is between 5 to 11, more preferably 5 to 9 and even more preferably 5 to 7; and (iii) at least 1 amino acid of g3 is replaced with at least 1 amino acid of g4 (Replacement 6), in a preferred embodiment a continuous amino acid stretch comprising or consisting of 1 to 10 amino acids of g1, i.e. 1, 2, 3, 4, 5 6, 7, 8, 9 or 10, preferably 1 to 6 amino acids of F3, i.e. 1, 2, 3, 4, 5 or 6, 1 to 10 amino acids of g1, i.e. 1, 2, 3, 4, 5 6, 7, 8, 9 or 10, and 0 to 3 amino acids of G3, i.e. 0, 1, 2 or 3, is replaced with a continuous amino acid stretch comprising or consisting of 1 to 10 amino acids ofF4, i.e. 1, 2, 3, 4, 5, 6, 7, 8, 9, or 10, preferably 1 to 6 amino acids of F4, i.e. 1, 2, 3, 4, 5 or 6, and 0 to 3 amino acids of G4, i.e. 0, 1, 2, or 3, preferably the total length of the replaced continuous amino acid stretch is between 3 to 20 amino acids, more preferably 3 to 18 amino acids, and even more preferably 3 to 15;

wherein the 1ˢᵗ CRI and the 3ʳᵈ CRI are different from each other and specifically bind to each other under physiological conditions.

Thus, HRI preferably has the following amino acid structure:
(i) at least 1 amino acid of a1 spanning IgLCRC positions 1 to 12 of the immunoglobulin or immunoglobulin-like protein is replaced with at least 1 amino acid of a2 spanning IgLCRC positions 1 to 12 of the immunoglobulin or immunoglobulin-like protein, in a preferred embodiment at least 4 to 12 amino acids, i.e. 4, 5, 6, 7, 8, 9, 10, 11, or 12, more preferably 6 to 8 amino acids of a1 spanning IgLCRC positions 1 to 12 are replaced with at least 4 to 12 amino acids, i.e. 4, 5, 6, 7, 8, 9, 10, 11, or 12, more preferably 6 to 8 amino acids of a2 spanning IgLCRC positions 1 to 12; and
(ii) at least 1 amino acid of c1 spanning IgLCRC positions 41 to 45 of the immunoglobulin or immunoglobulin-like protein is replaced with at least 1 amino acid of c2 spanning IgLCRC positions 41 to 45 of the immunoglobulin or immunoglobulin-like protein, in a preferred embodiment a continuous amino acid stretch consisting of 1 to 5 amino acid of c1 spanning IgLCRC positions 41 to 45 of the immunoglobulin or immunoglobulin-like protein, i.e. 1, 2, 3, 4, or 5 amino acids, and 1 to 6 amino acids of C1 spanning IgLCRC positions 46 to 52, i.e. 1, 2, 3, 4, 5, or 6 amino acids, more preferably a continuous amino acid stretch comprising or consisting of 2 to 5 amino acids of c1 spanning IgLCRC positions 41 to 45 and 4 to 6 amino acids of C1 spanning IgLCRC positions 46 to 52, is replaced with a continuous amino acid stretch consisting of 1 to 5 amino acid of c2 spanning IgLCRC positions 41 to 45 of the immunoglobulin or immunoglobulin-like protein, i.e. 1, 2, 3, 4, or 5, and 1 to 6 amino acids of C2 spanning IgLCRC positions 46 to 52, i.e. 1, 2, 3, 4, 5, or 6 amino acid, more preferably with a continuous amino acid stretch comprising or consisting of 2 to 5 amino acids of c2 spanning IgLCRC positions 41 to 45 and 4 to 6 amino acids of C2 spanning IgLCRC positions 46 to 52, more preferably 1 to 5 amino acids of c1 are replaced with 1 to 5 amino acids of c2, preferably the residue replaced in Replacement 2 comprise IgLCRC positions 47 and 49,
preferably the total length of the replaced continuous amino acid stretch is between 5 to 11, more preferably 5 to 9 and even more preferably 5 to 7 amino acids; and
(iii) at least 1 amino acid of g1 spanning IgLCRC positions 109 to 127 of the immunoglobulin or immunoglobulin-like protein is replaced with at least 1 amino acid of g2 spanning IgLCRC positions 109 tp 127 of the immunoglobulin or immunoglobulin-like protein, in a preferred embodiment a continuous amino acid stretch comprising or consisting of 1 to 10 amino acids of g1 spanning IgLCRC positions 109 to 127 of the immunoglobulin or immunoglobulin-like protein, i.e. 1, 2, 3, 4, 5, 6, 7, 8, 9, or 10 amino acids, preferably 1 to 6 amino acids of F1 spanning IgLCRC positions 102 to 108, i.e. 1, 2, 3, 4, 5, or 6 amino acids, 1 to 10 amino acids of g1, i.e. 1, 2, 3, 4, 5, 6, 7, 8, 9, or 10 amino acids, and 0 to 3 amino acids of G1 spanning IgLCRC positions 128 to 133, i.e. 0, 1, 2, or 3 amino acids, is replaced with a continuous amino acid stretch comprising or consisting of at 1 to 10 amino acids of g2 spanning IgLCRC positions 109 to 127 of the immunoglobulin or immunoglobulin-like protein, i.e. 1, 2, 3, 4, 5, 6, 7, 8, 9 or 10 amino acids, preferably 1 to 6 amino acids ofF2 spanning IgLCRC positions 102 to 108, i.e. 1, 2, 3, 4, 5, or 6, 1 to 10 amino acids of g1 spanning IgLCRC positions 109 to 127 of the immunoglobulin or immunoglobulin-like protein, i.e. 1, 2, 3, 4, 5, 6, 7, 8, 9, or 10 amino acids, and 0 to 3 amino acids of G2 spanning IgLCRC positions 128 to 133, i.e. 0, 1, 2, or 3 amino acids, it is preferred that the total length of the replaced continuous amino acid stretch is between 3 to 20 amino acids more preferably 3 to 18 amino acids, even more preferably 3 to 15 amino acids.

Correspondingly, HR2 preferably has the following amino acid structure:
(i) at least 1 amino acid of a3 spanning IgLCRC positions 1 to 12 of the immunoglobulin or immunoglobulin-like protein is replaced with at least 1 amino acid of a4 spanning IgLCRC positions 1 to 12 of the immunoglobulin or immunoglobulin-like protein, in a preferred embodiment at least 4 to 12 amino acids, i.e. 4, 5, 6, 7, 8, 9, 10, 11, or 12, more preferably 6 to 8 amino acids of a3 spanning IgLCRC positions 1 to 12 are replaced with at least 4 to 12 amino acids, i.e. 4, 5, 6, 7, 8, 9, 10, 11, or 12, more preferably 6 to 8 amino acids of a4 spanning IgLCRC positions 1 to 12; and
(ii) at least 1 amino acid of c3 spanning IgLCRC positions 41 to 45 of the immunoglobulin or immunoglobulin-like protein is replaced with at least 1 amino acid of c4 spanning IgLCRC positions 41 to 45 of the immunoglobulin or immunoglobulin-like protein, in a preferred embodiment a continuous amino acid stretch consisting of 1 to 5 amino acid of c3 spanning IgLCRC positions 41 to 45 of the immunoglobulin or immunoglobulin-like protein, i.e. 1, 2, 3, 4, or 5 amino acids, and 1 to 6 amino acids of C3 spanning IgLCRC positions 46 to 52, i.e. 1, 2, 3, 4, 5, or 6 amino acids, more preferably a continuous amino acid stretch comprising or consisting of 2 to 5 amino acids of c3 spanning IgLCRC positions 41 to 45 and 4 to 6 amino acids of C3 spanning IgLCRC positions 46 to 52, is replaced with a continuous amino acid stretch consisting of 1 to 5 amino acid of c4 spanning IgLCRC positions 41 to 45 of the immunoglobulin or immunoglobulin-like protein, i.e. 1, 2, 3, 4, or 5, and 1 to 6 amino acids of C4 spanning IgLCRC positions 46 to 52, i.e. 1, 2, 3, 4, 5, or 6 amino acid, more preferably with a continuous amino acid stretch comprising or consisting of 2 to 5 amino acids of c4 spanning IgLCRC positions 41 to 45 and 4 to 6 amino acids of C4 spanning IgLCRC positions 46 to 52,
more preferably 1 to 5 amino acids of c3 are replaced with 1 to 5 amino acids of c4, preferably the residue replaced in Replacement 2 comprise IgLCRC positions 47 and 49,
preferably the total length of the replaced continuous amino acid stretch is between 5 to 11, more preferably 5 to 9 and even more preferably 5 to 7 amino acids; and
(iii) at least 1 amino acid of g3 spanning IgLCRC positions 109 to 127 of the immunoglobulin or immunoglobulin-like protein is replaced with at least 1 amino acid of g4 spanning IgLCRC positions 109 tp 127 of the immunoglobulin or immunoglobulin-like protein, in a preferred embodiment a continuous amino acid stretch comprising or consisting of 1 to 10 amino acids of g3 spanning IgLCRC positions 109 to 127 of the immunoglobulin or immunoglobulin-like protein, i.e. 1, 2, 3, 4, 5, 6, 7, 8, 9, or 10 amino acids, preferably 1 to 6 amino acids of F3 spanning IgLCRC positions 102 to 108, i.e. 1, 2, 3, 4, 5, or 6 amino acids, 1 to 10 amino acids of g1, i.e. 1, 2, 3, 4, 5, 6, 7, 8, 9, or 10 amino acids, and 0 to 3 amino acids of G3 spanning IgLCRC positions 128 to 133, i.e. 0, 1, 2, or 3 amino acids, is replaced with a continuous amino acid stretch comprising or consisting of at 1 to 10 amino acids of g4 spanning IgLCRC positions 109 to 127 of the immunoglobulin or immunoglobulin-like protein, i.e. 1, 2, 3, 4, 5, 6, 7, 8, 9 or 10 amino acids, preferably 1 to 6 amino acids of F4 spanning IgLCRC positions 102 to 108, i.e. 1, 2, 3, 4, 5, or 6, 1 to 10 amino acids of g3 spanning IgLCRC positions 109 to 127 of the immunoglobulin or immunoglobulin-like protein, i.e. 1, 2, 3, 4, 5, 6, 7, 8, 9, or 10 amino acids, and 0 to 3 amino acids of G4 spanning IgLCRC positions 128 to 133, i.e. 0, 1, 2, or 3 amino acids, it is preferred that the total length of the replaced continuous amino acid stretch is between 3 to 20 amino acids more preferably 3 to 18 amino acids, even more preferably 3 to 15 amino acids.

A more preferred embodiment of HR1 has the following amino acid structure:
(i) at least 4 to 12 amino acids, i.e. 4, 5, 6, 7, 8, 9, 10, 11, or 12, more preferably 6 to 8 amino acids of a3 spanning IgLCRC positions 1 to 12 are replaced with at least 4 to 12 amino acids, i.e. 4, 5, 6, 7, 8, 9, 10, 11, or 12, more preferably 6 to 8 amino acids of a4 spanning IgLCRC positions 1 to 12; and
(ii) a continuous amino acid stretch comprising or consisting of 2 to 5 amino acids of c3 spanning IgLCRC positions 41 to 45 and 4 to 6 amino acids of C3 spanning IgLCRC positions 46 to 52, is replaced with a continuous amino acid stretch comprising or consisting of 2 to 5 amino acids of c4 spanning IgLCRC positions 41 to 45 and 4 to 6 amino acids of C4 spanning IgLCRC positions 46 to 52,
or
1 to 5 amino acids of c3 are replaced with 1 to 5 amino acids of c4, more preferably the residue replaced in Replacement 2 comprise IgLCRC positions 47 and 49, preferably the total length of the replaced continuous amino acid stretch is between 5 to 11, more preferably 5 to 9 and even more preferably 5 to 7 amino acids; and
(iii) a continuous amino acid stretch comprising 1 to 6 amino acids of F1 spanning IgLCRC positions 102 to 108, i.e. 1, 2, 3, 4, 5, or 6 amino acids, 1 to 10 amino acids of g1, i.e. 1, 2, 3, 4, 5, 6, 7, 8, 9, or 10 amino acids, and 0 to 3 amino acids of G1 spanning IgLCRC positions 128 to 133, i.e. 0, 1, 2, or 3 amino acids, is replaced with a continuous stretch comprising 1 to 6 amino acids of F2 spanning IgLCRC positions 102 to 108, i.e. 1, 2, 3, 4, 5, or 6, 1 to 10 amino acids of g2 spanning IgLCRC positions 109 to 127 of the immunoglobulin or immunoglobulin-like protein, i.e. 1, 2, 3, 4, 5, 6, 7, 8, 9, or 10 amino acids, and 0 to 3 amino acids of G2 spanning IgLCRC positions 128 to 133, i.e. 0, 1, 2, or 3 amino acids, it is preferred that the total length of the replaced continuous amino acid stretch is between 3 to 20 amino acids more preferably 3 to 18 amino acids, even more preferably 3 to 15 amino acids.

Correspondingly, a more preferred HR2 has the following amino acid structure:
(i) at least 4 to 12 amino acids, i.e. 4, 5, 6, 7, 8, 9, 10, 11, or 12, more preferably 6 to 8 amino acids of a3 spanning IgLCRC positions 1 to 12 are replaced with at least 4 to 12 amino acids, i.e. 4, 5, 6, 7, 8, 9, 10, 11, or 12, more preferably 6 to 8 amino acids of a4 spanning IgLCRC positions 1 to 12; and
(ii) a continuous amino acid stretch comprising or consisting of 2 to 5 amino acids of c3 spanning IgLCRC positions 41 to 45 and 4 to 6 amino acids of C3 spanning IgLCRC positions 46 to 52, is replaced with a continuous amino acid stretch comprising or consisting of 2 to 5 amino acids of c4 spanning IgLCRC positions 41 to 45 and 4 to 6 amino acids of C4 spanning IgLCRC positions 46 to 52,
or
1 to 5 amino acids of c3 are replaced with 1 to 5 amino acids of c4, more preferably the residue replaced in Replacement 2 comprise IgLCRC positions 47 and 49, preferably the total length of the replaced continuous amino acid stretch is between 5 to 11, more preferably 5 to 9 and even more preferably 5 to 7 amino acids; and
(iii) a continuous amino acid stretch comprising 1 to 6 amino acids of F3 spanning IgLCRC positions 102 to 108, i.e. 1, 2, 3, 4, 5, or 6 amino acids, 1 to 10 amino acids of g3, i.e. 1, 2, 3, 4, 5, 6, 7, 8, 9, or 10 amino acids, and 0 to 3 amino acids of G3 spanning IgLCRC positions 128 to 133, i.e. 0, 1, 2, or 3 amino acids, is replaced with a continuous stretch comprising 1 to 6 amino acids of F4 spanning IgLCRC positions 102 to 108, i.e. 1, 2, 3, 4, 5, or 6, 1 to 10 amino acids of g4 spanning IgLCRC positions 109 to 127 of the immunoglobulin or immunoglobulin-like protein, i.e. 1, 2, 3, 4, 5, 6, 7, 8, 9, or 10 amino acids, and 0 to 3 amino acids of G4 spanning IgLCRC positions 128 to 133, i.e. 0, 1, 2, or 3 amino acids, it is preferred that the total length of the replaced continuous amino acid stretch is between 3 to 20 amino acids more preferably 3 to 18 amino acids, even more preferably 3 to 15 amino acids.

It is preferred that HRI comprises 6 to 8 amino acids of a2; between 5 to 11, more preferably 5 to 9 and even more preferably 5 to 7 amino acids of c2 and C2; and that a continuous amino acid stretch of between 3 to 20, more preferably 3 to 18, and even more preferably 3 to 15 amino acids of $1^{st}$ CRI are replaced with a continuous amino acid stretch of between 3 to 20, more preferably 3 to 18, and even more preferably 3 to 15 amino acids of the $2^{nd}$ CRI in replacement 3. It is preferred that HRII comprises 6 to 8 amino acids of a4; between 5 to 11, more preferably 5 to 9 and even more preferably 5 to 7 amino acids of c4 and C4; and that a continuous amino acid stretch of between 3 to 20, more preferably 3 to 18, and even more preferably 3 to 15 amino acids of $3^{rd}$ CRI are replaced with a continuous amino acid stretch of between 3 to 20, more preferably 3 to 18, and even more preferably 3 to 15 amino acids of the $4^{th}$ CRI in replacement 6.

It is also preferred that the replacement is not a null replacement, i.e. if amino acids of the $1^{st}$ CRI and the $2^{nd}$ CRI are identical at the IgLCRC positions to be replaced, this is not considered a replacement within the meaning of the present invention. Each replacement of amino acids of the $1^{st}$ CRI with amino acids of the $2^{nd}$ CRI and respectively, replacement of amino acids of the $3^{rd}$ CRI with amino acids of the $4^{th}$ CRI alters the sequence in the region of the $1^{st}$ and $3^{rd}$ CRI, respectively.

In a preferred embodiment the affinity of the binding of HRI to HRII is at least 50% of the affinity of the $1^{st}$ CRI to the $3^{rd}$ CRI, preferably the affinity of the binding is at least 60%, 70%, 80%, 90% or more. It is particularly preferred that the binding affinity of HRI to HRII is not altered in comparison to the binding affinity of the $1^{st}$ the the $3^{rd}$ CRI.

The skilled person is well aware how to determine binding affinity between two proteins. A preferred way of determining binding affinity in the context of the present invention is the use of BiaCore or quartz crystal microbalance (QCM) measurements.

To maintain the overall structure of the acceptor proteins, i.e. the $1^{st}$ CRI and the $3^{rd}$ CRI, it is preferred that acceptor amino acids of the $1^{st}$ CRI and the $3^{rd}$ CRI that are part of the antiparallel beta strands are replaced with the same number of donor amino acids. This applies to Replacement 2, which may include replacement of a part of C1 with a part of C2, Replacement 3, which may include replacement of parts of F1 and/or G1 with parts of F2 and/or G2, Replacement 5, which may include replacement of a part of C3 with a part of C4, and Replacement 6, which may include replacement of parts of F3 and/or G3 with parts of F4 and/or G4. Since the length of the intervening regions is more variable between two different human constants region of an immunoglobulin or immunoglobulin-like protein the length of the replaced intervening region in Replacements 1 to 6 is not necessarily identical. Typically, the number of replaced amino acids is identical to the number of the inserted amino acids, i.e. the overall length does not change, or the number of replaced amino acids is 1, 2 or 3 amino acids higher or lower than the number of inserted amino acids from the corresponding intervening region, e.g. 10 amino acids of a1 are replaced by 7 to 13 amino acids of a2. These principals for Replacements 1 to 6 are exemplary outlined in FIG. 8.

It is preferred that amino acids of the $1^{st}$ CRI at given IgLCRC positions are replaced with amino acids of the $2^{nd}$ CRI, which are located at identical IgLCRC positions. Similarly, it is preferred that amino acids of the $3^{rd}$ CRI at given IgLCRC positions are replaced with amino acids of the $4^{th}$ CRI, which are located at identical IgLCRC positions. In a most preferred embodiment the amino acids of the $1^{st}$ and $3^{rd}$ CRI, respectively, that are replaced with amino acids of the $2^{nd}$ and $4^{th}$ CRI, respectively, are at identical IgLCRC positions for both HRI and HRII.

For example, a HRI may comprise the amino acids of a2 at IgLCRC positions 7 to 13, which replace amino acids of a1 at IgLCRC positions 7 to 13 and/or HRII may comprise the amino acids of a4 at IgLCRC positions 7 to 13, which replace amino acids of a3 at IgLCRC positions 7 to 13.

In a particular embodiment the $1^{st}$ CRI and/or the $3^{rd}$ CRI are not comprised in amino acid chain I. In another particular embodiment the $1^{st}$ CRI and/or the $3^{rd}$ CRI are not comprised in amino acid chain II. In another particular embodiment the $1^{st}$ CRI and/or the $3^{rd}$ CRI are not comprised in amino acid chain I and II. The omission of the respective acceptor sequences prevents unwanted heterodimerization. However, in as long as only one of the $1^{st}$ or $3^{rd}$ CRI are comprised within HRI and HRII no heterodimerization will occur. Thus, the inclusion of a $1^{st}$ or 3 CRI will allow heterodimerization of the protein complex of the present invention with a further protein chain or complex. It is noted that due the replacements of amino acids within HRI and HRII, HRI is no longer considered in the context of the present invention to be a $1^{st}$ CRI and HRII is no longer considered to be a $3^{rd}$ CRI. Accordingly, it is preferred $1^{st}$ CRI and/or the $3^{rd}$ CRI are not comprised in amino acid chain I outside HRI and in amino acid chain II outside HRII.

In a preferred embodiment $2^{nd}$ and $4^{th}$ CRI are identical, more preferably specifically bind to each other under physiological conditions, i.e. form homodimers.

In a particular embodiment in which the $2^{nd}$ nd and $4^{th}$ CRI have an Fc-function it is preferred that the Fc-function is maintained when amino acid sequences of the $2^{nd}$ nd and $4^{th}$ CRI are inserted into the $1^{st}$ CRI of HRI and the $3^{rd}$ CRI of HRII, respectively. In the context of the present invention the Fc-function is maintained, if HRI has at least 30% of the Fc-function of the $2^{nd}$ CRI and HRII has at least 30% of the Fe-function of the $4^{th}$ CRI. In cases in which the $2^{nd}$ and $4^{th}$ CRI specifically bind to each other and have Fc function it is particularly preferred that the heterodimerized HRI and HRII have at least 30% of the Fc-function of the dimerized, preferably homodimerized $2^{nd}$ CRI and $4^{th}$ CRI.

In a preferred embodiment Replacement 1, Replacement 2, Replacement 3, Replacement 4, Replacement 5, and/or Replacement 6, preferably Replacement 1 to 6 does not introduce a new B cell epitope into HRI and/or HRII. Preferably, no new human B cell epitope. In a preferred embodiment Replacement 1, Replacement 2, Replacement 3, Replacement 4, Replacement 5, and/or Replacement 6, preferably Replacement 1 to 6 does not introduce a new T cell epitope into HRI and/or HRII. Preferably, no new human T cell epitope.

In particular embodiments, the immunoglobulin or immunoglobulin like proteins are selected from IgG1, Ig Kappa, T cell receptor (TCR) α, TCR β, neonatal Fc receptor (FcRn), β 2 microglobulin, Ig Lambda, IgG2, IgG3, IgG4, IgA1, IgA2, IgD, IgE, IgM, leukocyte antigen (LA) A or B and LA-D. Particularly, from human IgG1, Ig Kappa, T cell receptor (TCR) α, TCR β, neonatal Fe receptor (FcRn), β 2 microglobulin, Ig Lambda, IgG2, IgG3, IgG4, IgA1, IgA2, IgD, IgE, IgM, human leukocyte antigen (HLA) A or B and HLA-D.

In particular embodiments, $1^{st}$ CRI and $3^{rd}$ CRI are independently selected from the group consisting of a constant region of heavy chain 1 (CH1) of IgG1, preferably having an amino acid sequence according to SEQ ID NO: 1; Igκ constant region, preferably having an amino acid sequence according to SEQ ID NO: 18; constant region of TCR α, preferably having an amino acid sequence according to SEQ ID NO: 10; constant region of TCR β, preferably having an amino acid sequence according to SEQ ID NO: 11; FcRn alpha 3, preferably having an amino acid sequence according to SEQ ID NO: 12; β 2 micro globulin, preferably having an amino acid sequence according to SEQ ID NO: 13; Igλ constant region, preferably having an amino acid sequence according to SEQ ID NO: 19, 54, 55, 56, 57 or 58; IgG2, preferably having an amino acid sequence according to SEQ ID NO: 2, IgG3, preferably having an amino acid sequence according to SEQ ID NO: 3, IgG4, preferably having an amino acid sequence according to SEQ ID NO: 4, IgA1, preferably having an amino acid sequence according to SEQ ID NO: 5; IgA2, preferably having an amino acid sequence according to SEQ ID NO: 6; IgD, preferably having an amino acid sequence according to SEQ ID NO: 7; IgE, preferably having an amino acid sequence according to SEQ ID NO: 8; IgM, preferably having an amino acid sequence according to SEQ ID NO: 9; human leukocyte antigen (HLA) A, preferably having an amino acid sequence according to SEQ ID NO: 14, or HLA-B α3, preferably having an amino acid sequence according to SEQ ID NO: 15; HLA-D α2, preferably having an amino acid sequence according to SEQ ID NO: 16 and HLA-D β2, preferably having an amino acid sequence according to SEQ ID NO: 17.

In particular embodiments, the combinations of $1^{st}$ CRI and $3^{rd}$ CRI are selected from (i) $1^{st}$ CRI: CH1 of IgG1, IgG2, IgG3, IgG4, IgA1, IgA2, IgD, IgE, or IgM and $3^{rd}$ CRI: Igκ constant region and Igλ constant region, i.e. $1^{st}$ CRI CH1 of IgG1 and $3^{rd}$ CRI Igw, $1^{st}$ CRI CH1 of IgG2 and $3^{rd}$ CR Ig, $1^{st}$ CRI CH1 of IgG3 and $3^{rd}$ CRI Igκ, $1^{st}$ CRI CH1 of IgG4 and $3^{rd}$ CRI Igκ, $1^{st}$ CRI CH1 of IgA1 and $3^{rd}$ CRI Igκ, $1^{st}$ CRI CH1 of IgA2 and $3^{rd}$ CRI Igκ, $1^{st}$ CRI CH1 of IgD and $3^{rd}$ CRI Igκ, $1^{st}$ CRI CH1 of IgE and $3^{rd}$ CRI Igκ, $1^{st}$ CRI CH1 of IgM $3^{rd}$ CRI Igκ, $1^{st}$ CRI CH1 of IgG1 and $3^{rd}$ CRI Igλ, $1^{st}$ CRI CH1 of IgG2 and $3^{rd}$ CRI Igλ, $1^{st}$ CRI CH1 of IgG3 and $3^{rd}$ CRI Igh, $1^{st}$ CRI CH1 of IgG4 and $3^{rd}$ CRI Igλ, $1^{st}$ CRI CH1 of IgA1 and $3^{rd}$ CRI Igλ, $1^{st}$ CRI CH1 of IgA2 and $3^{rd}$ CRI Igλ, 1st CRI CH1 of IgD and $3^{rd}$ CRI Igλ, $1^{st}$ CRI CH1 of IgE and $3^{rd}$ CRI Igλ, or $1^{st}$ CRI CH1 of IgM and $3^{rd}$ CRI Igλ;

(ii) $1^{st}$ CRI: constant region of TCR α and $3^{rd}$ CRI: constant region of TCR β;

(iii) $1^{st}$ CRI: FcRn alpha 3; HLA-A α3; or HLA-B α3 and $3^{rd}$ CRI: β 2 micro globulin; and (iv) $1^{st}$ CRI: HLA-D α2 and $3^{rd}$ CRI: HLA-D β2.

In particular embodiments, the (i) $2^{nd}$ CRI and $4^{th}$ CRI are identical and selected from the group consisting of CH3 of IgG1, IgG2, IgG3, IgG4, IgA1, IgA2; CH1 of IgG1, IgG2, IgG3, IgG4, IgA1, IgA2, IgD, IgE, or IgM; or IgD; CH4 of IgE, or IgM; and Igκ or Igλ constant region, or the (ii) $2^{nd}$ CRI and $4^{th}$ CRI are selected individually from the group consisting of CH1 of IgG1, Igκ or Igλ constant region, CH1 of IgG2, IgG3, IgG4, IgA1, IgA2, IgD, IgE, or IgM; CH3 of IgG1, IgG2, IgG3, IgG4, IgA1, IgA2, or IgD and CH4 of IgE, or IgM.

In particular embodiments, $2^{nd}$ CRI and $4^{th}$ CRI are independently selected from the group consisting of a constant region of heavy chain 3 (CH3) of IgG1, preferably having an amino acid sequence according to SEQ ID NO: 45, a CH3 of IgG2, preferably having an amino acid sequence according to SEQ ID NO: 46, a CH3 of IgG3, preferably having an amino acid sequence according to SEQ ID NO: 47, a CH3 of IgG4, preferably having an amino acid sequence according to SEQ ID NO: 48, a constant region of heavy chain 4 (CH4) of IgM, preferably having an amino acid sequence according to SEQ ID NO: 49, a CH3 of IgA1, preferably having an amino acid sequence according to SEQ ID NO: 50, a CH3 of IgA2, preferably having an amino acid sequence according to SEQ ID NO: 51, a CH3 of IgD, preferably having an amino acid sequence according to SEQ ID NO: 52, and a CH4 of IgE, preferably having an amino acid sequence according to SEQ ID NO: 53.

Thus, in particular embodiments, the present invention provides the protein complex,
(i) wherein in Replacement 1 and/or 4, preferably in Replacement 1 and 4, all amino acids N-terminal to beta sheet A (Ig like constant region consensus (IgLCRC positions 1 to 12) of the $1^{st}$ CRI and/or 3rd CRI, preferably $1^{st}$ CRI and $3^{rd}$ CRI are replaced with all amino acids N-terminal to beta sheet A (IgLCRC positions 1 to 12) of the $2^{nd}$ CRI and/or 4th CRI, respectively, preferably of the $2^{nd}$ CRI and $4^{th}$ CRI;
(ii) wherein in Replacement 2 and/or 5, preferably in Replacement 2 and 5 amino acids at IgLCRC positions 41-45, 41-46, 41-47, 41-48, 41-49, 41-50, 41-51, 42-45, 42-46, 42-47, 42-48, 42-49, 42-50, 42-51, 43-45, 43-46, 43-47, 43-48, 43-49, 43-50, 43-51, 44-45, 44-46, 44-47, 44-48, 44-49, 44-50, 44-51, 45-45, 45-46, 45-47, 45-48, 45-49, 45-50 or 45-51 of the $1^{st}$ CRI and/or $3^{rd}$ CRI, preferably 1st CRI and $3^{rd}$ CRI are replaced with amino acids at IgCRC positions 41-45, 41-46, 41-47, 41-48, 41-49, 41-50, 41-51, 42-45, 42-46, 42-47, 42-48, 42-49, 42-50, 42-51, 43-45, 43-46, 43-47, 43-48, 43-49, 43-50, 43-51, 44-45, 44-46, 44-47, 44-48, 44-49, 44-50, 44-51, 45-45, 45-46, 45-47, 45-48, 45-49, 45-50 or 45-51 of the $2^{nd}$ CRI and/or $4^{th}$ CRI, respectively, preferably of the $2^{nd}$ CRI and $4^{th}$ CRI; and
(iii) wherein in Replacement 3 and/or 6, preferably in Replacement 3 and 6 amino acids at IgLCRC positions 103-127, 103-128, 103-129, 103-130, 103-131, 103-132, 104-127, 104-128, 104-129, 104-130, 104-131, 104-132, 105-127, 105-128, 105-129, 105-130, 105-131, 105-132, 106-127, 106-128, 106-129, 106-130, 106-131, 106-132, 107-127, 107-128, 107-129, 107-130, 107-131, 107-132, 108-127, 108-128, 108-129, 108-130, 108-131, 108-132, 109-127, 109-128, 109-129, 109-130, 109-131 or 109-132 of the $1^{st}$ CRI and/or $3^{rd}$ CRI, preferably $1^{st}$ CRI and $3^{rd}$ CRI are replaced with amino acids at IgLCRC positions 103-127, 103-128, 103-129, 103-130, 103-131, 103-132, 104-127, 104-128, 104-129, 104-130, 104-131, 104-132, 105-127, 105-128, 105-129, 105-130, 105-131, 105-132, 106-127, 106-128, 106-129, 106-130, 106-131, 106-132, 107-127, 107-128, 107-129, 107-130, 107-131, 107-132, 108-127, 108-128, 108-129, 108-130, 108-131, 108-132, 109-127, 109-128, 109-129, 109-130, 109-131 or 109-132 of the $2^{nd}$ CRI and/or $4^{th}$ CRI, respectively, preferably of the $2^{nd}$ CRI and $4^{t}$h CRI.

HRI predominantly comprises or consists of the amino acid sequence of the $1^{st}$ CRI while HRII predominantly comprises or consists of the amino acid sequence of the $3^{rd}$ CRI, i.e. the acceptor CRI. It is preferred that the total number of replaced amino acid in the $1^{st}$ and $3^{rd}$ CRI, respectively, i.e. the number of amino acids that are inserted into the $1^{st}$ CRI from the $2^{nd}$ CRI and into the $3^{rd}$ CRI from the $4^{th}$ CRI is between 14 to 30 amino acids, i.e. 14, 15, 16, 17, 18, 19, 20, 21, 22, 23, 24, 25, 26, 27, 28, 29, 30, in particular between 15 to 29, in particular 16 to 19.

In particular embodiments, the present invention provides the protein, wherein in addition to Replacement 1 to 6: (i) the amino acids of $1^{st}$ CRI or $3^{rd}$ CRI at IgLCRC positions 37, and/or 47, and/or 49, and/or 81, and/or 107 are replaced with amino acids of $2^{nd}$ CRI or $4^{th}$ CRI at IgLCRC positions 37, and/or 47, and/or 49, and/or 81, and/or 107. These replacements further improve the properties of HRI and HRII, e.g. stability or strength of dimerization. In particular embodiments the amino acids of $1^{st}$ CRI or $3^{rd}$ CRI at IgLCRC positions 37 and 47 are replaced and optionally amino acids at IgLCRC positions 49 and/or 81 and/or 107 are additionally replaced, with amino acids of $2^{nd}$ CRI or $4^{th}$ CRI at IgLCRC positions 37 and 47 and optionally with amino acids at IgLCRC positions 49 and/or 81 and/or 107. In particular embodiments the amino acids of $1^{st}$ CRI or $3^{rd}$ CRI at IgLCRC positions 37 and 49 are replaced and optionally amino acids at IgLCRC positions 47 and/or 81 and/or 107 are additionally replaced, with amino acids of $2^{nd}$ CRI or $4^{th}$ CRI at IgLCRC positions 37 and 49 and optionally with amino acids at IgLCRC positions 47 and/or 81 and/or 107. In particular embodiments the amino acids of $1^{st}$ CRI or $3^{rd}$ CRI at IgLCRC positions 37 and 81 are replaced and optionally amino acids at IgLCRC positions 47 and/or 49 and/or 107 are additionally replaced, with amino acids of $2^{nd}$ CRI or $4^{th}$ CRI at IgLCRC positions 37 and 81 and optionally with amino acids at IgLCRC positions 47 and/or 49 and/or 107. In particular embodiments the amino acids of $1^{st}$ CRI or $3^{rd}$ CRI at IgLCRC positions 37 and 107 are replaced and optionally amino acids at IgLCRC positions 47 and/or 49 and/or 81 are additionally replaced, with amino acids of $2^{nd}$ CRI or $4^{th}$ CRI at IgLCRC positions 37 and 107 and optionally with amino acids at IgLCRC positions 47 and/or 49 and/or 81. In particular embodiments the amino acids of $1^{st}$ CRI or $3^{rd}$ CRI at IgLCRC positions 47 and 49 are replaced and optionally amino acids at IgLCRC positions 37 and/or 81 and/or 107 are additionally replaced, with amino acids of $2^{nd}$ CRI or $4^{th}$ CRI at IgLCRC positions 47 and 49 and optionally with amino acids at IgLCRC positions 37 and/or 81 and/or 107. In particular embodiments the amino acids of $1^{st}$ CRI or $3^{rd}$ CRI at IgLCRC positions 47 and 81 are replaced and optionally amino acids at IgLCRC positions 37 and/or 49 and/or 107 are additionally replaced, with amino acids of $2^{nd}$ CRI or $4^{th}$ CRI at IgLCRC positions 47 and 81 and optionally with amino acids at IgLCRC positions 37 and/or 49 and/or 107. In particular embodiments the amino acids of $1^{st}$ CRI or $3^{rd}$ CRI at IgLCRC positions 47 and 107 are replaced and optionally amino acids at IgLCRC positions 37 and/or 49 and/or 81 are additionally replaced, with amino acids of $2^{nd}$ CRI or $4^{th}$ CRI at IgLCRC positions 47 and 107 and optionally with amino acids at IgLCRC positions 37 and/or 49 and/or 81. In particular embodiments the amino acids of $1^{st}$ CRI or $3^{rd}$ CRI at IgLCRC positions 49 and 81 are replaced and optionally amino acids at IgLCRC positions 37 and/or 47 and/or 107 are additionally replaced, with amino acids of $2^{nd}$ CRI or $4^{th}$ CRI at IgLCRC positions 49 and 81 and optionally with amino acids at IgLCRC positions 37 and/or 47 and/or 107. In particular embodiments the amino acids of $1^{st}$ CRI or $3^{rd}$ CRI at IgLCRC positions 49 and 107 are replaced and optionally amino acids at IgLCRC positions 37 and/or 47 and/or 81 are additionally replaced, with amino acids of $2^{nd}$ CRI or $4^{th}$ CRI at IgLCRC positions 49 and 107 and optionally with amino acids at IgLCRC positions 37 and/or 47 and/or 81.

In particular embodiments, HRI and HRII each comprise at least one Cys residue positioned to form a covalent bond between HRI and HRII at IgLCRC position 20 (CH1 of IgG2, IgG3, IgG4, or IgM), 21(CH1 of IgD), 135(CH1 of IgA1 or IgA2), 138(CH1 of IgG1 or IgE, CL of Igκ, CL of Igλ), 139 (constant domain of TCR β) or 141 (constant domain of TCRa), as depicted in FIG. 4, resulting from the following combinations of 1st CRI and 3rd CRI:

(i) 1st CRI: CH1 of IgG1, IgG2, IgG3, IgG4, IgA1, IgA2, IgD, IgE, or IgM and $3^{rd}$ CRI: Igκ constant region and/or Igγ constant region;

(ii) $1^{st}$ CRI: constant region of TCR α and $3^{rd}$ CRI: constant region of TCR β.

In a particular embodiment, the present invention provides the protein complex, wherein HRI and HRII are comprised in the protein complex and respectively have the amino acid sequence according to SEQ ID NO: 20 and 21, SEQ ID NO: 22 and 23, SEQ ID NO: 24 and 25, SEQ ID NO: 26 and 27, SEQ ID NO: 28 and 32, SEQ ID NO: 28 and 33, SEQ ID NO: 31 and 29 and SEQ ID NO: 31 and 30.

In a particular embodiment, amino acid chain I and/or amino acid chain II further comprise one or more amino acid elements selected from the group consisting of a CH2 or CH3 domain of an antibody; one or more antigen specific ligand (ASL), preferably selected from the group consisting of a Fv, a single-chain Fv (scFv), a disulfide-stabilized Fv, a disulfide-stabilized scFv, a Fab, a single-chain Fab, a single domain antibody, a variable heavy chain domain (VH), a variable light chain domain (VL), two or more connected variable chain domains, forming e.g. Diabody like binding sites, a Nanobody, a VHH, one or more antibody-like binding proteins (e.g. Darpins, Anticalins, Affibodies, fibronectin-like domains, etc.); an antibody hinge region (HR), one or more linker sequences (L), one or more cytokines (C, e.g. TNF superfamily members, interleukines (IL, e.g. IL-2), interferons (e.g. IFNg), growth factors, hormones, ligands, peptides, receptor fragments with ligand-binding activity, chelators, enzymes, coagulation factors, and anti-coagulants, and derivatives thereof.

In a particular embodiment, amino acid chain I comprises, positioned from N- to C-terminus:

(i) ASL specific to antigen 1 (ASLAn1)-L-CH2-HRI;
(ii) CH2-HRI;
(iii) ASLAn1-L-CH2-HRI;
(iv) CH2-HRI-L-ASLAn1;
(v) CH2-HRI;
(vi) CH2-HRI-L-ASLAn1;
(vii) ASLAn1-L-CH2-HRI-L-ASL specific to antigen 2 (ASLAn2);
(viii) ASLAn1-L-CH2-HRI;
(ix) CH2-HRI;
(x) CH2-HRI-L-ASLAn1;
(xi) ASLAn1-L-CH2-HRI-L-ASLAn2;
(xii) ASLAn1-L-CH2-HRI-L-ASLAn2;
(xiii) CH2-HRI-L-ASLAn1;
(xiv) ASLAn1-L-CH2-HRI;
(xv) ASLAn1-L-CH2-HRI-L-ASLAn2;
(xvi) Any amino acid chain as described in (i) to (xv) containing a hinge region N-terminal to CH2
(xvii) Any amino acid chain as described in (i) to (xvi), containing a cytokine (C) or interleukine (IL) instead of one or more ASL
(xviii) ASLAn1a (e.g. VL)-HRIa+ASLAn1b (e.g. VH)-HRIIa-L/HR-CH2-HRIb and amino acid chain II comprises, positioned from N- to C-terminus:

(i) CH2-HRII;
(ii) ASLAn1-L-CH2-HRII;
(iii) ASL specific to antigen 2 (ASLAn2)-L-CH2-HRII;
(iv) CH2-HRII;
(v) CH2-HRI-L-ASLAn1;
(vi) CH2-HRI-L-ASLAn2;
(vii) CH2-HRII;
(viii) CH2-HRII-L-ASLAn2;
(ix) ASLAn 1-L-CH2-HRII-L-ASLAn2;
(x) ASLAn2-L-CH2-HRII;
(xi) CH2-HRII-L-ASL specific to antigen 3 (ASLAn3);
(xii) ASLAn3-L-CH2-HRII;
(xiii) ASLAn2-L-CH2-HRII-L-ASLAn3;
(xiv) ASLAn2-L-CH2-HRII-L-ASLAn3;
(xiv) ASLAn3-L-CH2-HRII-L-ASL specific to antigen 4 (ASLAn4);
(xvi) Any amino acid chain as described in (i) to (xv) containing a hinge region N-terminal to CH2
(xvii) Any amino acid chain as described in (i) to (xvi), containing a cytokine (C) or interleukin instead of one or more ASL
(xviii) ASLAn2a (e.g. VL)-HRIc+ASLAn2b (e.g. VH)-HRIIc-L/HR-CH2-HRIIb In a particular embodiment, amino acid chain I comprises one or more antigen specific ligands (ASL) and/or one or more effector molecules and amino acid chain II comprises one or more antigen specific ligands (ASL) and/or one or more effector molecules and, wherein the ASL modules are selected from a group of molecules, specifically binding to e.g. cell surface proteins (receptor, adhesion molecule, channel, transporter, etc.), hormones, growth factors, cytokines, ligands, serum proteins, coagulation factors, fibrinolytic factors, chemokines, enzymes and, wherein the effector molecules are selected from a group of molecules e.g. cell surface proteins (receptor, adhesion molecule, channel, transporter, etc.), hormones, growth factors, cytokines, ligands, serum proteins, coagulation factors, fibrinolytic factors, chemokines, enzymes.

In a particular embodiment, the invention provides amino acid chain I or II, preferably a combination of amino acid chains, wherein chain I and chain II comprise, essentially consist or consist of the amino acid sequence according to SEQ ID NO: 41 and SEQ ID NO: 42 SEQ ID NO: 34 and SEQ ID NO: 35, SEQ ID NO: 43 and SEQ ID NO: 44, SEQ ID NO: 36 and SEQ ID NO: 37 (scFv13.7-Fc1k), SEQ ID NO: 36 and SEQ ID NO: 38 (scFv13.7-CD3-Hinge-Fc1k), SEQ ID NO: 39 and SEQ ID NO: 38 (scFv3-43-CD3-Hinge-Fc1k) or SEQ ID NO: 40 and SEQ ID NO: 38 (scFvhuMCSP-CD3-Hinge-Fc1k), respectively and variants thereof having at least 70%, more preferably at least 75%, more preferably at least 80%, more preferably at least 85%, more preferably at least 90%, more preferably at least 95% and even more preferably at least 98% sequence identity to the respectively indicated sequences and which are capable of heterodimerizing and specifically binding to the same target.

In a second aspect, the invention provides a nucleic acid encoding the amino acid chain I and/or II.

In a third aspect, the invention provides a vector comprising the nucleic acid of the second aspect.

In a fourth aspect, the present invention provides a method of determining (defining) the amino acid sequence of HRI of a, amino acid chain I and/or of HRII of an amino acid sequence II comprising the steps of:
(i) selecting a $1^{st}$ CRI, a $2^{nd}$ CRI, a $3^{rd}$ CRI, and a $4^{th}$ CRI;
(ii) determining (defining) the seven beta strands A, B, C, D, E, F and G of the $1^{st}$ CRI, $2^{nd}$ CRI, $3^{rd}$ CRI, and $4^{th}$ CRI, intervening sequences b, c, d, e, f, and g of the $1^{st}$ CRI, $2^{nd}$ CRI, $3^{rd}$ CRI, and $4^{th}$ CRI, N- and C-terminal sequences a and h, respectively of the $1^{st}$ CRI, $2^{nd}$ CRI, $3^{rd}$ CRI, and $4^{th}$ CRI;
(iii) replacing at least 1 amino acid of a of the $1^{st}$ CRI with at least 1 amino acid of a of the $2^{nd}$ (Replacement 1); replacing at least 1 amino acid of c of the $1^{st}$ CRI with at least 1 amino acids of c of the $2^{nd}$ CRI (Replacement 2); replacing at least 1 amino acid of g of the $1^{st}$ CRI with at least 1 amino acid of g of the $2^{nd}$ CRI (Replacement 3); replacing at least 1 amino acid of a of the $3^{rd}$ CRI with at least 1 amino acid of a of the $4^{th}$ CRI (Replacement 4); replacing at least 1 amino acid of c of the $3^{rd}$ with at least 1 amino acid of c of the $4^{th}$ CRI (Replacement 5); and replacing at least 1 amino acid of g of the 3 with at least 1 amino acid g of the $4^{th}$ CRI (Replacement 6),
wherein the $1^{st}$ CRI and the $3^{rd}$ CRI are different from each other and specifically bind to each other under physiological conditions.

It is preferred that both HRI and HRII are defined, since both are required to allow heterodimerization of the two amino acids chains.

Step (ii) involves for each given CRI a sequence alignment and the designation of the respective N- and C-terminal amino acids of beta strand and intervening sequence.

In a fifth aspect, the present invention provides a method of producing amino acid chain I with the HRI sequence determined (defined) and/or amino acid chain II with the HRII sequence determined (defined) comprising the step of introducing a nucleic acid encoding the amino acid chain I and/or amino acid chain II into a host cell and expressing amino acid chain I and/or II.

In a sixth aspect, the invention provides the protein complex for use as a medicament.

In an embodiment, the protein complex is for use in the prophylaxis, treatment or diagnosis of a disorder or disease such as but not limited to inflammatory diseases, autoimmune diseases, allergic diseases, proliferative diseases, cancer type diseases, cutaneous conditions, endocrine diseases, eye diseases and disorders, genetic disorders, metabolic diseases, infectious diseases, intestinal diseases, neurological disorders, and mental illness.

The following examples are merely illustrative of the present invention and should not be construed to limit the scope of the invention as indicated by the appended claims in any way.

EXAMPLES

Example 1: Heterodimerizing Fc Part

A heterodimerizing antibody Fc part was generated using a combination of IgG1 CH1 and Igkappa constant domains as 2nd CRI and 4th CRI, respectively, together with IgG1 CH3 residues as 1st CRI and 3rd CRI sequences with the sequence compositions 1, 2 (#43-51) and 3 (#103-132) in case of CH1-CH3 combination (CH31) as well as 1, 2 (#45-51) and 3 (#103-129) in case of CLk-CH3 combination (CH3k). In addition to the indicated sequences, residue 37 of CH3 was transferred to the CLk 3rd CRI sequence with respect to its potential involvement in the structural stabilization of CH3 elements, introduced in terms of sequences 1 to 3. Sequences of CH31 and CH3k are displayed in FIG. 8. In order to generate a fully functional Fc part, designated Fc1k, both domains were fused the C-terminus of IgG hinge-CH2 domains (FIG. 9). In order to substantiate the heterodimerization potential of Fc1k, two molecules were cloned and produced, that both contained scFv13.7 (anti-tumor necrosis factor receptor 1, TNFR1) connected to a first Fc chain via an IgG1 hinge sequence and a second chain, comprising only the hinge sequence and the Fcc domains (FIG. 10). While one construct carried the CH2-CH31/CH2-CH3k heterodimerizing Fc part, the second molecule contained the unmodified CH2-CH3 wildtype Fc part. Both proteins were purified by protein A affinity chromatography. Under reducing conditions scFv13.7-Hinge-Fc1k showed two major bands, corresponding to the calculated molecular weights (FIG. 11*a-c*, heavy chain 50 kDa, light chain 24 kDa). In addition, a second band of lower molecular weight appeared below the light chain, indicating un- or less glycosylated light chain. Under non-reducing conditions, one dominating band was visible, resembling the correctly formed heterodimer (74 kDa). However, additional bands at lower molecular weights indicated the existence of monomeric heavy chain or dimerized light chain (ca. 50 kDa) and smaller degradation products or unligated light chain (ca. 25 kDa). This observation was confirmed by SEC analysis. The dominating peak at ca. 14.5 min represented correctly assembled scFv13.7-Fc1k protein, while the minor peak at ca. 16.5 min could be attributed again to monomeric heavy chain or dimerized light chain. In contrast, scFv13.7-Fc additionally formed dimers of the heavy chain, as visible in SDS-PAGE (ca. 160 kDa, FIG. 11*d-e*) and SEC analysis (ca. 13.8 min). The decrease of minor bands in SDS-PAGE (ca. 50 kDa) or minor peaks in SEC analysis (ca. 16.5 min), as compared to scFv13.7-Fc1k, indicate a minor tendency of light chains to form homodimers, supporting the assumption, that minor bands in the case of scFv13.7-Fc1k rather represent monomeric heavy chain than dimerized light chain. Additional minor peaks of shorter retention times observed in SEC analysis, indicating aggregated or multimerized protein species, were observed for both proteins.

Example 2: Fv13.7-Fc1k

A Fab-like antibody format that comprises a functional, bivalent Fc proportion was created upon fusing the variable domains of Fab 13.7 each to one Fc chain, composed of CH2 and CH31 or CH2 and CH3k via a GTG₃SG linker (FIG. 12). In addition, mutations in CH2 (A327G, A330S and P331S, EU numbering) were introduced in order to avoid binding to Fcγ-receptors and complement protein C1q (Richter et al., 2013). Codon-optimized DNA sequences of CH2-CH31 and CH2-CH3k (GeneArt™), containing the N-terminal linker (GTG₃SG) were inserted into pSecTagA-L1, containing either VH13.7 or VL13.7 after digestion by KpnI and EcoRI.

Fv13.7-Fc1k was expressed in transiently transfected HEK293-6E cells after co-administration of two plasmids encoding for either VH13.7-CH2-CH31 or VL13.7-CH2-CH3k using polyethylenimine as transfection reagent. Protein secreted into the cell culture supernatant was purified by Protein A affinity chromatography (14.6 mg/L, see Table 1), followed by a preparative size exclusion chromatography step (SEC, final yield 4.1 mg/L). Individual fractions were tested for their ability to induce TNFRI activation. Negative fractions (data not shown), indicating correctly assembled protein (cartoon see FIG. 13a), were pooled. Fv13.7-Fc1k showed two bands of slightly differing size under reducing conditions and one band under non-reducing conditions in SDS-PAGE, all corresponding to the calculated molecular weights (FIG. 13b). Similarly, under native conditions in SEC analysis one major peak was visible, accompanied by a minor peak, representing a marginal proportion of aggregated or multimerized protein species (FIG. 13c).

TABLE 1

Production and purification of Fv13.7-Fc1k

| Protein | Conc. [mg/ml] | SampleVol. [ml] | total [mg] | Prot. Culture Vol. [L] | Yield [mg/L] |
|---|---|---|---|---|---|
| Protein A | 4.01 | 2.40 | 9.6 | 0.66 | 14.6 |
| Concentrated | 12.02 | 0.50 | 6.0 | 0.66 | 9.1 |
| FPLC | 0.90 | 3.00 | 2.7 | 0.66 | 4.1 |

Fv13.7-Fc1k bound to immobilized human TNFR1 in ELISA with an $EC_{50}$ value of 1.2 nM, representing a 1.9-fold reduced binding affinity as compared with Fab13.7 (Table 2, FIG. 14). Consistent with Fab13.7, Fv13.7-Fc1k did not induce TNFR1-mediated IL-8 release from HT1080 cells, which was in contrast to the receptor activation observed in the case of ATROSAB (FIG. 15a). Moreover, Fv13.7-Fc1k inhibited TNFR1-mediated IL-8 release, induced by 0.1 nM TNF from HT1080 cells, with an $IC_{50}$ value of 39.7 nM. In comparison to Fab13.7, Fv13.7-Fc1k revealed a 1.5-fold reduced bioactivity, however, when compared to ATROSAB, the inhibitory potential was increased by a factor of 2.5 (FIG. 15b, Table 2). In order to further clarify the potential of Fv13.7-Fc1k to be applied as therapeutic agent, pharmacokinetic characteristics were determined in vivo using human $TNFR1_{ecd}$ knock-in mice, which are genetically engineered to express the extracellular domain of human TNFR1 instead of the mouse protein. In the case of ATROSAB, a terminal half-life of 29.1 h and an area under the curve of 526.4 h*μg/ml, representing a relative measure for the bioavailability of a therapeutic agent, were determined (FIG. 16, Table 2). Due to its large molecular weight and the possibility of FcRn-mediated drug recycling, higher values would be expected for ATROSAB. However, under the here applied experimental conditions of low dose injection (25 μg/animai) and the presence of the targeted antigen (human TNFR1), ATROSAB was cleared by a secondary effect of target-mediated clearance (Richter et al. in preparation). Fv13.7-Fc1k revealed reduced values for terminal half-life and area under the curve by factors of 2.1 and 2.0, respectively, when compared to ATROSAB. More important, however, in comparison to Fab13.7, Fv13.7-Fc1k showed a 10-fold improved terminal half-life and a 65-fold increased area under the curve.

TABLE 2

Functional data of Fv13.7-Fc1k

| Molecule | ELISA Binding $EC_{50}$ [nM] | IL-8 Inhibition $IC_{50}$ [nM] | Initial Half-Life [h] | Terminal Half-Life [h] | Area Under The Curve [h*μg/ml] |
|---|---|---|---|---|---|
| ATROSAB |  | 97.78 | 0.59 ± 0.21 | 29.09 ± 7.60 | 526.44 ± 87.94 |
| Fab13.7 | 0.61 | 26.32 | 0.08 ± 0.06 | 1.36 ± 0.91 | 4.03 ± 0.34 |
| Fv13.7-Fc1k | 1.18 | 39.71 | 2.83 ± 1.85 | 13.68 ± 2.43 | 261.84 ± 68.61 |

Examples 3-6: Generation of Bi- or Trivalent and Bispecific scFv-Fe Fusion Proteins In addition, the heterodimerizing Fc part Fc1k was used to generate bi- or tri-valent and bispecific scFv-Fc fusion proteins in order to retarget CD3 expressing T cells to FAP-expressing tumor cells or to tumor cells that are surrounded by FAP-expressing fibroblasts. Hence scFvhu36 (FAP-targeting) and scFvhuU3 (CD3-targeting) moieties were fused to either the N- or the C-terminus of Fc1k. All constructs were also created using a IgG1 hinge region without cysteins in order to investigate the importance of hinge-mediated covalent linkages. The created constructs contained either one FAP-targeting moiety and one CD3-targeting moiety, both at the N-terminus ($FAP_N$-$CH3_N$-hFc [with cysteines in the hinge region], example 3a and $FAP_N$-$CH3_N$-Fc[without cysteines in the hinge region], example 3b, FIG. 17) or one FAP-targeting moiety at the N-terminus and one CD3-targeting moiety at the C-terminus ($FAP_{NC}$-$CH3_C$-hFc, example 4a and $FAP_N$-$CH3_C$-Fc, example 4b, FIG. 18). Moreover, constructs containing two FAP-targeting moieties at the N-terminus and one CD3-targeting moiety at the C-terminus ($FAP_{NN}$-CH3c-hFc, example 5a and $FAP_{NN}$-$CH3_C$-Fc, example 5b, FIG. 19) were created as well as constructs, containing one FAP-targeting moiety at the N-terminus as well as one FAP-targeting moiety at the C-terminus and one CD3-targeting moiety at the C-terminus ($FAP_{NC}$-$CH3_C$-hFc, example 6a and $FAP_{NC}$-$CH3_C$-Fc, example 6b, FIG. 20). Production and characterization of these fusion proteins is still ongoing.

Example 7: Generation of Bivalent IgG-Like Antibodies

The herein presented toolbox for the generation of heterodimerizing Ig domains provides the possibility to generate bivalent IgG-like antibodies. Therefore, a heterodimerizing Fc part has to be generated, wherein the 1st CRI and 3rd CRI sequences cannot be retrieved from CH1 and CLkappa/lambda. 1st CRI and 3rd CRI sequences could be used e.g. from FcRn-alpha3 and beta2-microglobulin in combination with 2nd CRI and 4th CRI sequences from CH3, resulting in the new domains FcRnH3 and b2mH3. The intended donor sequence composition (1, 2[41-45], 3[109-127] and additional residues [47, 49 and 107]) is shown in FIG. 21a. Analog to Fc1k, a complete 5 Fc part (Fcb2Rn) could further be generated.

In order to generate an IgG-like molecule, one Fab arm can remain untouched. However, in order to avoid mispairing of heavy and light chains, another heterodimerizing domain pair has to be generated as basis for a Fab-like second IgG arm. 1st CRI and 3rd CRI sequences could be used e.g. from TCR-alpha2 and TCR-beta2 together with 2nd CRI and 4th CRI sequences from CH1 and CLk, respectively, resulting in the new domains TCRaH1 and TCRbLk, which would assemble to FabTCR after fusion to the C-termini of VH and VL of the desired specificity. The intended 2nd CRI and 4th CRI sequence composition (1, 2[41-45], 3[109-127] and additional residue [81]) is shown in FIG. 21a. The whole molecular arrangement is shown in FIG. 22.

Example 8: Fv13.7x-Fc1k

A Fab-like antibody format that comprises a functional, bivalent Fc proportion was created upon fusing the variable domains of Fab13.7 each to one Fc chain, composed of CH2 and CH31 or CH2 and CH3k via a GTG$_3$SG linker (FIG. 23). In addition, mutations in CH2 (A327G, A330S and P331S, EU numbering) were introduced in order to avoid binding to Fcγ-receptors and complement protein C1q (Richter et al. 2013). Codon-optimized DNA sequences of CH2-CH31 and CH2-CH3k (GeneArt™), containing the N-terminal linker (GTG$_3$SG) were inserted into pSecTagA-L1, containing either VH13.7 or VL13.7 after digestion by KpnI and EcoRI. Contrary to the previously described Fv13.7-Fc1k (Example 2), in the case of Fv13.7x-Fc1k, VH13.7 was fused N-terminally to the polypeptide chain containing CH2 and CH3k, while VL13.7 was fused N-terminally to the polypeptide chain containing CH2 and CH31.

Fv13.7x-Fc1k was expressed in transiently transfected HEK293-6E cells after co-administration of two plasmids encoding for either VH13.7-CH2-CH3k or VL13.7-CH2-CH31, using polyethylenimine as transfection reagent. Protein secreted into the cell culture supernatant was purified by Protein A affinity chromatography, followed by a preparative size exclusion chromatography step. Collected fractions of the peak, representing the intact and heterodimerically assembled protein (FIG. 24a) were pooled. Following Protein L purification, Fv1 3.7x-Fc1k showed two bands of different size under reducing conditions and one band under non-reducing conditions in SDS-PAGE, all corresponding to the calculated molecular weights (FIG. 24b). Similarly, under native conditions in SEC analysis one major peak was visible, accompanied by minor peak, representing a marginal proportion of aggregated/multimerized protein species or, as well, a minimal proportion of free single polypeptide chain (FIG. 24c).

Fv13.7x-Fc1k bound to immobilized human TNFR1 in ELISA with an EC$_{50}$ value of 1.9 nM, representing a 2.1-fold reduced binding affinity as compared with Fab13.7 (Table 3, FIG. 24d). Consistent with Fab13.7, Fv13.7x-Fc1k did not induce TNFR1-mediated IL-8 release from HT1080 cells (FIG. 24e), which was in contrast to the receptor activation, previously observed in the case of ATROSAB (FIG. 15a). Of note, the activation of TNFR1 on the surface of HT1080 cells by ATROSAB in the IL-8 release assay could not consistently be observed, most likely due to variations in the used materials (ELISA Kit) or cellular batch to batch variations. However, Fv13.7x-Fc1k inhibited TNFR1-mediated IL-8 release, induced by 0.1 nM TNF, with an IC$_{50}$ value of 48 nM. In comparison to Fab13.7, Fv13.7x-Fc1k revealed a 3.7-fold reduced bioactivity, however, when compared to ATROSAB, the inhibitory potential was increased by a factor of 2.8 (FIG. 24f, Table 3). Further production and characterization of this fusion protein is still ongoing.

TABLE 3

| | Functional data of Fv13.7x-Fc1k | |
|---|---|---|
| Molecule | ELISA Binding EC$_{50}$ [nM] | IL-8 Inhibition IC$_{50}$ [nM] |
| ATROSAB | 0.4 | 136 |
| Fab13.7 | 0.9 | 13 |
| Fv13.7x-Fc1k | 1.9 | 48 |

Example 9: FvCD3-Fc1k-scFvHer32

A bispecific molecule, based on the Fab-like antibody format as described in example 2 and 8, was generated upon fusing two single-chain variable fragments (scFv) of a Her3-targeting antibody to the C-termini of CH31- and CH3k-containing polypeptide chains of a CD3-specifiv Fv-Fc1k module (FIG. 25). The connection was accomplished by a hinge-derived polypeptide linker (Table 5) using the restriction sites KasI and EcoRI. In general this format holds the potential to be used as platform technology for the development of diverse bi- and multi-specific immune cell engaging molecules upon replacement of the target-binding scFv proportions with alternative scFvs or any kind of binding domain directed against one or, possibly, two different tumor antigens or tumor associated antigens. Production and characterization of this fusion protein is still ongoing.

Example 10: Bispecific scFv-Fc Fusion Protein Specific for Human TNFR1 and CD3

Based on the molecule described as example 3a, another bispecific scFv-Fc fusion protein was generated (13.7$_N$-CD3$_N$-hFc1k), containing scFv parts directed against CD3 and human TNFR1, which were fused to the N-terminus of the hinge-containing chains of Felk (FIG. 26).

13.7$_N$-CD3$_N$-hFc1k was produced in HEK293-6E cells after transient transfection of two pSecTagAL1 vectors, each encoding one of the two polypeptide chains, using polyethylenimine as transfection reagent. SDS-PAGE analysis after purification using Protein A affinity chromatography and subsequent preparative SEC revealed two bands under reducing conditions and one dominating band under non-reducing conditions, both representing the calculated molecular weights (FIG. 27b). Minor bands observed under both conditions might represent partial differences in the glycosylation status of the expressed protein. Moreover, 13.7$_N$-CD3$_N$-hFc1k showed one single peak in analytical SEC (FIG. 27c). Binding of 13.7$_N$-CD3$_N$-hFc1k to a human TNFR1-Fc fusion protein was analyzed by ELISA, revealing an EC$_{50}$ value of 3.5 nM (FIG. 27d, Table 4). In addition, 13.7$_N$-CD3$_N$-hFc1k bound to TNFR1 and CD3 on the surface of HT1080 (FIG. 27*e*) and CD3-transfected Jurkat cells (FIG. 27*f*) with EC$_{50}$ values of 3.7 nM and 1.6 nM, respectively. Finally, the bioactivity of 13.7$_N$-CD3$_N$-hFc1k, reflected by the ability to reduce target cell viability (TNFR1-expressing HT1080 cells) in the presence of peripheral blood mononuclear cells (PBMC), was determined with an IC$_{50}$ value of 0.8 nM and a residual viability of 40% at concentrations above 10 nM (FIG. 27*g*). Further production and characterization of this fusion protein is still ongoing.

Example 11: Bispecific scFv-Fc Fusion Protein Specific for Human Her3 and CD3

Based on the molecule described as example 3a, another bispecific scFv-Fc fusion protein was generated (Her3$_N$-CD3$_N$-hFc1k) containing scFv parts directed against CD3 and Her3 (Human epidermal growth factor receptor 3, also named ErbB3), which were fused to the N-terminus of the hinge-containing chains of Fc1k (FIG. 28).

Her3$_N$-CD3$_N$-hFc1k was produced in HEK293-6E cells after transient transfection of two pSecTagAL1 vectors, each encoding one of the two polypeptide chains, using polyethylenimine as transfection reagent. SDS-PAGE analysis after purification by Protein A affinity chromatography and subsequent preparative SEC revealed two bands under reducing conditions and one dominating band under non-reducing conditions, both representing the calculated molecular weights (FIG. 29*b*). Minor bands observed under both conditions might represent partial differences in the glycosylation status of the expressed protein. Moreover, Her3$_N$-CD3$_N$-hFc1k showed one single peak in analytical SEC (FIG. 29*c*). Binding of Her3$_N$-CD3$_N$-hFc1k to an immobilized Her3-Fc fusion protein was analyzed by ELISA, revealing an EC$_{50}$ value of 1.0 nM (FIG. 29*d*, Table 4). Further production and characterization of this fusion protein is still ongoing.

Example 12: Bispecific scFv-Fc Fusion Protein Specific for Human MCSP and CD3

Based on the molecule described as example 3a, another bispecific scFv-Fc fusion protein was generated (MCSP$_N$-CD3$_N$-hFc1k) containing scFv parts directed against CD3 and human MCSP (Melanoma-associated chondroitin sulfate proteoglycan), which were fused to the N-terminus of the hinge-containing chains of Fc1k (FIG. 30).

MCSP$_N$-CD3$_N$-hFc1k was produced in HEK293-6E cells after transient transfection of two pSecTagAL1 vectors, each encoding one of the two polypeptide chains, using polyethylenimine as transfection reagent. SDS-PAGE analysis after purification by Protein A affinity chromatography and subsequent preparative SEC, revealed two bands under reducing conditions and one dominating band under non-reducing conditions, both corresponding to the calculated molecular weights (FIG. 31*b*). Minor bands observed under both conditions might represent partial differences in the glycosylation status of the expressed protein. Moreover, MCSP$_N$-CD3$_N$-hFc1k showed one single peak in analytical SEC (FIG. 31*c*). The bioactivity of MCSP$_N$-CD3$_N$-hFc1k, reflected by the ability to reduce target cell viability in the presence of peripheral blood mononuclear cells (PBMC), was determined with an IC$_{50}$ value of 0.2 nM, using MCSP-expressing WM35 cells (FIG. 31*d*, Table 4). Further production and characterization of this fusion protein is still ongoing.

Example 13: Bispecific scFv-Fc Fusion Protein Specific for Her3 and CD3 with Opposite Orientation Based on the molecule described as example 4a, another bispecific scFv-Fc fusion protein was generated (Her3$_N$-CD3$_C$-hFc1k) containing scFv parts directed against CD3 and Her3 (Human epidermal growth factor receptor 3, also named ErbB3), which were fused to the N-terminus of the hinge-containing CH2-CH31 chain and to the C-terminus of the CH2-CH3k chain of Fc1k, respectively (FIG. 32).

Her3$_N$-CD3$_C$-hFc1k was produced in HEK293-6E cells after transient transfection of two pSecTagAL1 vectors, each encoding one of the two polypeptide chains, using polyethylenimine as transfection reagent. SDS-PAGE analysis after purification by Protein A affinity chromatography and subsequent preparative SEC revealed two bands under reducing conditions and one dominating band under non-reducing conditions, both corresponding to the calculated molecular weights (FIG. 33*b*). Minor bands observed under both conditions might represent partial differences in the glycosylation status of the expressed protein. Binding of Her3$_N$-CD3$_C$-hFc1k to an immobilized Her3-Fc fusion protein was analyzed by ELISA, revealing an EC$_{50}$ value of 0.1 nM (FIG. 33*c*, Table 4). Further production and characterization of this fusion protein is still ongoing.

TABLE 4

Functional data of Examples 10-13.

| Molecule | ELISA Binding EC$_{50}$ [nM] | FACS Target Binding EC$_{50}$ [nM] | FACS CD3 Binding EC$_{50}$ [nM] | Cytotxicity IC$_{50}$ [nM] |
|---|---|---|---|---|
| 13.7$_N$-CD3$_N$-hFc1k | 3.5 | 3.7 | 1.6 | 0.8 |
| Her3$_N$-CD3$_N$-hFc1k | 1.0 | | | |
| MCSP$_N$-CD3$_N$-hFc1k | | | | 0.2 |
| Her3$_N$-CD3$_C$-hFc1k | 0.1 | | | |

TABLE 5

Linker variants used in Examples 1-13.

| Example | Molecule | N-terminal domain | Linker Sequence | C-terminal domain |
|---|---|---|---|---|
| 2 and 8 | Fv-Fc1k | VH/VL | GTGGGSG | CH2 |
| 3a to 6 | ascFvN-Fc1k | scFv | GGGGSGGG SGGGGS | Hinge |
| 3a to 6 | ascFvc-Fc1k | CH3k | GGGGSGGGG SGGGGSGT | scFvCD3 |
| 3b to 6 | bscFvN-Fc1k | scFv | SG | Hinge w/o cysteines |
| 3b to 6 | bscFvc-Fc1k | CH3k | GGGGSGGGG SGGGGSGT | scFvCD3 |
| 9 | Fv-Fc1k-scFv | VH/VL | GTGGGSG | CH2 |
| 9 | Fv-Fc1k-scFv | CH31/CH3k | DKTHTAPAP PVAG | scFv |
| 10 to 12 | scFv-Fc1k | scFv (target) | AAA | Hinge-CH2-CH31 |

TABLE 5 -continued

Linker variants used in Examples 1-13.

| Example | Molecule | N-terminal domain | Linker Sequence | C-terminal domain |
|---|---|---|---|---|
| 10 to 12 | scFv-Fc1k | scFvCD3 | GGGGSGGGS GGGGS | Hinge-CH2-CH3k |
| 13 | scFvN-Fc1k | scFv (target) | AAA | Hinge-CH2-CH3l |
| 13 | scFvc-Fc1k | CH3k | GGGGSGGGG SGGGGSGT | scFvCD3 |

Subscript letters (N/C) indicate the position of the scFv relative to the Fc1k part (N-terminal/C-terminal).

Example 14: Further Characterization of Fv13.7x-Fc1k

The Fab-like monovalent molecule as described in example 8 was expressed in CHO cells from a cell pool after stable lentiviral transfection by Catalent Pharma Solutions (Somerset, Ewing, NJ, US). The protein was primarily purified using protein A and the monomeric fraction was further isolated by FPLC-SEC. The final preparation of Fv13.7x-Fc1k revealed a single peak in analytical HPLC-SEC (FIG. 35a), corresponding to the calculated molecular weight of 72 kDa. In SDS-PAGE under reducing conditions, two bands were observed, which migrated similar to the the 35 kDa and 40 kDa reference bands, corresponding well to the calculated molecular weights of the individual chains of 35 and 37 kDa. Under non-reducing conditions, the observed single band migrated similar to the 70 kDa reference band and thus indicated correct formation of the inter-chain disulfide bond. Fv13.7x-Fc1k revealed an aggregation temperature of 64° C. as determined by dynamic light scattering and visual interpretation of the detected mean count rates (FIG. 35c). Furthermore, Fv13.7x-Fc1k was stable in human plasma for at least seven days at 37° C. (FIG. 35d), indicated by retained binding activity as determined by huTNFR1-Fc binding ELISA.

Fv13.7x-Fc1k bound to human TNFR1-Fc with an EC50 value of 0.37 nM in ELISA (FIG. 36a), indicating reduced binding in comparison to the control proteins ATROSAB and Fab 13.7, which revealed EC50 values of 0.09 nM and 0.17 nM, respectively. In real-time binding analysis using the QCM (Attana, Stockholm, Sweden), Fv13.7x-Fc1k bound to human TNFRI-Fe with a $K_D$ value of 2.66 nM (FIG. 36b), resulting from a koff value of 9.83×10 4 s−1 as well as a kon value of 3.69×105 M-1s-1. Moreover, Fv13.7x-Fc1k carries modifications within the Fc proportion to reduce the propensity for the mediation of ADCP, ADCC and CDC (Armour et al. (1999) Eur J Immunol. 29(8):2613-24, Shields et al. (2001) J Biol Chem. 276(9):6591-604). Consistently, binding of human Fcγ receptors I, IIb and III as well as binding of human complement protein C1q to Fv13.7x-Fc1k was clearly reduced, when compared with the control antibody Retuximab, containing a wild-type Fc part (FIG. 36c). Similarly, FcγRI, IIb and III as well as C1q revealed reduced binding to the likewise mutated antibody ATROSAB, which revealed reduced mediation of ADCC and CDC in previously published experiments (Richter et al., (2013) PLoS One 8(8):e72156).

Similar to the monovalent control protein Fab 13.7, Fv13.7x-Fc1k did not show any signs of TNFR1 activation per se in IL-6 and IL-8 release experiments as well as in a cell death induction assay using HeLa. HT1080 and Kym-1 cells, respectively (FIG. 37a-c). This was in clear contrast to the control protein ATROSAB, which induced a marginal cellular response in IL-6 and IL-8 release experiments at concentrations between 1 and 100 nM (FIGS. 37a and b). Furthermore, Fv13.7x-Fc1k revealed potent inhibition of TNF-mediated TNFR1 activation in IL-6, IL-8 release and the cell death induction assays (FIG. 37d-f), with IC50 values of 54.5 nM, 24.2 nM and 16.2 nM, respectively. However, these values revealed a slightly weaker bioactivity as determined for Fab 13.7 with IC50 values of 31.7 nM, 12.7 nM, 9.5 nM in IL-6 and IL-8 release experiments and in the cell death induction assay, using HeLa and HT1080 as well as Kym-1 cells, respectively. Of note, the inhibitory activity of Fv13.7x-Fc1k was nevertheless clearly improved, when compared to the bivalent control protein ATROSAB, exhibiting IC50 vales of 164.7 nM, 84.1 nM as well as 64.4 nM in IL-6 and IL-8 release experiments and in the cell death induction assay.

TABLE 6

Bioactivity of Fv13.7x-Fc1k

| Experiment | Fv13.7x-Fc1k | Fab 13.7 | ATROSAB |
|---|---|---|---|
| $IC_{50}$, IL-6 [nM] | 54.5 | 37.1 | 164.7 |
| $IC_{50}$, IL-8 [nM] | 24.2 | 12.7 | 84.1 |
| $IC_{50}$, Cell death induction [nM] | 16.2 | 9.5 | 64.4 |

In order to further assess the bioactivity of Fv13.7x-Fc1k under conditions of antibody-mediated crosslinking, Fv13.7x-Fc1k was analyzed in IL-8 release experiments in the presence of a constant concentration of drug-specific antibodies (FIG. 38a-c). In contrast to the control antibody ATROSAB, Fv13.7x-Fc1k as well as the corresponding Fab 13.7 revealed a complete lack of agonistic activity in IL-8 release assays using three different goat anti-human IgG serum preparations (FIG. 38a: SouthernBiotech Cat.: 2010-01 [IgG_A], FIG. 38b: MyBioSource Cat.: MBS571163 [IgG_B], FIG. 38c: MyBioSource Cat.: MBS571678 [IgG C]). Conclusively, this result could indicate a reduced risk of Fv13.7x-Fc1k to activate TNFR1 in vivo under conditions of an anti-drug immune response.

Finally, Fv13.7x-Fc1k revealed initial and terminal half-lifes of 2.2±1.2 h and 41.8±18.1 h, respectively, and an area under the curve of 5856±1370 μg/ml*h, after single-dose injection of 400 μg (20 mg/kg) in C56BL/6J knock-in mice, carrying the gene of the extracellular domain of human TNFR1 at the respective mouse locus.

Materials

Horseradish peroxidase (HRP)-conjugated anti-human IgG (Fab specific) antibodies were purchased from Sigma (Taufkirchen, Germany). HT1080 wt cells were grown RPMI 1640 medium, 5% FCS, 2 mM L-glutamine. ATROSAB and human TNFR1-Fc fusion was provided by Baliopharm AG (Basel, Switzerland). Chemicals were purchased from Roth (Karlsruhe, Germany) while enzymes (cloning and PCR) and supplemental reagents were purchased from ThermoFisher (Munich, Germany). Any different source of consumables is clearly stated below.

Methods

Alignment of Heterodimerizing and Functional Ig and Ig-Like Domains

1) Multiple sequence alignment was performed using the Clustal omega online tool.
2) Definitions of beat sheets in pdb files were highlighted in the sequences 3) If no or not all secondary structure beta sheets were assigned (indicated with star in FIG. 4) prediction of secondary structures according to JPred (longest cumulated prediction using default settings) was performed.

4) Start and end positions of beta sheets A-G were aligned according to additional structural alignment of PDB files upon inclusion of formally not assigned residues into the sheets or the exclusion of formerly assigned residues from sheets as well as the deletion of gaps introduced by multiple sequence alignment or, in 4 exceptions by the insertion of novel gaps outside of the beta sheets (d_CH3: IgLCRC position 111; m_CH1: IgLCRC position 72; HLAA/HLAB: IgLCRC position 60, FIG. 4). Inserted/elongated or deleted/curtailed gap positions were compensated for by deletion or insertion of gap positions in the following already existing gap, introduced during multiple sequence alignment, respectively, in order to maintain the alignment of the sequences in regions located closer to the c-terminus.

5) Beta sheet A was defined by these means as the six residues subsequent to a conserved proline residue N-terminal to the predicted first beta sheet (IgLCRC positions 13-18).

6) Beta sheet B was defined as the four residues N-terminally and the five residues C-terminally neighboring a conserved cysteine residue included in the second predicted beta sheet (IgLCRC positions 31-40).

7) Beta sheet C was defined as the four residues N-terminally and the two residues C-terminally neighboring a conserved tryptophan residue included in the third predicted beta sheet (IgLCRC positions 46-52). Exceptions were TCR alpha chain and beta 2 microglobulin. In these cases the alignment was performed due to beta sheet prediction and confirmed upon structural alignment using pyMol, 8) Beta sheet D was defined from IgLCRC position 63-70, however, connection to a conserved residue throughout the whole alignment was not feasible.

9) Beta sheet E was defined as the eight residues from IgLCRC position 81-89, starting with a conserved Tyrosine/Phenylalanine residue, located to the beginning or N-terminally to fourth predicted beta sheet.

10) Beta sheet F was defined as the two residues N-terminally and the four residues C-terminally neighboring a conserved cysteine residue included in the sixth predicted beta sheet (IgLCRC positions 102-108).

11) Beta sheet G was defined from IgLCRC position 128-133, however, connection to a conserved residue throughout the whole alignment was not feasible.

Expression of Fab13.7, Fv13.7-Fc1k, scFv13.7-Fc1k, scFv13.7-Fc

HEK293-6E cells were cultivated in suspension under conditions of exponential growth in FreeStyle F17 medium, containing 4 mM GlutaMAX-I and 0.1% Kolliphor P188 (F17). $1.5*10^6$ cells/ml were prepared for transfection using 1 µg/ml plasmid DNA (final concentration) and 3 µg/ml Polyethylenimin (PEI, final concentration). DNA and PEI were each diluted in 1 ml F17$^{++}$ medium per 20 ml cell suspension and subsequently mixed together. After 15-30 min incubation at RT the DNA mixture was added to the cells and incubated shaking over night at 37° C. and 5% $CO_2$. 24 h later, 0.5 ml Trypton N1 was added per 20 ml cell suspension. Protein was purified from the supernatant after additional 4 days of incubation at 37° C. and 5% $CO_2$.

Protein Purification—Antibody and Protein a Affinity Chromatography

HEK293-6E cells were removed from culture supernatants by centrifugation (Step 1: 500 g, 15 min; step2: 5000 g, 5 min). Supernatants were incubated with either TOYO-PEARL® AFrProtein A-650F (protein A resin, 22805, Tosoh, Stuttgart, Germany) or HiTrap KappaSelect (kappa chain selective antibody fragments conjugated to a agarose matrix, 17-5458-12, GE Healthcare, Chalfont St Giles, GB) resins rolling over night. Resins were collected by centrifugation and loaded onto Poly-Prep® chromatography column by gravity flow. Washing was performed using PBS and proteins were eluted from the resin with 100 mM glycine at pH 2-3. Eluted fractions were directly pooled and immediately dialyzed against PBS.

Preparative Size Exclusion Chromatography

In the case of aggregated or multimeric assembled protein in the preparations, an additional size exclusion step was performed using the Äkta purifier. Proteins were separated on a Superdex 200 10/300 GL column at a flow rate of 0.5 ml/min using PBS as liquid phase. Fractions of 200 µl were collected and the peak containing samples were pooled for further experiments.

Protein Characterization—Poly-Acrylamide Gel Electrophoresis (SDS-PAGE)

SDS-PAGE was performed strictly according to Laemmli 1970, using 3 µg of protein preparations and the indicated percentages of stacking and separation gel.

Protein Characterization—Size Exclusion Chromatography (SEC)

To determine the hydrodynamic radius, 30 µg purified protein samples were analyzed using the Waters 2695 HPLC in combination with a Phenomenex Yarra SEC-2000 column (300×7.8 mm, flow rate of 0.5 ml/min). The mobile phase was 0.1 M Na2HPO4/NaH2PO4, 0.1 M Na2SO4, pH 6.7. The following standard proteins were used: Thyroglobulin (669 kDa), Apoferritin (443 kDa), Alcohol dehydrogenase (150 kDa), BSA (66 kDa), Carbonic anhydrase (29 kDa), FLAG peptide (1 kDa).

Enzyme-Linked Immunosorbent Assay (ELISA)

Microtiter plates were coated with 100 µl of TNFFR1-Fc fusion protein (1 µg/ml in PBS) and incubated at 4° C. overnight. The residual binding sites were blocked with 2% MPBS (skim milk in PBS, 200 µl per well) at room temperature for 2 hours and subsequently washed twice with PBS. 100 µl of the samples diluted in 2% MPBS were incubated at room temperature for 1 hour prior to the last incubation step with 100 µl of the HRP conjugated detection antibodies in 2% MPBS. Bound protein was detected with 100 µl TMB substrate solution, the HRP-reaction was stopped by the addition of 50 µl 1 M H2SO4 and the absorption at the wavelength of 450 nm was measured using the Infinite microtiter plate reader (TECAN, Maennedorf, Switzerland). Between each incubation step and in advance of the detection, the plates were washed three times with PBST and twice with PBS.

Flow Cytometry

Cells were detached and transferred to a 96 well microtiter plate at a concentration of 100.000-250.000 per well in 100 µl PBA (2% FCS, 0.2% NaN3 in sterile PBS). Samples were diluted in PBA at a double to the finally desired concentration and 100 µl were added to the cells for a 1 hour incubation. Subsequently, the cells were incubated with antibodies conjugated to fluorescent dyes prior to the detection using the MACSQuant® Analyzer (Miltenyi Biotec, Bergisch Gladbach, Germany). Cells were washed twice by centrifugation (500*g, 5 minutes) and resuspension in 150 µl PBA after each incubation step.

Interleukin Release Assay $2\times10^4$ HeLa or HT1080 cells per well were seeded into a 96 well microtiter plate and grown in 100 µl RPMI 1640+5% FCS overnight. The next day, the supernatants were exchanged in order to remove constitutively produced cytokines. The cells were incubated with dilution series of samples in RPMI 1640+5% FCS at 37° C., 5% $CO_2$. In the case of competition experiments, both analyzed protein samples were prepared individually (either titrated or diluted to a single concentration) and added to the plate subsequently. Non-stimulated cells served as control. After 16-20 hours, the plates were centrifuged at 500 g for 5 minutes and cell supernatants were analyzed directly by ELISA, which was performed according to the protocol of the manufacturer. Supernatants were diluted in RPMI 1640 (without FCS) and antibodies were diluted in Reagent Diluent (0.1% BSA, 0.05% Tween 20, 20 mM TRIS, 150 mM NaCl, pH7.5). The coated microtiter plates were blocked using 1% BSA (Bovine Serum Albumin) in PBS and washing as well as detection and measuring were performed as described above for ELISA. Sandwich ELISA kits for the detection of IL-6 and IL-8 in the cell culture supernatant were purchased from ImmunoTools, (Friesoythe, Germany).

Cytotoxicity/Cell viability Assay

Cells ($2*10^4$ per well) were seeded into 96-well microtiter plates and incubated over night at 37° C. and 5% C02. The proteins were diluted in RPMI 1640+10% FCS and added to the cells in combination with $2*10^5$ PBMCs/well. Cytotoxicity assays were incubated at 37° C., 5% C02 for 3 to 5 days before the supernatant was discarded and 50 µl crystal violet solution was added to the cells. Subsequently, the plates were washed in ddH2O for 20 times and dried. The remaining violet dye, resulting from living and adherent cells, which were fixed by the methanol contained in the staining solution, was dissolved by the addition of 100 µl methanol upon shaking at RT for 10 minutes. Plates were measured using the Infinite microtiterplate reader (Tecan, Maennedorf, Switzerland).

Pharmacokinetics

Transgenic C57BL/6J mice, bearing the gene of the extracellular domain of human TNFR-1 at the locus of the particular mouse gene (C57BL/6J-huTNFRSF1Aecdtm1UEG/izi), were injected intravenously with 25 µg of the analyzed proteins. Blood samples were collected after 3 min, 30 min, 1 h, 3 h and 6 h as well as after 3 days and 7 days and incubated on ice immediately. Serum was separated by centrifugation (13.000 g, 4° C., 10 minutes) and stored at −20° C. Remaining protein in the serum was detected by binding ELISA as described above. The ELISA signal was interpolated from a freshly prepared standard binding curve of the analyzed protein. Determined concentrations were plotted against time and pharmacokinetic constants were obtained upon analysis using PKsolver add-in for Microsoft Excel.

The invention claimed is:

1. A protein complex comprising at least two amino acid chains I and II, which are non-covalently bound to each other through a heterodimerization region I (HRI) comprised in amino acid chain I and a heterodimerization region II (HRII) comprised in amino acid chain II, wherein HRI and HRII have the amino acid sequence according to SEQ ID NO: 20 and 21 respectively, or a heterodimerizing variant thereof having at least 97.5% sequence identity to the respectively indicated amino acid sequence.

2. The protein complex of claim 1, wherein the amino acid chain I and/or the amino acid chain II further comprise one or more amino acid elements selected from the group consisting of a CH2 or CH3 domain of an antibody; one or more antigen specific ligand (ASL), selected from the group consisting of a Fv, a single-chain Fv (scFv), a disulfide-stabilized Fv, a disulfide-stabilized scFv, a Fab, a single-chain Fab, a single domain antibody, a variable heavy chain domain (VH), a variable light chain domain (VL), T-cell receptor or antigen binding fragments thereof, a VHH, one or more antibody-like binding proteins; an antibody hinge region (HR), one or more linker sequences (L), one or more cytokine, interleukine, interferon, growth factor, hormone, ligand, receptor fragment with ligand-binding activity, chelator, enzyme, coagulation factor, and anti-coagulant, wherein the amino acid chain I comprises one or more antigen specific ligands (ASL) and/or one or more effector molecules and the amino acid chain II comprises one or more antigen specific ligands (ASL) and/or one or more effector molecules and, wherein the one or more ASL are selected from the group consisting of molecules that specifically bind to cell surface protein, hormone, growth factor, cytokine, ligand, serum protein, coagulation factor, fibrinolytic factor, chemokine, and enzyme,
wherein the one or more effector molecules are selected from the group consisting of cell surface protein, hormone, growth factor, cytokine, ligand, serum protein, coagulation factor, fibrinolytic factor, chemokine, and enzyme.

3. The protein complex of claim 1, wherein the amino acid chain I and the amino acid chain II comprises the amino acid sequence according to SEQ ID NO: 41 and SEQ ID NO: 42, SEQ ID NO: 34 and SEQ ID NO: 35, SEQ ID NO: 43 and SEQ ID NO: 44, SEQ ID NO: 36 and SEQ ID NO: 37 (scFv13.7-Fclk), SEQ ID NO: 36 and SEQ ID NO: 38 (scFv13.7-CD3-Hinge-Fclk), SEQ ID NO: 39 and SEQ ID NO: 38 (scFv3-43-CD3-Hinge-Fclk) or SEQ ID NO: 40 and SEQ ID NO: 38 (scFvhuMCSP-CD3-Hinge-Fclk).

4. The protein complex of claim 1, wherein the amino acid chain I and the amino acid chain II consist of the amino acid sequence according to SEQ ID NO: 41 and SEQ ID NO: 42.

5. A nucleic acid encoding the amino acid chain I and/or II of claim 3.

6. A vector comprising any one of the nucleic acids of claim 5.

* * * * *

SEQUENCE LISTING

```
<160> NUMBER OF SEQ ID NOS: 59

<210> SEQ ID NO 1
<211> LENGTH: 103
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 2
<211> LENGTH: 101
<212> TYPE: PRT
<213> ORGANISM: Homo sapiens

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys
            100

<210> SEQ ID NO 3
<211> LENGTH: 103
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro
            100

<210> SEQ ID NO 4
<211> LENGTH: 103
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly
            100

<210> SEQ ID NO 5
<211> LENGTH: 101
<212> TYPE: PRT
<213> ORGANISM: Homo sapiens

<400> SEQUENCE: 5

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys
            100

<210> SEQ ID NO 6
<211> LENGTH: 101
<212> TYPE: PRT
<213> ORGANISM: Homo sapiens

<400> SEQUENCE: 6

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys
            100

<210> SEQ ID NO 7
<211> LENGTH: 104
<212> TYPE: PRT
<213> ORGANISM: Homo sapiens

<400> SEQUENCE: 7

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro
            100

<210> SEQ ID NO 8
<211> LENGTH: 105
<212> TYPE: PRT
<213> ORGANISM: Hmo sapiens

<400> SEQUENCE: 8

Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Trp Asp Thr Gly Ser Leu
        35                  40                  45

Asn Gly Thr Thr Met Thr Leu Pro Ala Thr Thr Leu Thr Leu Ser Gly
    50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
                85                  90                  95

Val Asp Asn Lys Thr Phe Ser Val Cys
            100                 105

<210> SEQ ID NO 9
<211> LENGTH: 106
<212> TYPE: PRT
<213> ORGANISM: Homo sapiens

<400> SEQUENCE: 9

Gly Ser Ala Ser Ala Pro Thr Leu Phe Pro Leu Val Ser Cys Glu Asn
1               5                   10                  15

Ser Ser Pro Ser Ser Thr Val Ala Val Gly Cys Leu Ala Gln Asp Phe
            20                  25                  30

Leu Pro Asp Ser Ile Thr Phe Ser Trp Lys Tyr Lys Asn Asn Ser Asp
        35                  40                  45

Ile Ser Ser Thr Arg Gly Phe Pro Ser Val Leu Arg Gly Gly Lys Tyr
    50                  55                  60

Ala Ala Thr Ser Gln Val Leu Leu Pro Ser Lys Asp Val Met Gln Gly
65                  70                  75                  80

Thr Asp Glu His Val Val Cys Lys Val Gln His Pro Asn Gly Asn Lys
                85                  90                  95

Glu Lys Asp Val Pro Leu Pro Val Ile
            100                 105

<210> SEQ ID NO 10
<211> LENGTH: 97
<212> TYPE: PRT
<213> ORGANISM: Homo sapiens

<400> SEQUENCE: 10

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn

```
              65                  70                  75                  80
Ser Ile Ile Pro Glu Asp Thr Phe Phe Pro Ser Pro Glu Ser Ser Cys
                85                  90                  95

Asp

<210> SEQ ID NO 11
<211> LENGTH: 130
<212> TYPE: PRT
<213> ORGANISM: Homo sapiens

<400> SEQUENCE: 11

Asp Leu Lys Asn Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Tyr Pro Asp His Val Glu Leu Ser Trp Trp Val Asn Gly
        35                  40                  45

Lys Glu Val His Ser Gly Val Ser Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys
    130

<210> SEQ ID NO 12
<211> LENGTH: 98
<212> TYPE: PRT
<213> ORGANISM: Homo sapiens

<400> SEQUENCE: 12

Gly Lys Gly Asn Leu Glu Trp Lys Glu Pro Pro Ser Met Arg Leu Lys
1               5                   10                  15

Ala Arg Pro Ser Ser Pro Gly Phe Ser Val Leu Thr Cys Ser Ala Phe
            20                  25                  30

Ser Phe Tyr Pro Pro Glu Leu Gln Leu Arg Phe Leu Arg Asn Gly Leu
        35                  40                  45

Ala Ala Gly Thr Gly Gln Gly Asp Phe Gly Pro Asn Ser Asp Gly Ser
    50                  55                  60

Phe His Ala Ser Ser Ser Leu Thr Val Lys Ser Gly Asp Glu His His
65                  70                  75                  80

Tyr Cys Cys Ile Val Gln His Ala Gly Leu Ala Gln Pro Leu Arg Val
                85                  90                  95

Glu Leu

<210> SEQ ID NO 13
<211> LENGTH: 99
<212> TYPE: PRT
<213> ORGANISM: Homo sapiens

<400> SEQUENCE: 13

Ile Gln Arg Thr Pro Lys Ile Gln Val Tyr Ser Arg His Pro Ala Glu
```

```
                1               5                   10                  15
            Asn Gly Lys Ser Asn Phe Leu Asn Cys Tyr Val Ser Gly Phe His Pro
                            20                  25                  30

Ser Asp Ile Glu Val Asp Leu Leu Lys Asn Gly Glu Arg Ile Glu Lys
                            35                  40                  45

Val Glu His Ser Asp Leu Ser Phe Ser Lys Asp Trp Ser Phe Tyr Leu
                50                  55                  60

Leu Tyr Tyr Thr Glu Phe Thr Pro Thr Glu Lys Asp Glu Tyr Ala Cys
            65                  70                  75                  80

Arg Val Asn His Val Thr Leu Ser Gln Pro Lys Ile Val Lys Trp Asp
                            85                  90                  95

Arg Asp Met
```

```
<210> SEQ ID NO 14
<211> LENGTH: 101
<212> TYPE: PRT
<213> ORGANISM: Homo sapiens

<400> SEQUENCE: 14

Gly Lys Glu Thr Leu Gln Arg Thr Asp Ala Pro Lys Thr His Met Thr
1               5                   10                  15

His His Ala Val Ser Asp His Glu Ala Thr Leu Arg Cys Trp Ala Leu
                20                  25                  30

Ser Phe Tyr Pro Ala Glu Ile Thr Leu Thr Trp Gln Arg Asp Gly Glu
            35                  40                  45

Asp Gln Thr Gln Asp Thr Glu Leu Val Glu Thr Arg Pro Ala Gly Asp
        50                  55                  60

Gly Thr Phe Gln Lys Trp Ala Ala Val Val Val Pro Ser Gly Gln Glu
65                  70                  75                  80

Gln Arg Tyr Thr Cys His Val Gln His Glu Gly Leu Pro Lys Pro Leu
                85                  90                  95

Thr Leu Arg Trp Glu
            100
```

```
<210> SEQ ID NO 15
<211> LENGTH: 102
<212> TYPE: PRT
<213> ORGANISM: Homo sapiens

<400> SEQUENCE: 15

Asp Ile Glu Thr Leu Gln Arg Ala Asp Pro Pro Lys Thr His Val Thr
1               5                   10                  15

His His Pro Ile Ser Asp His Glu Ala Thr Leu Arg Cys Trp Ala Leu
                20                  25                  30

Gly Phe Tyr Pro Ala Glu Ile Thr Leu Thr Trp Gln Arg Asp Gly Glu
            35                  40                  45

Asp Gln Thr Gln Asp Thr Glu Leu Val Glu Thr Arg Pro Ala Gly Asp
        50                  55                  60

Arg Thr Phe Gln Lys Trp Ala Ala Val Val Val Pro Ser Gly Glu Glu
65                  70                  75                  80

Gln Arg Tyr Thr Cys His Val Gln His Glu Gly Leu Pro Lys Pro Leu
                85                  90                  95

Thr Leu Arg Trp Glu Pro
            100
```

<210> SEQ ID NO 16

```
<211> LENGTH: 106
<212> TYPE: PRT
<213> ORGANISM: Homo sapiens

<400> SEQUENCE: 16

Gly Arg Ile Pro Val Ser Arg Gly Phe Pro Ile Ala Glu Val Phe Thr
1               5                   10                  15

Leu Lys Pro Leu Glu Phe Gly Lys Pro Asn Thr Leu Val Cys Phe Val
            20                  25                  30

Ser Asn Leu Phe Pro Pro Met Leu Thr Val Asn Trp His Asp His Ser
        35                  40                  45

Val Pro Val Glu Gly Phe Gly Pro Thr Phe Val Ser Ala Val Asp Gly
    50                  55                  60

Leu Ser Phe Gln Ala Phe Ser Tyr Leu Asn Phe Thr Pro Glu Pro Ser
65                  70                  75                  80

Asp Ile Phe Ser Cys Ile Val His Glu Pro Asp Arg Tyr Thr Ala
                85                  90                  95

Ile Ala Tyr Trp Val Pro Arg Asn Ala Leu
            100                 105

<210> SEQ ID NO 17
<211> LENGTH: 108
<212> TYPE: PRT
<213> ORGANISM: Homo sapiens

<400> SEQUENCE: 17

Trp Gly Ser Leu Thr Asn Arg Thr Arg Pro Ser Val Gln Val Ala
1               5                   10                  15

Lys Thr Thr Pro Phe Asn Thr Arg Glu Pro Val Met Leu Ala Cys Tyr
            20                  25                  30

Val Trp Gly Phe Tyr Pro Ala Glu Val Thr Ile Thr Trp Arg Lys Asn
        35                  40                  45

Gly Lys Leu Val Met His Ser Ser Ala His Lys Thr Ala Gln Pro Asn
    50                  55                  60

Gly Asp Trp Thr Tyr Gln Thr Leu Ser His Leu Ala Leu Thr Pro Ser
65                  70                  75                  80

Tyr Gly Asp Thr Tyr Thr Cys Val Val Glu His Ile Gly Ala Pro Glu
                85                  90                  95

Pro Ile Leu Arg Asp Trp Thr Pro Gly Leu Ser Pro
            100                 105

<210> SEQ ID NO 18
<211> LENGTH: 106
<212> TYPE: PRT
<213> ORGANISM: Homo sapiens

<400> SEQUENCE: 18

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80
```

```
His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 19
<211> LENGTH: 106
<212> TYPE: PRT
<213> ORGANISM: Homo sapiens

<400> SEQUENCE: 19

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 20
<211> LENGTH: 104
<212> TYPE: PRT
<213> ORGANISM: Homo sapiens

<400> SEQUENCE: 20

Gly Gln Pro Arg Glu Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Ser Asp Ile Ala Val Glu Trp Glu Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ser Cys Ser Val Met His Glu Ala Leu His Asn His Tyr Thr Gln
                85                  90                  95

Lys Ser Val Glu Pro Lys Ser Cys
            100

<210> SEQ ID NO 21
<211> LENGTH: 108
<212> TYPE: PRT
<213> ORGANISM: Homo sapiens

<400> SEQUENCE: 21

Gly Gln Pro Arg Glu Pro Ser Val Phe Ile Phe Pro Pro Ser Asp Glu
1               5                   10                  15

Gln Leu Lys Ser Gly Thr Ala Ser Val Val Cys Leu Val Asn Asn Phe
            20                  25                  30

Tyr Pro Arg Asp Ile Ala Val Glu Trp Glu Val Asp Asn Ala Leu Gln
```

```
            35                  40                  45
Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ser Cys Ser Val Met His Glu Ala Leu His Asn
                     85                  90                  95

His Tyr Thr Gln Lys Ser Phe Asn Arg Gly Glu Cys
                100                 105

<210> SEQ ID NO 22
<211> LENGTH: 104
<212> TYPE: PRT
<213> ORGANISM: Homo sapiens

<400> SEQUENCE: 22

Gly Gln Pro Arg Glu Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Tyr Pro Ser Asp Val Ala Val Glu Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Met His Glu Ala Leu His Asn His Lys Val Asp
                 85                  90                  95

Lys Lys Val Glu Pro Lys Ser Cys
                100

<210> SEQ ID NO 23
<211> LENGTH: 108
<212> TYPE: PRT
<213> ORGANISM: Homo sapiens

<400> SEQUENCE: 23

Gly Gln Pro Arg Glu Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
                20                  25                  30

Tyr Pro Ser Asp Ala Ala Val Glu Trp Lys Val Asp Asn Ala Leu Gln
            35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Met His Glu Ala Leu His Asn
                 85                  90                  95

His Pro Val Thr Lys Ser Phe Asn Arg Gly Glu Cys
                100                 105

<210> SEQ ID NO 24
<211> LENGTH: 101
<212> TYPE: PRT
<213> ORGANISM: Homo sapiens

<400> SEQUENCE: 24
```

Gly Gln Pro Arg Glu Pro Lys Ile Gln Val Tyr Ser Arg His Pro Ala
1               5                   10                  15

Glu Asn Gly Lys Ser Asn Phe Leu Asn Cys Tyr Val Ser Gly Phe Tyr
            20                  25                  30

Pro Ser Asp Ile Ala Val Glu Leu Leu Lys Asn Gly Glu Arg Ile Glu
        35                  40                  45

Lys Val Glu His Ser Asp Leu Ser Phe Ser Lys Asp Trp Ser Phe Tyr
50                  55                  60

Leu Leu Tyr Tyr Thr Glu Phe Thr Pro Thr Glu Lys Asp Glu Tyr Ala
65                  70                  75                  80

Cys Arg Val Met His Glu Ala Leu His Asn His Pro Lys Ile Val Lys
                85                  90                  95

Trp Asp Arg Asp Met
            100

<210> SEQ ID NO 25
<211> LENGTH: 94
<212> TYPE: PRT
<213> ORGANISM: Homo sapiens

<400> SEQUENCE: 25

Gly Gln Pro Arg Glu Pro Ser Met Arg Leu Lys Ala Arg Pro Ser Ser
1               5                   10                  15

Pro Gly Phe Ser Val Leu Thr Cys Ser Ala Phe Ser Phe Tyr Pro Ser
            20                  25                  30

Asp Leu Ala Leu Glu Phe Leu Arg Asn Gly Leu Ala Ala Gly Thr Gly
        35                  40                  45

Gln Gly Asp Phe Gly Pro Asn Ser Asp Gly Ser Phe His Ala Ser Ser
50                  55                  60

Ser Leu Thr Val Lys Ser Gly Asp Glu His His Tyr Cys Cys Ile Val
65                  70                  75                  80

Met His Glu Ala Leu His Asn His Pro Leu Arg Val Glu Leu
                85                  90

<210> SEQ ID NO 26
<211> LENGTH: 97
<212> TYPE: PRT
<213> ORGANISM: Homo sapiens

<400> SEQUENCE: 26

Gly Gln Pro Arg Glu Pro Asp Pro Ala Val Tyr Gln Leu Arg Asp Ser
1               5                   10                  15

Lys Ser Ser Asp Lys Ser Val Cys Leu Phe Thr Asp Phe Tyr Pro Ser
            20                  25                  30

Asp Val Ala Gln Glu Lys Asp Ser Asp Val Tyr Ile Thr Asp Lys Thr
        35                  40                  45

Val Leu Asp Met Arg Ser Met Asp Phe Lys Ser Asn Ser Ala Val Ala
50                  55                  60

Trp Ser Asn Lys Ser Asp Phe Ala Cys Ala Asn Met Phe Glu Ala Leu
65                  70                  75                  80

His Asn His Ile Pro Glu Asp Thr Phe Phe Pro Ser Pro Glu Ser Ser
                85                  90                  95

Cys

<210> SEQ ID NO 27
<211> LENGTH: 115

```
<212> TYPE: PRT
<213> ORGANISM: Homo sapiens

<400> SEQUENCE: 27

Gly Gln Pro Arg Glu Pro Glu Val Ala Val Phe Pro Ser Glu Ala
1               5                   10                  15

Glu Ile Ser His Thr Gln Lys Ala Thr Leu Val Cys Leu Ala Thr Gly
                20                  25                  30

Phe Tyr Pro Ser Asp Val Ala Leu Glu Trp Trp Val Asn Gly Lys Glu
            35                  40                  45

Val His Ser Gly Val Ser Thr Asp Pro Gln Pro Leu Lys Glu Gln Pro
        50                  55                  60

Ala Leu Asn Asp Ser Arg Tyr Cys Leu Ser Ser Arg Leu Arg Val Ser
65                  70                  75                  80

Ala Thr Phe Trp Gln Asn Pro Arg Asn His Phe Arg Cys Gln Val Met
                85                  90                  95

Phe Glu Ala Leu His Asn His Ile Val Ser Ala Glu Ala Trp Gly Arg
                100                 105                 110

Ala Asp Cys
        115

<210> SEQ ID NO 28
<211> LENGTH: 97
<212> TYPE: PRT
<213> ORGANISM: Homo sapiens

<400> SEQUENCE: 28

Ala Ser Thr Lys Gly Pro Asp Pro Ala Val Tyr Gln Leu Arg Asp Ser
1               5                   10                  15

Lys Ser Ser Asp Lys Ser Val Cys Leu Phe Thr Asp Phe Phe Pro Glu
                20                  25                  30

Pro Val Ser Gln Ser Lys Asp Ser Asp Val Tyr Ile Thr Asp Lys Thr
            35                  40                  45

Val Leu Asp Met Arg Ser Met Asp Tyr Lys Ser Asn Ser Ala Val Ala
        50                  55                  60

Trp Ser Asn Lys Ser Asp Phe Ala Cys Ala Asn Ala Phe Lys Pro Ser
65                  70                  75                  80

Asn Thr Ile Pro Glu Asp Thr Phe Phe Pro Ser Pro Glu Ser Ser Cys
                85                  90                  95

Asp

<210> SEQ ID NO 29
<211> LENGTH: 96
<212> TYPE: PRT
<213> ORGANISM: Homo sapiens

<400> SEQUENCE: 29

Thr Val Ala Ala Pro Asp Pro Ala Val Tyr Gln Leu Arg Asp Ser Lys
1               5                   10                  15

Ser Ser Asp Lys Ser Val Cys Leu Phe Thr Asp Phe Tyr Pro Arg Glu
                20                  25                  30

Val Ser Gln Ser Lys Asp Ser Asp Val Tyr Ile Thr Asp Lys Thr Val
            35                  40                  45

Leu Asp Met Arg Ser Met Asp Tyr Lys Ser Asn Ser Ala Val Ala Trp
        50                  55                  60

Ser Asn Lys Ser Asp Phe Ala Cys Ala Asn Ala Phe Gln Gly Leu Ser
65                  70                  75                  80
```

Ser Ile Pro Glu Asp Thr Phe Phe Pro Ser Pro Glu Ser Ser Cys Asp
             85                  90                  95

<210> SEQ ID NO 30
<211> LENGTH: 96
<212> TYPE: PRT
<213> ORGANISM: Homo sapiens

<400> SEQUENCE: 30

Gly Gln Pro Lys Ala Asn Pro Asp Pro Ala Val Tyr Gln Leu Arg Asp
1               5                   10                  15

Ser Lys Ser Ser Asp Lys Ser Val Cys Leu Phe Thr Asp Phe Tyr Pro
            20                  25                  30

Gly Ala Val Ser Gln Ser Lys Asp Ser Asp Val Tyr Ile Thr Asp Lys
        35                  40                  45

Thr Val Leu Asp Met Arg Ser Met Asp Tyr Lys Ser Asn Ser Ala Val
    50                  55                  60

Ala Trp Ser Asn Lys Ser Asp Phe Ala Cys Ala Asn Ala Phe Glu Gly
65                  70                  75                  80

Ser Ile Pro Glu Asp Thr Phe Phe Pro Ser Pro Glu Ser Ser Cys Asp
             85                  90                  95

<210> SEQ ID NO 31
<211> LENGTH: 114
<212> TYPE: PRT
<213> ORGANISM: Homo sapiens

<400> SEQUENCE: 31

Ala Ser Thr Lys Gly Pro Glu Val Ala Val Phe Glu Pro Ser Glu Ala
1               5                   10                  15

Glu Ile Ser His Thr Gln Lys Ala Thr Leu Val Cys Leu Ala Thr Gly
            20                  25                  30

Phe Phe Pro Glu Pro Val Glu Leu Ser Trp Trp Val Asn Gly Lys Glu
        35                  40                  45

Val His Ser Gly Val Ser Thr Asp Pro Gln Pro Leu Lys Glu Gln Pro
    50                  55                  60

Ala Leu Asn Asp Ser Arg Tyr Cys Leu Ser Ser Arg Leu Arg Val Ser
65                  70                  75                  80

Ala Thr Phe Trp Gln Asn Pro Arg Asn His Phe Arg Cys Gln Val Gln
            85                  90                  95

Phe Lys Pro Ser Asn Thr Ile Val Ser Ala Glu Ala Trp Gly Arg Ala
            100                 105                 110

Asp Cys

<210> SEQ ID NO 32
<211> LENGTH: 113
<212> TYPE: PRT
<213> ORGANISM: Homo sapiens

<400> SEQUENCE: 32

Thr Val Ala Ala Pro Glu Val Ala Val Phe Glu Pro Ser Glu Ala Glu
1               5                   10                  15

Ile Ser His Thr Gln Lys Ala Thr Leu Val Cys Leu Ala Thr Gly Phe
            20                  25                  30

Tyr Pro Arg Glu Val Glu Leu Ser Trp Trp Val Asn Gly Lys Glu Val
        35                  40                  45

His Ser Gly Val Ser Thr Asp Pro Gln Pro Leu Lys Glu Gln Pro Ala

```
                    50                  55                  60
Leu Asn Asp Ser Arg Tyr Cys Leu Ser Ser Arg Leu Arg Val Ser Ala
 65                  70                  75                  80

Thr Phe Trp Gln Asn Pro Arg Asn His Phe Arg Cys Gln Val Gln Phe
                     85                  90                  95

Gln Gly Leu Ser Ser Ile Val Ser Ala Glu Ala Trp Gly Arg Ala Asp
                    100                 105                 110

Cys

<210> SEQ ID NO 33
<211> LENGTH: 113
<212> TYPE: PRT
<213> ORGANISM: Homo sapiens

<400> SEQUENCE: 33

Gly Gln Pro Lys Ala Asn Pro Glu Val Ala Val Phe Glu Pro Ser Glu
  1                   5                  10                  15

Ala Glu Ile Ser His Thr Gln Lys Ala Thr Leu Val Cys Leu Ala Thr
                     20                  25                  30

Gly Phe Tyr Pro Gly Ala Val Glu Leu Ser Trp Trp Val Asn Gly Lys
                 35                  40                  45

Glu Val His Ser Gly Val Ser Thr Asp Pro Gln Pro Leu Lys Glu Gln
             50                  55                  60

Pro Ala Leu Asn Asp Ser Arg Tyr Cys Leu Ser Arg Leu Arg Val
 65                  70                  75                  80

Ser Ala Thr Phe Trp Gln Asn Pro Arg Asn His Phe Arg Cys Gln Val
                     85                  90                  95

Gln Phe Glu Gly Ser Ile Val Ser Ala Glu Ala Trp Gly Arg Ala Asp
                    100                 105                 110

Cys

<210> SEQ ID NO 34
<211> LENGTH: 329
<212> TYPE: PRT
<213> ORGANISM: Homo sapiens

<400> SEQUENCE: 34

His Val Gln Leu Val Gln Ser Gly Ala Glu Val Lys Lys Pro Gly Ser
  1                   5                  10                  15

Ser Val Lys Val Ser Cys Lys Ala Ser Gly Tyr Thr Phe Thr Asp Phe
                     20                  25                  30

Tyr Ile Asn Trp Val Arg Gln Ala Pro Gly Gln Gly Leu Glu Trp Ile
                 35                  40                  45

Gly Glu Ile Val Pro Ser Gln Gly Glu Ala Lys Tyr Asn Asp Lys Phe
             50                  55                  60

Lys Ala Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                     85                  90                  95

Ala Arg Trp Asp Phe Leu Asp Tyr Trp Gly Gln Gly Thr Thr Val Thr
                    100                 105                 110

Val Ser Ser Gly Thr Gly Gly Ser Gly Pro Ser Val Phe Leu Phe
             115                 120                 125

Pro Pro Lys Pro Lys Asp Thr Leu Met Ile Ser Arg Thr Pro Glu Val
            130                 135                 140
```

```
Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Gly Leu Pro Ser Ser Ile Glu Lys Thr Ile Ser Lys Ala
    210                 215                 220

Lys Gly Gln Pro Arg Glu Pro Ser Val Phe Pro Leu Ala Pro Ser Ser
225                 230                 235                 240

Lys Ser Thr Ser Gly Gly Thr Ala Ala Leu Gly Cys Leu Val Lys Asp
                245                 250                 255

Tyr Phe Pro Ser Asp Ile Ala Val Glu Trp Glu Ser Gly Ala Leu Thr
            260                 265                 270

Ser Gly Val His Thr Phe Pro Ala Val Leu Gln Ser Ser Gly Leu Tyr
        275                 280                 285

Ser Leu Ser Ser Val Val Thr Val Pro Ser Ser Ser Leu Gly Thr Gln
    290                 295                 300

Thr Tyr Ser Cys Ser Val Met His Glu Ala Leu His Asn His Tyr Thr
305                 310                 315                 320

Gln Lys Ser Val Glu Pro Lys Ser Cys
                325

<210> SEQ ID NO 35
<211> LENGTH: 330
<212> TYPE: PRT
<213> ORGANISM: Homo sapiens

<400> SEQUENCE: 35

Asp Val Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Ser
                85                  90                  95

Thr His Val Pro Tyr Thr Phe Gly Gly Gly Thr Lys Val Glu Ile Lys
            100                 105                 110

Gly Thr Gly Gly Gly Ser Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190
```

```
Gln Asp Trp Leu Asn Gly Lys Glu Tyr Lys Cys Lys Val Ser Asn Lys
                195                 200                 205

Gly Leu Pro Ser Ser Ile Glu Lys Thr Ile Ser Lys Ala Lys Gly Gln
        210                 215                 220

Pro Arg Glu Pro Ser Val Phe Ile Phe Pro Pro Ser Asp Glu Gln Leu
225                 230                 235                 240

Lys Ser Gly Thr Ala Ser Val Val Cys Leu Val Asn Asn Phe Tyr Pro
            245                 250                 255

Arg Asp Ile Ala Val Glu Trp Glu Val Asp Asn Ala Leu Gln Ser Gly
                260                 265                 270

Asn Ser Gln Glu Ser Val Thr Glu Gln Asp Ser Lys Asp Ser Thr Tyr
        275                 280                 285

Ser Leu Ser Ser Thr Leu Thr Leu Ser Lys Ala Asp Tyr Glu Lys His
290                 295                 300

Lys Val Tyr Ser Cys Ser Val Met His Glu Ala Leu His Asn His Tyr
305                 310                 315                 320

Thr Gln Lys Ser Phe Asn Arg Gly Glu Cys
                325                 330

<210> SEQ ID NO 36
<211> LENGTH: 468
<212> TYPE: PRT
<213> ORGANISM: Homo sapiens

<400> SEQUENCE: 36

His Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Phe
            20                  25                  30

Tyr Ile Asn Trp Val Arg Gln Ala Pro Gly Gln Gly Leu Glu Trp Ile
        35                  40                  45

Gly Glu Ile Val Pro Ser Gln Gly Glu Ala Lys Tyr Asn Asp Lys Phe
    50                  55                  60

Lys Ala Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Phe Leu Asp Tyr Trp Gly Gln Gly Thr Thr Val Thr
            100                 105                 110

Val Ser Ser Gly Gly Gly Gly Ser Gly Gly Gly Ser Gly Gly Gly
        115                 120                 125

Gly Ser Asp Val Gln Met Thr Gln Ser Pro Ser Ser Leu Ser Ala Ser
    130                 135                 140

Val Gly Asp Arg Val Thr Ile Thr Cys Arg Ser Ser Gln Ser Leu Leu
145                 150                 155                 160

His Ser Asn Gly Asn Thr Tyr Leu His Trp Tyr Gln Gln Lys Pro Gly
                165                 170                 175

Lys Ala Pro Lys Leu Leu Ile Tyr Thr Val Ser Asn Arg Phe Ser Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Ser
    210                 215                 220

Gln Ser Thr His Val Pro Tyr Thr Phe Gly Gly Gly Thr Lys Val Glu
```

```
            225                 230                 235                 240
    Ile Lys Ala Ala Ala Asp Lys Thr His Thr Cys Pro Pro Cys Pro Ala
                    245                 250                 255

Pro Pro Val Ala Gly Pro Ser Val Phe Leu Phe Pro Pro Lys Pro Lys
                    260                 265                 270

Asp Thr Leu Met Ile Ser Arg Thr Pro Glu Val Thr Cys Val Val Val
                    275                 280                 285

Asp Val Ser His Glu Asp Pro Glu Val Lys Phe Asn Trp Tyr Val Asp
                    290                 295                 300

Gly Val Glu Val His Asn Ala Lys Thr Lys Pro Arg Glu Glu Gln Tyr
    305                 310                 315                 320

Asn Ser Thr Tyr Arg Val Val Ser Val Leu Thr Val Leu His Gln Asp
                    325                 330                 335

Trp Leu Asn Gly Lys Glu Tyr Lys Cys Lys Val Ser Asn Lys Gly Leu
                    340                 345                 350

Pro Ser Ser Ile Glu Lys Thr Ile Ser Lys Ala Lys Gly Gln Pro Arg
                    355                 360                 365

Glu Pro Ser Val Phe Pro Leu Ala Pro Ser Ser Lys Ser Thr Ser Gly
                    370                 375                 380

Gly Thr Ala Ala Leu Gly Cys Leu Val Lys Asp Tyr Phe Pro Ser Asp
    385                 390                 395                 400

Ile Ala Val Glu Trp Glu Ser Gly Ala Leu Thr Ser Gly Val His Thr
                    405                 410                 415

Phe Pro Ala Val Leu Gln Ser Ser Gly Leu Tyr Ser Leu Ser Ser Val
                    420                 425                 430

Val Thr Val Pro Ser Ser Ser Leu Gly Thr Gln Thr Tyr Ser Cys Ser
                    435                 440                 445

Val Met His Glu Ala Leu His Asn His Tyr Thr Gln Lys Ser Val Glu
                    450                 455                 460

Pro Lys Ser Cys
    465

<210> SEQ ID NO 37
<211> LENGTH: 227
<212> TYPE: PRT
<213> ORGANISM: Homo sapiens

<400> SEQUENCE: 37

Asp Lys Thr His Thr Cys Pro Pro Cys Pro Ala Pro Val Ala Gly
    1               5                   10                  15

Pro Ser Val Phe Leu Phe Pro Pro Lys Pro Lys Asp Thr Leu Met Ile
                    20                  25                  30

Ser Arg Thr Pro Glu Val Thr Cys Val Val Val Asp Val Ser His Glu
                    35                  40                  45

Asp Pro Glu Val Lys Phe Asn Trp Tyr Val Asp Gly Val Glu Val His
                    50                  55                  60

Asn Ala Lys Thr Lys Pro Arg Glu Glu Gln Tyr Asn Ser Thr Tyr Arg
    65                  70                  75                  80

Val Val Ser Val Leu Thr Val Leu His Gln Asp Trp Leu Asn Gly Lys
                    85                  90                  95

Glu Tyr Lys Cys Lys Val Ser Asn Lys Gly Leu Pro Ser Ser Ile Glu
                    100                 105                 110

Lys Thr Ile Ser Lys Ala Lys Gly Gln Pro Arg Glu Pro Ser Val Phe
                    115                 120                 125
```

```
Ile Phe Pro Pro Ser Asp Glu Gln Leu Lys Ser Gly Thr Ala Ser Val
130                 135                 140

Val Cys Leu Val Asn Asn Phe Tyr Pro Arg Asp Ile Ala Val Glu Trp
145                 150                 155                 160

Glu Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ser Cys Ser Val
        195                 200                 205

Met His Glu Ala Leu His Asn His Tyr Thr Gln Lys Ser Phe Asn Arg
210                 215                 220

Gly Glu Cys
225

<210> SEQ ID NO 38
<211> LENGTH: 504
<212> TYPE: PRT
<213> ORGANISM: Homo sapiens

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Trp
                85                  90                  95

Thr Phe Gly Gln Gly Thr Lys Leu Glu Ile Lys Arg Gly Gly Gly Gly
            100                 105                 110

Ser Gly Gly Gly Gly Ser Gly Gly Gly Ser Gln Val Gln Leu Val
        115                 120                 125

Gln Ser Gly Ala Glu Val Lys Lys Pro Gly Ser Ser Val Lys Val Ser
130                 135                 140

Cys Lys Ala Ser Gly Gly Thr Phe Ser Gly Tyr Thr Met Asn Trp Val
145                 150                 155                 160

Arg Gln Ala Pro Gly Gln Gly Leu Glu Trp Met Gly Leu Ile Asn Pro
                165                 170                 175

Tyr Lys Gly Val Ser Thr Tyr Asn Gly Lys Phe Lys Asp Arg Val Thr
            180                 185                 190

Ile Thr Ala Asp Lys Ser Thr Ser Thr Ala Tyr Met Glu Leu Ser Ser
        195                 200                 205

Leu Arg Ser Glu Asp Thr Ala Val Tyr Tyr Cys Ala Arg Ser Gly Tyr
210                 215                 220

Tyr Gly Asp Ser Asp Trp Tyr Phe Asp Val Trp Gly Gln Gly Thr Leu
225                 230                 235                 240

Val Thr Val Ser Ser Gly Gly Gly Ser Gly Gly Gly Gly Ser Asp
                245                 250                 255

Lys Thr His Thr Cys Pro Pro Cys Pro Ala Pro Pro Val Ala Gly Pro
            260                 265                 270
```

```
Ser Val Phe Leu Phe Pro Pro Lys Pro Lys Asp Thr Leu Met Ile Ser
            275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
                340                 345                 350

Tyr Lys Cys Lys Val Ser Asn Lys Gly Leu Pro Ser Ser Ile Glu Lys
            355                 360                 365

Thr Ile Ser Lys Ala Lys Gly Gln Pro Arg Glu Pro Ser Val Phe Ile
    370                 375                 380

Phe Pro Pro Ser Asp Glu Gln Leu Lys Ser Gly Thr Ala Ser Val Val
385                 390                 395                 400

Cys Leu Val Asn Asn Phe Tyr Pro Arg Asp Ile Ala Val Glu Trp Glu
                405                 410                 415

Val Asp Asn Ala Leu Gln Ser Gly Asn Ser Gln Glu Ser Val Thr Glu
                420                 425                 430

Gln Asp Ser Lys Asp Ser Thr Tyr Ser Leu Ser Ser Thr Leu Thr Leu
            435                 440                 445

Ser Lys Ala Asp Tyr Glu Lys His Lys Val Tyr Ser Cys Ser Val Met
    450                 455                 460

His Glu Ala Leu His Asn His Tyr Thr Gln Lys Ser Phe Asn Arg Gly
465                 470                 475                 480

Glu Cys Gly Gly Gly Gly Ser Gly Gly Gly Gly Ser Gly Gly Gly Gly
                485                 490                 495

Ser Gly Thr Gly Gly Ser Gly Gly
            500

<210> SEQ ID NO 39
<211> LENGTH: 472
<212> TYPE: PRT
<213> ORGANISM: Homo sapiens

<400> SEQUENCE: 39

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Arg Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Gln Ser Leu Lys Ser Arg Ile Thr Ile Asn Pro Asp Thr Pro Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Gly Gln Leu Gly Leu Asp Ala Leu Asp Ile
            100                 105                 110

Trp Gly Gln Gly Thr Met Val Thr Val Ser Ser Gly Gly Gly Gly Ser
        115                 120                 125

Gly Gly Gly Gly Ser Gly Gly Gly Gly Ser Gln Ala Gly Leu Thr Gln
```

```
            130                 135                 140
Pro Pro Ala Val Ser Val Ala Pro Gly Gln Thr Ala Ser Ile Thr Cys
145                 150                 155                 160

Gly Arg Asp Asn Ile Gly Ser Arg Ser Val His Trp Tyr Gln Gln Lys
                165                 170                 175

Pro Gly Gln Ala Pro Val Leu Val Val Tyr Asp Asp Ser Asp Arg Pro
            180                 185                 190

Ala Gly Ile Pro Glu Arg Phe Ser Gly Ser Asn Tyr Glu Asn Thr Ala
        195                 200                 205

Thr Leu Thr Ile Ser Arg Val Glu Ala Gly Asp Glu Ala Asp Tyr Tyr
    210                 215                 220

Cys Gln Val Trp Gly Ile Thr Ser Asp His Val Val Phe Gly Gly Gly
225                 230                 235                 240

Thr Lys Leu Thr Val Leu Ala Ala Ala Asp Lys Thr His Thr Cys Pro
                245                 250                 255

Pro Cys Pro Ala Pro Pro Val Ala Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Gly Leu Pro Ser Ser Ile Glu Lys Thr Ile Ser Lys Ala Lys
        355                 360                 365

Gly Gln Pro Arg Glu Pro Ser Val Phe Pro Leu Ala Pro Ser Ser Lys
    370                 375                 380

Ser Thr Ser Gly Gly Thr Ala Ala Leu Gly Cys Leu Val Lys Asp Tyr
385                 390                 395                 400

Phe Pro Ser Asp Ile Ala Val Glu Trp Glu Ser Gly Ala Leu Thr Ser
                405                 410                 415

Gly Val His Thr Phe Pro Ala Val Leu Gln Ser Ser Gly Leu Tyr Ser
            420                 425                 430

Leu Ser Ser Val Val Thr Val Pro Ser Ser Ser Leu Gly Thr Gln Thr
        435                 440                 445

Tyr Ser Cys Ser Val Met His Glu Ala Leu His Asn His Tyr Thr Gln
    450                 455                 460

Lys Ser Val Glu Pro Lys Ser Cys
465                 470

<210> SEQ ID NO 40
<211> LENGTH: 474
<212> TYPE: PRT
<213> ORGANISM: Homo sapiens

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Ser
            20                  25                  30
```

```
Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Asn Gly Lys Phe
 50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Asn Thr Val Val Pro Tyr Thr Met Asp Tyr Trp Gly
                100                 105                 110

Gln Gly Thr Thr Val Thr Val Ser Ser Gly Gly Gly Ser Gly Gly
            115                 120                 125

Gly Gly Ser Gly Gly Gly Ser Asp Ile Gln Met Thr Gln Ser Pro
130                 135                 140

Ser Ser Leu Ser Ala Ser Val Gly Asp Arg Val Thr Ile Thr Cys Arg
145                 150                 155                 160

Ala Ser Glu Ser Val Asp Ser Tyr Gly Asn Ser Phe Met His Trp Tyr
                165                 170                 175

Gln Gln Lys Pro Gly Lys Ala Pro Lys Leu Leu Ile Tyr Leu Ala Ser
            180                 185                 190

Asn Leu Glu Ser Gly Val Pro Ser Arg Phe Ser Gly Ser Gly Ser Gly
                195                 200                 205

Thr Asp Phe Thr Leu Thr Ile Ser Ser Leu Gln Pro Glu Asp Phe Ala
210                 215                 220

Thr Tyr Tyr Cys Gln Gln Asn Asn Glu Asp Pro Leu Thr Phe Gly Gly
225                 230                 235                 240

Gly Thr Lys Val Glu Ile Lys Arg Ala Ala Ala Asp Lys Thr His Thr
                245                 250                 255

Cys Pro Pro Cys Pro Ala Pro Pro Val Ala Gly Pro Ser Val Phe Leu
                260                 265                 270

Phe Pro Pro Lys Pro Lys Asp Thr Leu Met Ile Ser Arg Thr Pro Glu
            275                 280                 285

Val Thr Cys Val Val Val Asp Val Ser His Glu Asp Pro Glu Val Lys
            290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Gly Leu Pro Ser Ser Ile Glu Lys Thr Ile Ser Lys
            355                 360                 365

Ala Lys Gly Gln Pro Arg Glu Pro Ser Val Phe Pro Leu Ala Pro Ser
370                 375                 380

Ser Lys Ser Thr Ser Gly Gly Thr Ala Ala Leu Gly Cys Leu Val Lys
385                 390                 395                 400

Asp Tyr Phe Pro Ser Asp Ile Ala Val Glu Trp Glu Ser Gly Ala Leu
                405                 410                 415

Thr Ser Gly Val His Thr Phe Pro Ala Val Leu Gln Ser Ser Gly Leu
                420                 425                 430

Tyr Ser Leu Ser Ser Val Val Thr Val Pro Ser Ser Ser Leu Gly Thr
            435                 440                 445

Gln Thr Tyr Ser Cys Ser Val Met His Glu Ala Leu His Asn His Tyr
```

```
                  450                 455                 460
Thr Gln Lys Ser Val Glu Pro Lys Ser Cys
465                 470

<210> SEQ ID NO 41
<211> LENGTH: 333
<212> TYPE: PRT
<213> ORGANISM: Homo sapiens

<400> SEQUENCE: 41

His Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Phe
                20                  25                  30

Tyr Ile Asn Trp Val Arg Gln Ala Pro Gly Gln Gly Leu Glu Trp Ile
            35                  40                  45

Gly Glu Ile Val Pro Ser Gln Gly Glu Ala Lys Tyr Asn Asp Lys Phe
        50                  55                  60

Lys Ala Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Phe Leu Asp Tyr Trp Gly Gln Gly Thr Thr Val Thr
            100                 105                 110

Val Ser Ser Gly Thr Gly Gly Ser Gly Pro Ser Val Phe Leu Phe
        115                 120                 125

Pro Pro Lys Pro Lys Asp Thr Leu Met Ile Ser Arg Thr Pro Glu Val
130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Gly Leu Pro Ser Ser Ile Glu Lys Thr Ile Ser Lys Ala
    210                 215                 220

Lys Gly Gln Pro Arg Glu Pro Ser Val Phe Ile Phe Pro Pro Ser Asp
225                 230                 235                 240

Glu Gln Leu Lys Ser Gly Thr Ala Ser Val Val Cys Leu Val Asn Asn
                245                 250                 255

Phe Tyr Pro Arg Asp Ile Ala Val Glu Trp Glu Val Asp Asn Ala Leu
            260                 265                 270

Gln Ser Gly Asn Ser Gln Glu Ser Val Thr Glu Gln Asp Ser Lys Asp
        275                 280                 285

Ser Thr Tyr Ser Leu Ser Ser Thr Leu Thr Leu Ser Lys Ala Asp Tyr
    290                 295                 300

Glu Lys His Lys Val Tyr Ser Cys Ser Val Met His Glu Ala Leu His
305                 310                 315                 320

Asn His Tyr Thr Gln Lys Ser Phe Asn Arg Gly Glu Cys
                325                 330

<210> SEQ ID NO 42
<211> LENGTH: 326
```

```
<212> TYPE: PRT
<213> ORGANISM: Homo sapiens

<400> SEQUENCE: 42

Asp Val Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Ser
                20                  25                  30

Asn Gly Asn Thr Tyr Leu His Trp Tyr Gln Gln Lys Pro Gly Lys Ala
            35                  40                  45

Pro Lys Leu Leu Ile Tyr Thr Val Ser Asn Arg Phe Ser Gly Val Pro
        50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Ser
                85                  90                  95

Thr His Val Pro Tyr Thr Phe Gly Gly Gly Thr Lys Val Glu Ile Lys
                100                 105                 110

Gly Thr Gly Gly Gly Ser Gly Pro Ser Val Phe Leu Phe Pro Pro Lys
            115                 120                 125

Pro Lys Asp Thr Leu Met Ile Ser Arg Thr Pro Glu Val Thr Cys Val
        130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
210                 215                 220

Pro Arg Glu Pro Ser Val Phe Pro Leu Ala Pro Ser Ser Lys Ser Thr
225                 230                 235                 240

Ser Gly Gly Thr Ala Ala Leu Gly Cys Leu Val Lys Asp Tyr Phe Pro
                245                 250                 255

Ser Asp Ile Ala Val Glu Trp Glu Ser Gly Ala Leu Thr Ser Gly Val
            260                 265                 270

His Thr Phe Pro Ala Val Leu Gln Ser Ser Gly Leu Tyr Ser Leu Ser
        275                 280                 285

Ser Val Val Thr Val Pro Ser Ser Ser Leu Gly Thr Gln Thr Tyr Ser
        290                 295                 300

Cys Ser Val Met His Glu Ala Leu His Asn His Tyr Thr Gln Lys Ser
305                 310                 315                 320

Val Glu Pro Lys Ser Cys
                325

<210> SEQ ID NO 43
<211> LENGTH: 599
<212> TYPE: PRT
<213> ORGANISM: Homo sapiens

<400> SEQUENCE: 43

Gln Val Gln Leu Val Gln Ser Gly Ala Glu Val Lys Lys Pro Gly Ser
1               5                   10                  15
```

-continued

```
Ser Val Lys Val Ser Cys Lys Ala Ser Gly Gly Thr Phe Ser Gly Tyr
             20                  25                  30

Thr Met Asn Trp Val Arg Gln Ala Pro Gly Gln Gly Leu Glu Trp Met
         35                  40                  45

Gly Leu Ile Asn Pro Tyr Lys Gly Val Ser Thr Tyr Asn Gly Lys Phe
     50                  55                  60

Lys Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Ser Gly Tyr Tyr Gly Asp Ser Asp Trp Tyr Phe Asp Val Trp
        100                 105                 110

Gly Gln Gly Thr Leu Val Thr Val Ser Ser Gly Thr Gly Gly Gly Ser
        115                 120                 125

Gly Pro Ser Val Phe Leu Phe Pro Pro Lys Pro Lys Asp Thr Leu Met
    130                 135                 140

Ile Ser Arg Thr Pro Glu Val Thr Cys Val Val Val Asp Val Ser His
145                 150                 155                 160

Glu Asp Pro Glu Val Lys Phe Asn Trp Tyr Val Asp Gly Val Glu Val
            165                 170                 175

His Asn Ala Lys Thr Lys Pro Arg Glu Glu Gln Tyr Asn Ser Thr Tyr
        180                 185                 190

Arg Val Val Ser Val Leu Thr Val Leu His Gln Asp Trp Leu Asn Gly
        195                 200                 205

Lys Glu Tyr Lys Cys Lys Val Ser Asn Lys Gly Leu Pro Ser Ser Ile
    210                 215                 220

Glu Lys Thr Ile Ser Lys Ala Lys Gly Gln Pro Arg Glu Pro Ser Val
225                 230                 235                 240

Phe Ile Phe Pro Pro Ser Asp Glu Gln Leu Lys Ser Gly Thr Ala Ser
            245                 250                 255

Val Val Cys Leu Val Asn Asn Phe Tyr Pro Arg Asp Ile Ala Val Glu
        260                 265                 270

Trp Glu Val Asp Asn Ala Leu Gln Ser Gly Asn Ser Gln Glu Ser Val
    275                 280                 285

Thr Glu Gln Asp Ser Lys Asp Ser Thr Tyr Ser Leu Ser Ser Thr Leu
    290                 295                 300

Thr Leu Ser Lys Ala Asp Tyr Glu Lys His Lys Val Tyr Ser Cys Ser
305                 310                 315                 320

Val Met His Glu Ala Leu His Asn His Tyr Thr Gln Lys Ser Phe Asn
            325                 330                 335

Arg Gly Glu Cys Asp Lys Thr His Thr Ala Pro Ala Pro Pro Val Ala
        340                 345                 350

Gly Gln Val Gln Leu Gln Gln Ser Gly Pro Gly Leu Val Lys Pro Ser
    355                 360                 365

Gln Thr Leu Ser Leu Thr Cys Ala Ile Ser Gly Asp Ser Val Ser Ser
    370                 375                 380

Asn Arg Ala Ala Trp Asn Trp Ile Arg Gln Ser Pro Ser Arg Gly Leu
385                 390                 395                 400

Glu Trp Leu Gly Arg Thr Tyr Tyr Arg Ser Lys Trp Tyr Asn Asp Tyr
            405                 410                 415

Ala Gln Ser Leu Lys Ser Arg Ile Thr Ile Asn Pro Asp Thr Pro Lys
        420                 425                 430

Asn Gln Phe Ser Leu Gln Leu Asn Ser Val Thr Pro Glu Asp Thr Ala
```

```
                435                 440                 445
Val Tyr Tyr Cys Ala Arg Asp Gly Gln Leu Gly Leu Asp Ala Leu Asp
450                 455                 460

Ile Trp Gly Gln Gly Thr Met Val Thr Val Ser Ser Gly Gly Gly Gly
465                 470                 475                 480

Ser Gly Gly Gly Gly Ser Gly Gly Gly Ser Gln Ala Gly Leu Thr
                485                 490                 495

Gln Pro Pro Ala Val Ser Val Ala Pro Gly Gln Thr Ala Ser Ile Thr
                500                 505                 510

Cys Gly Arg Asp Asn Ile Gly Ser Arg Ser Val His Trp Tyr Gln Gln
                515                 520                 525

Lys Pro Gly Gln Ala Pro Val Leu Val Val Tyr Asp Asp Ser Asp Arg
                530                 535                 540

Pro Ala Gly Ile Pro Glu Arg Phe Ser Gly Ser Asn Tyr Glu Asn Thr
545                 550                 555                 560

Ala Thr Leu Thr Ile Ser Arg Val Glu Ala Gly Asp Glu Ala Asp Tyr
                565                 570                 575

Tyr Cys Gln Val Trp Gly Ile Thr Ser Asp His Val Val Phe Gly Gly
                580                 585                 590

Gly Thr Lys Leu Thr Val Leu
                595

<210> SEQ ID NO 44
<211> LENGTH: 580
<212> TYPE: PRT
<213> ORGANISM: Homo sapiens

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Trp
                85                  90                  95

Thr Phe Gly Gln Gly Thr Lys Leu Glu Ile Lys Gly Thr Gly Gly Gly
                100                 105                 110

Ser Gly Pro Ser Val Phe Leu Phe Pro Pro Lys Pro Lys Asp Thr Leu
            115                 120                 125

Met Ile Ser Arg Thr Pro Glu Val Thr Cys Val Val Val Asp Val Ser
130                 135                 140

His Glu Asp Pro Glu Val Lys Phe Asn Trp Tyr Val Asp Gly Val Glu
145                 150                 155                 160

Val His Asn Ala Lys Thr Lys Pro Arg Glu Glu Gln Tyr Asn Ser Thr
                165                 170                 175

Tyr Arg Val Val Ser Val Leu Thr Val Leu His Gln Asp Trp Leu Asn
                180                 185                 190

Gly Lys Glu Tyr Lys Cys Lys Val Ser Asn Lys Gly Leu Pro Ser Ser
            195                 200                 205
```

```
Ile Glu Lys Thr Ile Ser Lys Ala Lys Gly Gln Pro Arg Glu Pro Ser
    210                 215                 220

Val Phe Pro Leu Ala Pro Ser Ser Lys Ser Thr Ser Gly Gly Thr Ala
225                 230                 235                 240

Ala Leu Gly Cys Leu Val Lys Asp Tyr Phe Pro Ser Asp Ile Ala Val
                245                 250                 255

Glu Trp Glu Ser Gly Ala Leu Thr Ser Gly Val His Thr Phe Pro Ala
            260                 265                 270

Val Leu Gln Ser Ser Gly Leu Tyr Ser Leu Ser Ser Val Val Thr Val
        275                 280                 285

Pro Ser Ser Ser Leu Gly Thr Gln Thr Tyr Ser Cys Ser Val Met His
290                 295                 300

Glu Ala Leu His Asn His Tyr Thr Gln Lys Ser Val Glu Pro Lys Ser
305                 310                 315                 320

Cys Asp Lys Thr His Thr Ala Pro Ala Pro Pro Val Ala Gly Gln Val
                325                 330                 335

Gln Leu Gln Gln Ser Gly Pro Gly Leu Val Lys Pro Ser Gln Thr Leu
            340                 345                 350

Ser Leu Thr Cys Ala Ile Ser Gly Asp Ser Val Ser Ser Asn Arg Ala
        355                 360                 365

Ala Trp Asn Trp Ile Arg Gln Ser Pro Ser Arg Gly Leu Glu Trp Leu
370                 375                 380

Gly Arg Thr Tyr Tyr Arg Ser Lys Trp Tyr Asn Asp Tyr Ala Gln Ser
385                 390                 395                 400

Leu Lys Ser Arg Ile Thr Ile Asn Pro Asp Thr Pro Lys Asn Gln Phe
                405                 410                 415

Ser Leu Gln Leu Asn Ser Val Thr Pro Glu Asp Thr Ala Val Tyr Tyr
            420                 425                 430

Cys Ala Arg Asp Gly Gln Leu Gly Leu Asp Ala Leu Asp Ile Trp Gly
        435                 440                 445

Gln Gly Thr Met Val Thr Val Ser Ser Gly Gly Gly Ser Gly Gly
450                 455                 460

Gly Gly Ser Gly Gly Gly Gly Ser Gln Ala Gly Leu Thr Gln Pro Pro
465                 470                 475                 480

Ala Val Ser Val Ala Pro Gly Gln Thr Ala Ser Ile Thr Cys Gly Arg
                485                 490                 495

Asp Asn Ile Gly Ser Arg Ser Val His Trp Tyr Gln Gln Lys Pro Gly
            500                 505                 510

Gln Ala Pro Val Leu Val Val Tyr Asp Asp Ser Asp Arg Pro Ala Gly
        515                 520                 525

Ile Pro Glu Arg Phe Ser Gly Ser Asn Tyr Glu Asn Thr Ala Thr Leu
530                 535                 540

Thr Ile Ser Arg Val Glu Ala Gly Asp Glu Ala Asp Tyr Tyr Cys Gln
545                 550                 555                 560

Val Trp Gly Ile Thr Ser Asp His Val Val Phe Gly Gly Gly Thr Lys
                565                 570                 575

Leu Thr Val Leu
            580

<210> SEQ ID NO 45
<211> LENGTH: 107
<212> TYPE: PRT
<213> ORGANISM: Homo sapiens

<400> SEQUENCE: 45
```

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 46
<211> LENGTH: 107
<212> TYPE: PRT
<213> ORGANISM: Homo sapiens

<400> SEQUENCE: 46

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Met Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 47
<211> LENGTH: 107
<212> TYPE: PRT
<213> ORGANISM: Homo sapiens

<400> SEQUENCE: 47

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Ser Gly Gln Pro Glu
        35                  40                  45

Asn Asn Tyr Asn Thr Thr Pro Pro Met Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro Gly Lys
            100                 105

<210> SEQ ID NO 48
<211> LENGTH: 107
<212> TYPE: PRT
<213> ORGANISM: Homo sapiens

<400> SEQUENCE: 48

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 49
<211> LENGTH: 112
<212> TYPE: PRT
<213> ORGANISM: Homo sapiens

<400> SEQUENCE: 49

Val Ala Leu His Arg Pro Asp Val Tyr Leu Leu Pro Pro Ala Arg Glu
1               5                   10                  15

Gln Leu Asn Leu Arg Glu Ser Ala Thr Ile Thr Cys Leu Val Thr Gly
            20                  25                  30

Phe Ser Pro Ala Asp Val Phe Val Gln Trp Met Gln Arg Gly Gln Pro
        35                  40                  45

Leu Ser Pro Glu Lys Tyr Val Thr Ser Ala Pro Met Pro Glu Pro Gln
    50                  55                  60

Ala Pro Gly Arg Tyr Phe Ala His Ser Ile Leu Thr Val Ser Glu Glu
65                  70                  75                  80

Glu Trp Asn Thr Gly Glu Thr Tyr Thr Cys Val Val Ala His Glu Ala
                85                  90                  95

Leu Pro Asn Arg Val Thr Glu Arg Thr Val Asp Lys Ser Thr Gly Lys
            100                 105                 110

<210> SEQ ID NO 50
<211> LENGTH: 113
<212> TYPE: PRT
<213> ORGANISM: Homo sapiens

<400> SEQUENCE: 50

Gly Asn Thr Phe Arg Pro Glu Val His Leu Leu Pro Pro Pro Ser Glu
1               5                   10                  15

Glu Leu Ala Leu Asn Glu Leu Val Thr Leu Thr Cys Leu Ala Arg Gly
            20                  25                  30

Phe Ser Pro Lys Asp Val Leu Val Arg Trp Leu Gln Gly Ser Gln Glu
        35                  40                  45

Leu Pro Arg Glu Lys Tyr Leu Thr Trp Ala Ser Arg Gln Glu Pro Ser
    50                  55                  60

```
Gln Gly Thr Thr Thr Phe Ala Val Thr Ser Ile Leu Arg Val Ala Ala
 65                  70                  75                  80

Glu Asp Trp Lys Lys Gly Asp Thr Phe Ser Cys Met Val Gly His Glu
                 85                  90                  95

Ala Leu Pro Leu Ala Phe Thr Gln Lys Thr Ile Asp Arg Leu Ala Gly
            100                 105                 110

Lys

<210> SEQ ID NO 51
<211> LENGTH: 113
<212> TYPE: PRT
<213> ORGANISM: Homo sapiens

<400> SEQUENCE: 51

Gly Asn Thr Phe Arg Pro Glu Val His Leu Leu Pro Pro Ser Glu
 1               5                  10                  15

Glu Leu Ala Leu Asn Glu Leu Val Thr Leu Thr Cys Leu Ala Arg Gly
                20                  25                  30

Phe Ser Pro Lys Asp Val Leu Val Arg Trp Leu Gln Gly Ser Gln Glu
             35                  40                  45

Leu Pro Arg Glu Lys Tyr Leu Thr Trp Ala Ser Arg Gln Glu Pro Ser
 50                  55                  60

Gln Gly Thr Thr Thr Phe Ala Val Thr Ser Ile Leu Arg Val Ala Ala
 65                  70                  75                  80

Glu Asp Trp Lys Lys Gly Asp Thr Phe Ser Cys Met Val Gly His Glu
                 85                  90                  95

Ala Leu Pro Leu Ala Phe Thr Gln Lys Thr Ile Asp Arg Leu Ala Gly
            100                 105                 110

Lys

<210> SEQ ID NO 52
<211> LENGTH: 112
<212> TYPE: PRT
<213> ORGANISM: Homo sapiens

<400> SEQUENCE: 52

Val Pro Ala Gln Ala Pro Val Lys Leu Ser Leu Asn Leu Leu Ala Ser
 1               5                  10                  15

Ser Asp Pro Pro Glu Ala Ala Ser Trp Leu Leu Cys Glu Val Ser Gly
                20                  25                  30

Phe Ser Pro Pro Asn Ile Leu Leu Met Trp Leu Glu Asp Gln Arg Glu
             35                  40                  45

Val Asn Thr Ser Gly Phe Ala Pro Ala Arg Pro Pro Pro Gln Pro Gly
 50                  55                  60

Ser Thr Thr Phe Trp Ala Trp Ser Val Leu Arg Val Pro Ala Pro Pro
 65                  70                  75                  80

Ser Pro Gln Pro Ala Thr Tyr Thr Cys Val Val Ser His Glu Asp Ser
                 85                  90                  95

Arg Thr Leu Leu Asn Ala Ser Arg Ser Leu Glu Val Ser Tyr Val Thr
            100                 105                 110

<210> SEQ ID NO 53
<211> LENGTH: 110
<212> TYPE: PRT
<213> ORGANISM: Homo sapiens

<400> SEQUENCE: 53
```

Gly Pro Arg Ala Ala Pro Glu Val Tyr Ala Phe Ala Thr Pro Glu Trp
1               5                   10                  15

Pro Gly Ser Arg Asp Lys Arg Thr Leu Ala Cys Leu Ile Gln Asn Phe
            20                  25                  30

Met Pro Glu Asp Ile Ser Val Gln Trp Leu His Asn Glu Val Gln Leu
        35                  40                  45

Pro Asp Ala Arg His Ser Thr Thr Gln Pro Arg Lys Thr Lys Gly Ser
    50                  55                  60

Gly Phe Phe Val Phe Ser Arg Leu Glu Val Thr Arg Ala Glu Trp Glu
65                  70                  75                  80

Gln Lys Asp Glu Phe Ile Cys Arg Ala Val His Glu Ala Ala Ser Pro
                85                  90                  95

Ser Gln Thr Val Gln Arg Ala Val Ser Val Asn Pro Gly Lys
            100                 105                 110

<210> SEQ ID NO 54
<211> LENGTH: 106
<212> TYPE: PRT
<213> ORGANISM: Homo sapiens

<400> SEQUENCE: 54

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 55
<211> LENGTH: 106
<212> TYPE: PRT
<213> ORGANISM: Homo sapiens

<400> SEQUENCE: 55

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Ala Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 56
<211> LENGTH: 106
<212> TYPE: PRT
<213> ORGANISM: Homo sapiens

<400> SEQUENCE: 56

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105

<210> SEQ ID NO 57
<211> LENGTH: 106
<212> TYPE: PRT
<213> ORGANISM: Homo sapiens

<400> SEQUENCE: 57

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105

<210> SEQ ID NO 58
<211> LENGTH: 131
<212> TYPE: PRT
<213> ORGANISM: Homo sapiens

<400> SEQUENCE: 58

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
50                  55                  60

Glu Gln Pro Ala Leu Asn Asp Ser Arg Tyr Cys Leu Ser Ser Arg Leu

```
                65                  70                  75                  80
Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
            115                 120                 125

Ala Asp Cys
        130

<210> SEQ ID NO 59
<211> LENGTH: 113
<212> TYPE: PRT
<213> ORGANISM: Homo sapiens

<400> SEQUENCE: 59

Trp Gly Ser Leu Thr Asn Arg Thr Arg Pro Pro Ser Val Gln Val Ala
1               5                   10                  15

Lys Thr Thr Pro Phe Asn Thr Arg Glu Pro Val Met Leu Ala Cys Tyr
            20                  25                  30

Val Trp Gly Phe Tyr Pro Ala Glu Val Thr Ile Thr Trp Arg Lys Asn
            35                  40                  45

Gly Lys Leu Val Met His Ser Ser Ala His Lys Thr Ala Gln Pro Asn
        50                  55                  60

Gly Asp Trp Thr Tyr Gln Thr Leu Ser His Leu Ala Leu Thr Pro Ser
65                  70                  75                  80

Tyr Gly Asp Thr Tyr Thr Cys Val Val Glu His Ile Gly Ala Pro Glu
                85                  90                  95

Pro Ile Leu Arg Asp Trp Thr Pro Gly Leu Ser Pro Met Gln Thr Leu
            100                 105                 110

Lys
```